United States Patent
Bangera et al.

(10) Patent No.: US 10,182,869 B2
(45) Date of Patent: Jan. 22, 2019

(54) SYSTEMS AND METHODS FOR WEARABLE INJECTION GUIDES

(71) Applicant: Elwha LLC, Bellevue, WA (US)

(72) Inventors: Mahalaxmi Gita Bangera, Renton, WA (US); Edward S. Boyden, Chestnut Hill, MA (US); Hon Wah Chin, Palo Alto, CA (US); Gregory J. Della Rocca, Columbia, MO (US); Daniel Hawkins, Pleasanton, CA (US); Roderick A. Hyde, Redmond, WA (US); Muriel Y. Ishikawa, Livermore, CA (US); Jordin T. Kare, San Jose, CA (US); Robert Langer, Newton, MA (US); Eric C. Leuthardt, St. Louis, MO (US); Stephen L. Malaska, Redmond, WA (US); Terence Myckatyn, St. Louis, MO (US); Parag Jitendra Parikh, St. Louis, MO (US); Dennis J. Rivet, Richmond, VA (US); Joshua S. Shimony, St. Louis, MO (US); Michael A. Smith, Phoeniz, AZ (US); Elizabeth A. Sweeney, Seattle, WA (US); Clarence T. Tegreene, Mercer Island, WA (US); Sharon L. Wolda, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 270 days.

(21) Appl. No.: 15/141,638

(22) Filed: Apr. 28, 2016

(65) Prior Publication Data
US 2016/0235929 A1 Aug. 18, 2016

Related U.S. Application Data

(63) Continuation of application No. 13/568,033, filed on Aug. 6, 2012, now Pat. No. 9,358,350, which is a
(Continued)

(51) Int. Cl.
*A61B 34/10* (2016.01)
*A61M 5/42* (2006.01)
(Continued)

(52) U.S. Cl.
CPC .......... *A61B 34/10* (2016.02); *A61B 17/3403* (2013.01); *A61M 5/422* (2013.01);
(Continued)

(58) Field of Classification Search
CPC ................ A61B 34/10; A61B 17/3403; A61B 2034/108; B29C 67/0088; G05B 19/4099;
(Continued)

(56) References Cited

U.S. PATENT DOCUMENTS 4,362,157 A * 12/1982 Keeth .................. A61M 5/427
604/116
4,526,752 A 7/1985 Perlman et al.
(Continued)

FOREIGN PATENT DOCUMENTS

| GB | 2 431 110 A | 4/2007 |
|---|---|---|
| WO | WO 80/00060 | 1/1980 |
| WO | WO 2004/035110 A2 | 4/2004 |

OTHER PUBLICATIONS

Allemann, Inja Bogdan et al., "Hyaluronic acid gel (Juvéderm™) preparations in the treatment of facial wrinkles and folds", Clinical Interventions in Aging, 2008, pp. 629-634, vol. 3, No. 4, 2008 Dove Medical Press Limited.
(Continued)

*Primary Examiner* — Mohammad Ali
*Assistant Examiner* — Kelvin Booker

(57) ABSTRACT

Systems and methods for wearable injection guides are described, which include: acquiring one or more digital images of a body region of an individual with at least one image capture device; creating a digitally rendered model of a wearable injection guide from the one or more digital images of the body region of the individual; adding one or more digitally rendered fiducials indicative of at least one treatment parameter to the digitally rendered model of the
(Continued)

wearable injection guide; and forming the wearable injection guide from the digitally rendered model of the wearable injection guide, the formed wearable injection guide including one or more fiducials corresponding to the one or more digitally rendered fiducials on the digitally rendered model of the wearable injection guide.

41 Claims, 44 Drawing Sheets

Related U.S. Application Data continuation-in-part of application No. 13/567,995, filed on Aug. 6, 2012, now Pat. No. 9,205,204, which is a continuation-in-part of application No. 13/567,921, filed on Aug. 6, 2012, now Pat. No. 9,199,044.

(51) Int. Cl.
| | |
|---|---|
| *G06F 17/50* | (2006.01) |
| *G05B 19/40* | (2006.01) |
| *A61M 5/46* | (2006.01) |
| *A61B 17/34* | (2006.01) |
| *G05B 19/4099* | (2006.01) |
| *B29C 64/386* | (2017.01) |
| *B33Y 80/00* | (2015.01) |
| *A61B 90/00* | (2016.01) |
| *B33Y 50/02* | (2015.01) |

(52) U.S. Cl.
CPC .............. *A61M 5/427* (2013.01); *A61M 5/46* (2013.01); *B29C 64/386* (2017.08); *G05B 19/4099* (2013.01); *G06F 17/5086* (2013.01); *A61B 2017/3411* (2013.01); *A61B 2034/108* (2016.02); *A61B 2090/363* (2016.02); *A61M 2205/13* (2013.01); *A61M 2207/00* (2013.01); *A61M 2210/0606* (2013.01); *B33Y 50/02* (2014.12); *B33Y 80/00* (2014.12); *G05B 2219/35134* (2013.01); *G05B 2219/49007* (2013.01)

(58) Field of Classification Search
CPC ........... G05B 2219/35134; G05B 2219/49007; A61M 5/422; A61M 5/46; A61M 5/427; A61M 2207/00; G06F 17/5086; B33Y 80/00; B33Y 50/02
See application file for complete search history.

(56) References Cited

U.S. PATENT DOCUMENTS

| | | | |
|---|---|---|---|
| 4,614,189 A | 9/1986 | MacKenzie | |
| 4,679,553 A | 7/1987 | Proulx et al. | |
| 4,990,284 A | 2/1991 | Lauterbach et al. | |
| 5,235,987 A | 8/1993 | Wolfe | |
| 5,356,396 A | 10/1994 | Wyatt et al. | |
| 5,466,233 A | 11/1995 | Weiner et al. | |
| 5,752,962 A | 5/1998 | D'Urso | |
| 5,782,842 A | 7/1998 | Kloess et al. | |
| 5,860,957 A | 1/1999 | Jacobsen et al. | |
| 5,971,763 A * | 10/1999 | Yau ........................ | G09B 19/00 |
| | | | 132/319 |
| 5,990,199 A | 11/1999 | Bealing et al. | |
| 6,036,632 A | 3/2000 | Whitmore, III et al. | |
| 6,041,249 A | 3/2000 | Regn | |
| 6,196,223 B1 | 3/2001 | Belfer et al. | |
| 6,200,255 B1 | 3/2001 | Yu | |
| 6,216,029 B1 | 4/2001 | Paltieli | |
| 6,311,084 B1 | 10/2001 | Cormack et al. | |
| 6,350,276 B1 | 2/2002 | Knowlton | |
| 6,428,504 B1 * | 8/2002 | Riaziat ................... | A61N 1/327 |
| | | | 604/65 |
| 6,522,911 B1 | 2/2003 | Toida et al. | |
| 6,551,613 B1 | 4/2003 | Dong et al. | |
| 6,689,142 B1 | 2/2004 | Tremaglio, Jr. et al. | |
| 7,713,239 B2 | 5/2010 | Uber, III et al. | |
| 7,758,871 B2 | 7/2010 | Donovan | |
| 7,846,465 B1 | 12/2010 | Keller et al. | |
| 8,133,201 B1 | 3/2012 | Hurtado | |
| 8,944,058 B2 | 2/2015 | Ging et al. | |
| 9,993,263 B2 * | 6/2018 | Esanu ................ | A61B 17/3417 |
| 2002/0103457 A1 | 8/2002 | Fontayne et al. | |
| 2003/0060763 A1 | 3/2003 | Penfold et al. | |
| 2003/0065578 A1 | 4/2003 | Peyrelevade et al. | |
| 2003/0216675 A1 | 11/2003 | Rooney | |
| 2004/0068037 A1 | 4/2004 | Mitadera et al. | |
| 2004/0078000 A1 | 4/2004 | Borchard et al. | |
| 2004/0153031 A1 | 8/2004 | Van Kaauwen | |
| 2004/0161435 A1 | 8/2004 | Gupta | |
| 2004/0225276 A1 | 11/2004 | Burgess | |
| 2004/0242976 A1 | 12/2004 | Abreu | |
| 2004/0260312 A1 * | 12/2004 | Magnusson ........ | A61B 17/3403 |
| | | | 606/130 |
| 2004/0267121 A1 * | 12/2004 | Sarvazyan ........... | A61B 5/4312 |
| | | | 600/439 |
| 2005/0075649 A1 * | 4/2005 | Bova ...................... | A61B 90/10 |
| | | | 606/130 |
| 2005/0137584 A1 | 6/2005 | Lemchen | |
| 2005/0148935 A1 | 7/2005 | Dimitrova et al. | |
| 2005/0159759 A1 | 7/2005 | Harbaugh et al. | |
| 2005/0240133 A1 | 10/2005 | Rooney | |
| 2006/0212044 A1 * | 9/2006 | Bova ...................... | A61B 90/10 |
| | | | 606/130 |
| 2006/0271025 A1 | 11/2006 | Jones et al. | |
| 2007/0243225 A1 | 10/2007 | McKay | |
| 2007/0260182 A1 | 11/2007 | Munday | |
| 2007/0276318 A1 | 11/2007 | Henley | |
| 2008/0044797 A1 | 2/2008 | Bardach et al. | |
| 2008/0166029 A1 | 7/2008 | Presura | |
| 2008/0171930 A1 * | 7/2008 | Abolfathi ............... | A61B 90/11 |
| | | | 600/410 |
| 2008/0237366 A1 | 10/2008 | Ehlert et al. | |
| 2008/0237367 A1 | 10/2008 | McNichols et al. | |
| 2008/0262376 A1 | 10/2008 | Price | |
| 2008/0262424 A1 * | 10/2008 | van't Hooft ......... | A61N 5/1027 |
| | | | 604/116 |
| 2008/0306392 A1 | 12/2008 | Satoguchi et al. | |
| 2009/0030338 A1 | 1/2009 | Crocker et al. | |
| 2009/0092948 A1 | 4/2009 | Gantes | |
| 2009/0234319 A1 * | 9/2009 | Marksteiner ............. | A61B 8/12 |
| | | | 604/506 |
| 2009/0234370 A1 | 9/2009 | Haras | |
| 2010/0015590 A1 | 1/2010 | Kiss | |
| 2010/0179473 A1 | 7/2010 | Genosar | |
| 2010/0256064 A1 | 10/2010 | Woolfson et al. | |
| 2010/0312100 A1 | 12/2010 | Zarkh et al. | |
| 2010/0326198 A1 | 12/2010 | Ribi | |
| 2011/0040280 A1 * | 2/2011 | Ijitsu ................. | A61M 5/31501 |
| | | | 604/506 |
| 2011/0046454 A1 * | 2/2011 | Ejlersen ............... | A61B 5/6848 |
| | | | 600/309 |
| 2011/0060309 A1 | 3/2011 | Lee et al. | |
| 2011/0112508 A1 | 5/2011 | Panzirer | |
| 2011/0118560 A1 | 5/2011 | Eckhoff et al. | |
| 2011/0118655 A1 | 5/2011 | Fassih et al. | |
| 2011/0129283 A1 | 6/2011 | Samain | |
| 2011/0178518 A1 | 7/2011 | Sohn | |
| 2011/0190787 A1 * | 8/2011 | Sahni ................... | A61B 19/201 |
| | | | 606/130 |
| 2011/0202032 A1 | 8/2011 | Shih et al. | |
| 2011/0228907 A1 | 9/2011 | Gagnon et al. | |
| 2011/0238038 A1 | 9/2011 | Sefi et al. | |
| 2011/0245951 A1 | 10/2011 | Gantes | |
| 2011/0257594 A1 * | 10/2011 | Lacoursiere ....... | A61B 10/0283 |
| | | | 604/117 |
| 2011/0295230 A1 | 12/2011 | O'Dea et al. | |
| 2012/0046668 A1 | 2/2012 | Gantes | |
| 2012/0100500 A1 | 4/2012 | Gao | |

(56) References Cited

U.S. PATENT DOCUMENTS

| | | | |
|---|---|---|---|
| 2012/0192330 A1 | 8/2012 | McMullen | |
| 2012/0203236 A1* | 8/2012 | Mamourian | A61B 17/3403 606/96 |
| 2012/0247474 A1 | 10/2012 | Torbenson | |
| 2012/0265187 A1 | 10/2012 | Palmer, III et al. | |
| 2012/0310155 A1 | 12/2012 | Heiser et al. | |
| 2013/0150714 A1 | 6/2013 | Howlett et al. | |
| 2013/0267850 A1* | 10/2013 | Berman | A61B 8/0825 600/443 |
| 2013/0274778 A1* | 10/2013 | Mercier | A61B 17/1739 606/172 |
| 2013/0341849 A1 | 12/2013 | Shimazaki et al. | |
| 2013/0345671 A1 | 12/2013 | Ryu et al. | |
| 2013/0345855 A1 | 12/2013 | Tsai et al. | |
| 2014/0005606 A1 | 1/2014 | Chen et al. | |
| 2014/0120505 A1 | 5/2014 | Rios et al. | |
| 2014/0121636 A1 | 5/2014 | Boyden et al. | |
| 2014/0121637 A1 | 5/2014 | Boyden et al. | |
| 2014/0212864 A1 | 7/2014 | Rios et al. | |
| 2014/0261430 A1 | 9/2014 | Davis | |
| 2014/0323907 A1* | 10/2014 | Frazier | A61M 5/00 600/562 |
| 2015/0027447 A1 | 1/2015 | Leevan et al. | |
| 2015/0055140 A1 | 2/2015 | Deguilio | |
| 2015/0157797 A1 | 6/2015 | Eggert et al. | |

OTHER PUBLICATIONS

Bain, Michael et al., "A Triangular Pattern for Botox Forehead Rejuvenation", Aesthetic Surgery Journal, Sep./Oct. 2006, pp. 617-619, The American Society for Aesthetic Plastic Surgery, Inc.

Bernardini, Fausto et al., "The 3D Model Acquisition Pipeline", Computer Graphics for um, 2002, pp. 149-172, vol. 21, No. 2, The Eurographics Association and Blackwell Publishers Ltd.

Bevilacqua, Alessandro et al., "Measuring Skin Topographic Structures through Capacitance Image Analysis", Proceedings of the IEEE International Conference on Video and Signal Based Surveillance (AVSS'06), 2006, pp. 1-5, IEEE.

Brandt, Fredric S. et al., "Hyaluronic acid gel fillers in the management of facial aging", Clinical Interventions in Aging, 2008, pp. 153-159, vol. 3, No. 1, 2008 Dove Medical Press Limited.

Buckley, Peter F. et al., "A Three-Dimensional Morphometric Study of Craniofacial Shape in Schizophrenia", Am J Psychiatry, Mar. 2005, pp. 606-608, vol. 162, No. 3.

Carruthers, Jean D. A. et al., "Advances in Facial Rejuvenation: Botulinum Toxin Type A, Hyaluronic Acid Dermal Fillers, and Combination Therapies—Consensus Recommendations", PRSJournal, Feb. 4, 2008, pp. 5S-30S, vol. 121, No. 5s, American Society of Plastic Surgeons.

Feng, Zhitiong et al., "Computer-assisted technique for the design and manufacture of realistic facial prostheses", British Journal of Oral and Maxillofacial Surgery, May 20, 2009, pp. 105-109, vol. 48, Elsevier Ltd.

Friedman, Paul M. et al., "3D In-Vivo Optical Skin Imaging for Topographical Quantitative Assessment of Non-Ablative Laser Technology", Dermatol Surg, Mar. 2002, pp. 199-204, vol. 28, No. 3, Blackwell Publishing, Inc.

Gwilliam, Jamie R. et al., "Reproducibility of soft tissue landmarks on three-dimensional facial scans", European Journal of Orthodontics, 2006, pp. 408-415, vol. 28, Oxford University Press.

Hanke, William C. et al., "Facial Soft-Tissue Fillers conference: Assessing the State of Science", Journal of the American Academy of Dermatology, Apr. 2011, pp. S66-S85.e136, vol. 64, No. 4, American Academy of Dermatology, Inc and American Society of Plastic Surgeons.

Jacobi, Ute et al., "In vivo determination of skin surface topography using an optical 3D device", Skin Research and Technology, 2004, pp. 207-214, vol. 10, Blackwell Munksgaard.

Kolb, Andreas et al., "Time-of-Flight Sensors in Computer Graphics", Computer Graphics Forum, Jun. 2009, pp. 1-16.

Kundu, Suriti et al., "Principles of Office Anesthesia: Part II. Topical Anesthesia", American Family Physician, Jul. 1, 2002, pp. 99-102, vol. 66, No. 1, American Academy of Family Physicians.

Lapatki, Bernd G. et al., "Topographical Characteristics of Motor Units of the Lower Facial Musculature Revealed by Means of High-Density Surface Emg", Journal of Neurophysiology, Jan. 2006, pp. 342-354, vol. 95, American Physiological Society.

Levenberg, Alex "Clinical experience with a TriPollar™ radiofrequency system for facial and body aesthetic treatments", Eur J Dermatol, Sep.-Oct. 2010, pp. 615-619, vol. 20, No. 5.

Majid, Z. et al., "Integration of stereophotogrammetry and triangulation-based laser scanning system for precise mapping of craniofacial morphology", The International Archives of the Photogrammetry, Remote Sensing and Spatial Information Sciences, 2008, pp. 805-812, vol. 37, Part B5, Beijing.

Markiewicz, Michael R. et al., "The Use of 3D Imaging Tools in Facial Plastic Surgery", Facial Plast Surg Clin N Am, 2011, pp. 655-682, vol. 19, Elsevier Inc.

McCleane, Gary, "Topical application of analgesics: a clinical option in day case anaesthesia?", Current Opinion in Anesthesiology, 2010, pp. 704-707, vol. 23, Lippincott Williams & Wilkins.

Meier, Jason D. et al., "Autologous Fat Grafting—Long-term Evidence of Its Efficacy in Midfacial Rejuvenation", Arch Facial Plast Surg, Jan./Feb. 2009, pp. 24-28, vol. 11, No. 1, American Medical Association.

Park, Juwan et al., "Profile of Xeomin® (incobotulinumtoxinA) for the treatment of blepharospasm", Clinical Ophthalmology, 2011, pp. 725-732, vol. 5, Dove Medical Press Ltd.

PCT International Search Report; International App. No. PCT/US2013/053604; dated Feb. 21, 2014; pp. 1-4.

PCT International Search Report; International App. No. PCT/US2013/067029; dated Mar. 18, 2014; pp. 1-2.

Prager, Welf et al., "A prospective, rater-blind, randomized comparison of the effectiveness and tolerability of Belotero® Basic versus Restylane® for correction of nasolabial folds", Eur J Dermatol, Nov.-Dec. 2010, pp. 748-752, vol. 20, No. 6.

Rozman, Branka et al., "Temperature-Sensitive Microemulsion Gel: An Effective Topical Delivery System for Simultaneous Delivery of Vitamins C and E", AAPS PharmSciTech, Mar. 2009, pp. 54-61, vol. 10, No. 1, American Association of Pharmaceutical Scientists.

Seitz, Hermann et al., "Three-Dimensional Printing of Porous Ceramic Scaffolds for Bone Tissue Engineering", Wiley InterScience, 2005, pp. 782-788, Wiley Periodicals, Inc.

Sherman, Richard N., "Avoiding dermal filler complications", Clinics in Dermatology, 2009, pp. S23-S32, vol. 27, Elsevier Inc.

Slepushkin, Vladimir A. et al., "Sterically Stabilized pH-sensitive Liposomes—Intracellular Delivery of Aqueous Contents and Prolonged Circulation In Vivo", The Journal of Biological Chemistry, Jan. 24, 1997, pp. 2382-2388, vol. 272, No. 4, The American Society for Biochemistry and Molecular Biology, Inc.

Sun, Chengzhi et al., "An Enhanced Active Shape Model for Facial Features Extraction", 2008 11$^{th}$ IEEE International Conference on Communication Technology Proceedings, 2008, pp. 661-664, 2008 IEEE.

Van Heerbeek, Niels et al., "Three dimensional measurement of rhinoplasty results", Rhinology, 2009, p. 121-125, vol. 47.

Wa, Chrystal V. et al., "Mapping the human face: biophysical properties", Skin Research and Technology, 2010, pp. 38-54, vol. 16, John Wiley & Sons A/S.

Wieringa, F. P. et al., "Remote Non-invasive Stereoscopic Imaging of Blood Vessels: First In-vivo Results of a New Multispectral Contrast Enhancement Technology", Annals of Biomedical Engineering, Dec. 2006, pp. 1870-1878, vol. 34, No. 12, Biomedical Engineering Society.

Wolff, Erin et al., "Skin wrinkles and rigidity in early postmenopausal women vary by race/ethnicity: baseline characteristics of the skin ancillary study of the keeps trial" Fertil Steril, Feb. 2011, pp. 1-12, vol. 95, No. 2.

Yavlovich, Amichai et al., "Light-sensitive Lipid-based Nanoparticles for Drug Delivery: Design Principles and Future Considerations for Biological Applications", Mol Membr Biol, Oct. 2010, pp. 1-26, vol. 27, No. 7.

(56) References Cited

OTHER PUBLICATIONS

Zheng, Zhong-Long et al., "Enhanced Active Shape Model for Facial Feature Localization", Proceedings of the Seventh International Conference on Machine Learning and Cybernetics, Jul. 12-15, 2008, pp. 2841-2845, IEEE.
European Patent Office, extended European Search Report, Pursuant to Rule 62 EPC; App. No. EP 13828529.1; dated May 2, 2016; pp. 1-6.
Ciocca et al.; "Computer-aided design and manufacturing construction of a surgical template for craniofacial implant positioning to support a definitive nasal prosthesis"; Clin. Oral Impl. Res. 22. 2011; Aug. 5, 2010; pp. 850-856; John Wiley & Sons 2010.
Zhang et al; "Design and fabrication of MEMS-based microneedle arrays for medical applications"; Microsyst Technol; May 20, 2009; pp. 1073-1082; vol. 15; Springer.

\* cited by examiner

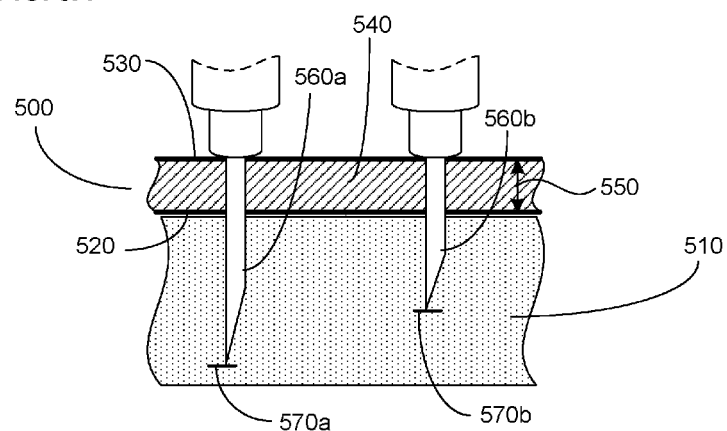
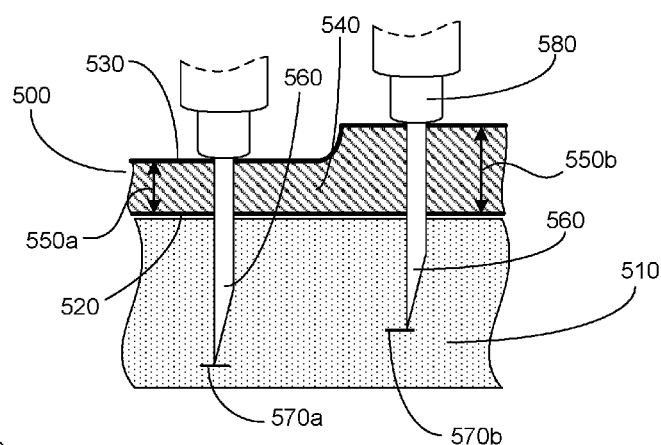
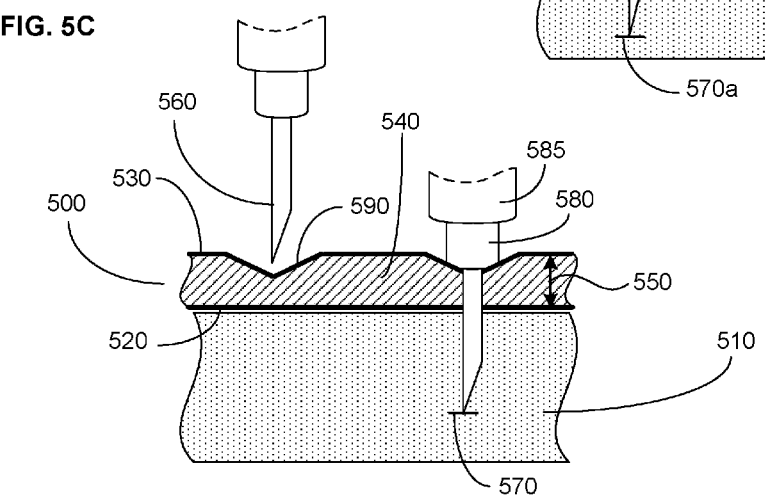

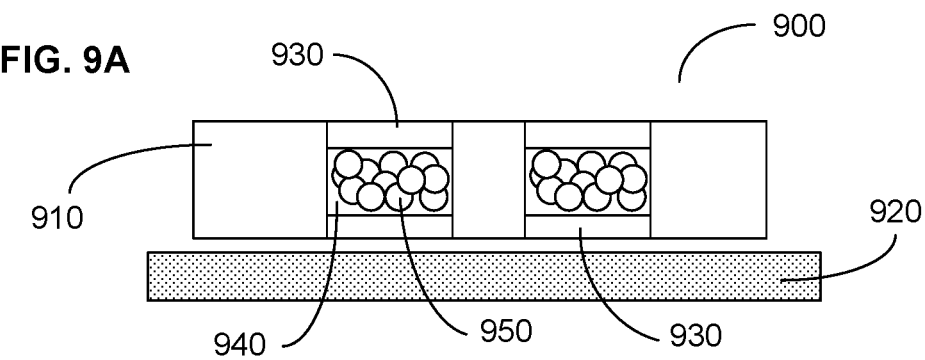
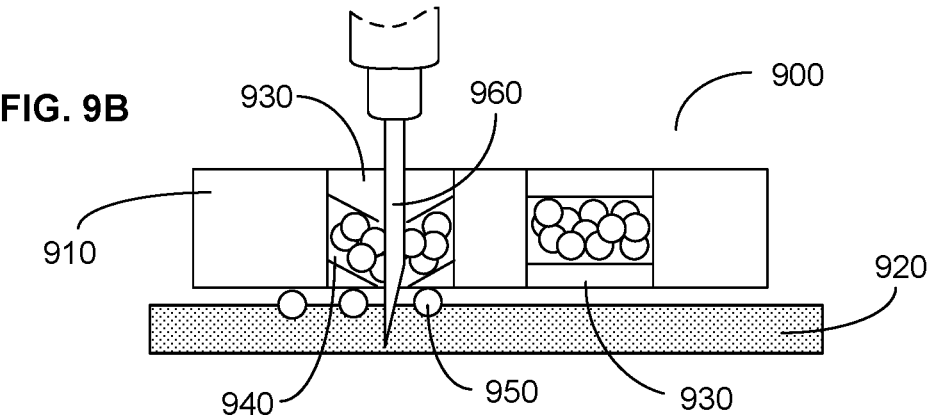
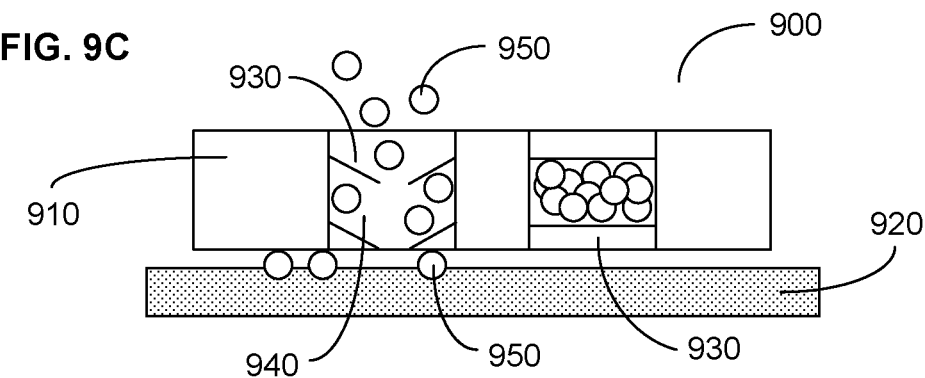

FIG. 13

1300
Inserting one or more injection needles through one or more injection needle access regions of a wearable injection guide, the wearable injection guide constructed of a rigid material formed to substantially conform in shape to a topography of a body region of an individual, the one or more injection needle access regions arranged in a treatment pattern 1310
Injecting at least one injectable agent through the one or more injection needles into an underlying tissue of the body region of the individual

FIG. 14

1300
Inserting one or more injection needles through one or more injection needle access regions of a wearable injection guide, the wearable injection guide constructed of a rigid material formed to substantially conform in shape to a topography of a body region of an individual, the one or more injection needle access regions arranged in a treatment pattern 1400
Inserting the one or more injection needles through the one or more injection needle access regions at a 90 degree angle relative to the underlying tissue of the body region of the individual.

1410
Inserting the one or more injection needles through the one or more injection needle access regions at less than a 90 degree angle relative to the underlying tissue of the body region of the individual.

1310
Injecting at least one injectable agent through the one or more injection needles into an underlying tissue of the body region of the individual

FIG. 17

1300
Inserting one or more injection needles through one or more injection needle access regions of a wearable injection guide, the wearable injection guide constructed of a rigid material formed to substantially conform in shape to a topography of a body region of an individual, the one or more injection needle access regions arranged in a treatment pattern

1310
Injecting at least one injectable agent through the one or more injection needles into an underlying tissue of the body region of the individual > 1700
> Injecting the at least one injectable agent through the one or more injection needles into one or more of epidermis, papillary dermis, reticular dermis, subcutis, or muscle of the underlying tissue of the body region of the individual > 1710
> Injecting the at least one injectable agent through the one or more injection needles into the underlying tissue of one or more of a forehead, a glabella, a periorbital region, an auricular region, an ear, a cheek, a lip, a nasolabial fold, a labial region, a perilabial region, a sublabial region, a labiomental crease, or a neck region of the individual.

FIG. 20

2000
Aligning one or more alignment marks of a wearable injection guide with one or more reference points on a body region of an individual, the wearable injection guide including a rigid needle-penetrable material with an inner surface and an outer surface, the inner surface having a form fitting contour substantially conforming to the topography of the body region of the individual and the outer surface having one or more fiducials indicative of at least one treatment parameter 2010
Immobilizing the wearable injection guide on the body region of the individual 2020
Inserting one or more injection needles through the rigid needle-penetrable material of the wearable injection guide at or near the one or more fiducials 2030
Injecting at least one injectable agent through the one or more injection needles into an underlying tissue of the body region of the individual

FIG. 22

2000
Aligning one or more alignment marks of a wearable injection guide with one or more reference points on a body region of an individual, the wearable injection guide including a rigid needle-penetrable material with an inner surface and an outer surface, the inner surface having a form fitting contour substantially conforming to the topography of the body region of the individual and the outer surface having one or more fiducials indicative of at least one treatment parameter 2200
Aligning the one or more alignment marks of the wearable injection guide with one or more topographical landmarks on the body region of the individual 2210
Aligning the one or more alignment marks of the wearable injection guide with one or more pigmentation, pigmented area, skin texture pattern, tattoo, blemish, scar, anatomical feature, or subsurface blood vessel of at least a potion of the body region of the individual 2010
Immobilizing the wearable injection guide on the body region of the individual 2020
Inserting one or more injection needles through the rigid needle-penetrable material of the wearable injection guide at or near the one or more fiducials 2030
Injecting at least one injectable agent through the one or more injection needle into an underlying tissue of the body region of the individual

FIG. 25

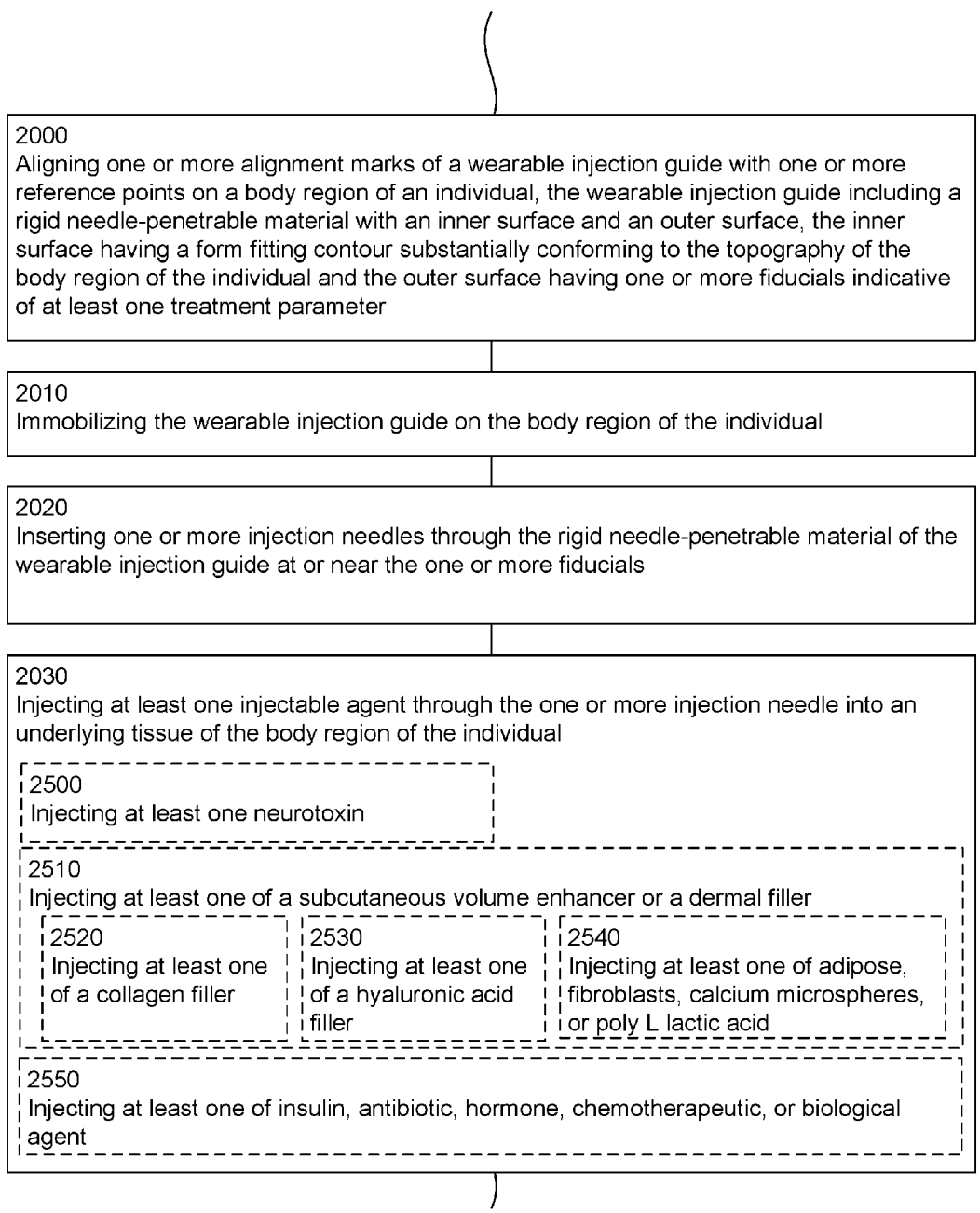

2000
Aligning one or more alignment marks of a wearable injection guide with one or more reference points on a body region of an individual, the wearable injection guide including a rigid needle-penetrable material with an inner surface and an outer surface, the inner surface having a form fitting contour substantially conforming to the topography of the body region of the individual and the outer surface having one or more fiducials indicative of at least one treatment parameter 2010
Immobilizing the wearable injection guide on the body region of the individual 2020
Inserting one or more injection needles through the rigid needle-penetrable material of the wearable injection guide at or near the one or more fiducials 2030
Injecting at least one injectable agent through the one or more injection needle into an underlying tissue of the body region of the individual 2500
Injecting at least one neurotoxin 2510
Injecting at least one of a subcutaneous volume enhancer or a dermal filler 2520
Injecting at least one of a collagen filler 2530
Injecting at least one of a hyaluronic acid filler 2540
Injecting at least one of adipose, fibroblasts, calcium microspheres, or poly L lactic acid 2550
Injecting at least one of insulin, antibiotic, hormone, chemotherapeutic, or biological agent

4300 An article of manufacture

> 4310
> Non-transitory machine readable media bearing one or more instructions for generating a wearable injection guide for administering an injectable agent to an individual, the one or more instructions including:
>
>> 4320
>> One or more instructions for controlling acquisition of one or more digital images of a body region of the individual with at least one image capture device
>
>> 4330
>> One or more instructions for receiving one or more output signals having information associated with the one or more digital images of the body region acquired by the at least one image capture device
>
>> 4340
>> One or more instructions for creating a digitally-rendered model of the wearable injection guide from the one or more digital images of the body region of the individual
>
>> 4350
>> One or more instructions for generating a treatment regimen for the individual based on the one or more digital images of the body region
>
>> 4360
>> One of more instructions for adding one or more digitally rendered fiducials indicative of at least one treatment parameter of the treatment regimen to the digitally rendered model of the wearable injection guide
>
>> 4370
>> One or more instructions for generating one or more model output signals having information for manufacturing the wearable injection guide from the digitally rendered model of the wearable injection guide

SYSTEMS AND METHODS FOR WEARABLE INJECTION GUIDES

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

PRIORITY APPLICATIONS

The present application constitutes a continuation of U.S. patent application Ser. No. 13/568,033, entitled SYSTEMS AND METHODS FOR WEARABLE INJECTION GUIDES, naming Mahalaxmi Gita Bangera, Edward S. Boyden, Hon Wah Chin, Gregory J. Della Rocca, Daniel Hawkins, Roderick A. Hyde, Muriel Y. Ishikawa, Jordin T. Kare, Robert Langer, Eric C. Leuthardt, Stephen L. Malaska, Terence Myckatyn, Parag Jitendra Parikh, Dennis J. Rivet, Joshua S. Shimony, Michael A. Smith, Elizabeth A. Sweeney, Clarence T. Tegreene, Sharon L. Wolda, Lowell L. Wood, Jr. as inventors, filed 6 Aug. 2012, which is currently co-pending or is an application of which a currently co-pending application is entitled to the benefit of the filing date, and which is a continuation-in-part of U.S. patent application Ser. No. 13/567,921, entitled DEVICES AND METHODS FOR WEARABLE INJECTION GUIDES, naming Mahalaxmi Gita Bangera, Edward S. Boyden, Gregory J. Della Rocca, Daniel Hawkins, Roderick A. Hyde, Muriel Y. Ishikawa, Jordin T. Kare, Robert Langer, Eric C. Leuthardt, Stephen L. Malaska, Terence Myckatyn, Parag Jitendra Parikh, Dennis J. Rivet, Joshua S. Shimony, Michael A. Smith, Elizabeth A. Sweeney, Clarence T. Tegreene, Sharon L. Wolda, Lowell L. Wood, Jr. as inventors, filed 6 Aug. 2012.

The present application constitutes a continuation of U.S. patent application Ser. No. 13/568,033, entitled SYSTEMS AND METHODS FOR WEARABLE INJECTION GUIDES, naming Mahalaxmi Gita Bangera, Hon Wah Chin, Roderick A. Hyde, Muriel Y. Ishikawa, Jordin T. Kare, Eric C. Leuthardt, Stephen L. Malaska, Elizabeth A. Sweeney, Sharon L. Wolda, and Lowell L. Wood, Jr. as inventors, filed 6 Aug. 2012, which is currently co-pending or is an application of which a currently co-pending application is entitled to the benefit of the filing date, and which is a continuation-in-part of U.S. patent application Ser. No. 13/567,995, entitled DEVICES AND METHODS FOR WEARABLE INJECTION GUIDES, naming Mahalaxmi Gita Bangera, Hon Wah Chin, Roderick A. Hyde, Muriel Y. Ishikawa, Jordin T. Kare, Eric C. Leuthardt, Stephen L. Malaska, Elizabeth A. Sweeney, Sharon L. Wolda, and Lowell L. Wood, Jr. as inventors, filed 6 Aug. 2012.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

In an aspect, a wearable injection guide includes, but is not limited to: a rigid material formed to substantially conform in shape to a topography of a body region of an individual, the rigid material substantially impenetrable to an injection needle, and the rigid material including one or more injection needle access regions arranged in a treatment pattern. In addition to the foregoing, other device aspects are described in the claims, drawings, and text forming a part of the present disclosure.

In an aspect, a method of administering an injection treatment to a skin region includes, but is not limited to: inserting one or more injection needles through one or injection needle access regions of a wearable injection guide, the wearable injection guide constructed of a rigid material formed to substantially conform in shape to a topography of a body region of an individual, the one or more injection needle access regions arranged in a treatment pattern; and injecting at least one injectable agent through the one or more injection needles into an underlying tissue of the body region of the individual. In addition to the foregoing, other method aspects are described in the claims, drawings, and text forming a part of the present disclosure.

In an aspect, a wearable injection guide includes, but is not limited to: a rigid material substantially impenetrable to an injection needle, the rigid material including one or more injection needle access regions arranged in a treatment pattern, the one or more injection needle access regions including one or more activatable injection event indicators. In addition to the foregoing, other device aspects are described in the claims, drawings, and text forming a part of the present disclosure.

In an aspect, a wearable injection guide includes, but is not limited to: a rigid needle-penetrable material having an inner surface and an outer surface, the inner surface having form-fitting contours substantially conforming to a topography of a body region of an individual and the outer surface including one or more fiducials indicative of at least one treatment parameter. In addition to the foregoing, other device aspects are described in the claims, drawings, and text forming a part of the present disclosure.

In an aspect, a method of administering an injection treatment to an individual includes, but is not limited to: aligning one or more alignment marks of a wearable injection guide with one or more reference points on a body region of an individual, the wearable injection guide including a rigid needle-penetrable material with an inner surface and an outer surface, the inner surface having a form fitting contour substantially conforming to the topography of the body region of the individual and the outer surface having one or more fiducials indicative of at least one treatment parameter; immobilizing the wearable injection guide on the body region of the individual; inserting one or more injection needles through the rigid needle-penetrable material of the wearable injection guide at or near the one or more fiducials; and injecting at least one injectable agent through the one or more injection needles into an underlying tissue of the body region of the individual. In addition to the foregoing, other method aspects are described in the claims, drawings, and text forming a part of the present disclosure.

In an aspect, a wearable injection guide includes, but is not limited to: a needle-penetrable material having an inner surface, an outer surface, and one or more activatable injection event indicators, the inner surface having form-fitting contours substantially conforming to a topography of a body region of an individual and the outer surface including one or more fiducials indicative of at least one treatment parameter. In addition to the foregoing, other device aspects are described in the claims, drawings, and text forming a part of the present disclosure.

In an aspect, a method of generating a wearable injection guide for an individual includes, but is not limited to: acquiring one or more digital images of a body region of the individual; creating a digitally rendered model of the wearable injection guide from the one or more digital images of the body region of the individual; adding one or more digitally rendered fiducials indicative of at least one treatment parameter to the digitally rendered model of the wearable injection guide; and forming the wearable injection guide from the digitally rendered model of the wearable injection guide, the formed wearable injection guide including one or more fiducials indicative of the at least one treatment parameter, the one or more fiducials corresponding to the one or more digitally rendered fiducials on the digitally rendered model of the wearable injection guide. In addition to the foregoing, other method aspects are described in the claims, drawings, and text forming a part of the present disclosure.

In an aspect, a method of generating a wearable injection guide for an individual includes, but is not limited to: acquiring one or more digital images of a body region of the individual; creating a digitally rendered model of the wearable injection guide from the one or more digital images of the body region of the individuals; adding one or more digitally rendered injection needle access regions in a treatment pattern to the digitally rendered model of the wearable injection guide; and forming the wearable injection guide from the digitally rendered model of the wearable injection guide, the formed wearable injection guide including one or more injection needle access regions, the one or more injection needle access regions corresponding to the one or more digitally rendered injection needle access regions on the digitally rendered model of the wearable injection guide. In addition to the foregoing, other method aspects are described in the claims, drawings, and text forming a part of the present disclosure.

In an aspect, a method of generating a wearable injection guide for an individual includes, but is not limited to: acquiring one or more digital images of a body region of the individual; creating a digitally rendered three-dimensional surface model of the body region; developing a treatment regimen specific to the individual based on analysis of the digitally rendered three-dimensional surface model of the body region of the individual; adding one or more digitally rendered fiducials indicative of at least one treatment parameter to the digitally rendered three-dimensional surface model of the body region, the at least one treatment parameter a component of the treatment regimen specific to the individual; and printing the one or more digitally rendered fiducials indicative of the at one treatment parameter onto a surface of a preformed wearable injection guide, the preformed wearable injection guide configured to cover at least a portion of the body region of the individual. In addition to the foregoing, other method aspects are described in the claims, drawings, and text forming a part of the present disclosure.

In an aspect, a system for generating a wearable injection guide for an individual includes, but is not limited to: at least one image capture device configured to acquire one or more digital images of a body region of an individual and to transmit one or more output signals having information associated with the one or more digital images; a computing device operably linked to the at least one image capture device including non-transitory machine readable media bearing one or more instructions for generating the wearable injection guide from the one or more digital images of the body region of the individual, the one or more instructions including one or more instructions for controlling one or more functions of the at least one image capture device; one or more instructions for receiving the one or more output signals having information associated with the one or more digital images from the at least one image capture device; one or more instructions for creating a digitally rendered model of the wearable injection guide from the one or more digital images of the body region of the individual; one or more instructions for adding one or more fiducials indicative of at least one treatment parameter to the digitally rendered model of the wearable injection guide; and one or more instructions for generating one or more model output signals having information for forming the wearable injection guide from the digitally rendered model of the wearable injection guide; and a manufacturing device configured to receive the one or more model output signals from the computing device and to form the wearable injection guide from the digitally rendered model of the wearable injection guide, the formed wearable injection guide including one or more fiducials indicative of the at least one treatment parameter, the one or more fiducials corresponding to the one or more digitally rendered fiducials on the digitally rendered model of the wearable injection guide. In addition to the foregoing, other system aspects are described in the claims, drawings, and text forming a part of the present disclosure.

In an aspect, an article of manufacture includes, but is not limited to: non-transitory machine readable media bearing one or more instructions for generating a wearable injection guide for administering an injectable agent to an individual, the one or more instructions including: one or more instructions for controlling acquisition of one or more digital images of a body region of the individual with at least one image capture device; one or more instructions for receiving one or more output signals having information associated with the one or more digital images from the at least one image capture device; one or more instructions for creating a digitally rendered model of the wearable injection guide from the one or more digital images of the body region of the individual; one or more instructions for generating a treatment regimen for the individual based on the one or more digital images of the body region; one or more instructions for adding one or more digitally rendered fiducials indicative of at least one treatment parameter of the treatment regimen to the digitally rendered model of the wearable injection guide; and one or more instructions for generating one or more model output signals having information for manufacturing the wearable injection guide from the digitally rendered model of the wearable injection guide. In addition to the foregoing, other article of manufacture aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 5A is a schematic of a cross-section through a wearable injection guide with one or more injection needles.

FIG. 5B is a schematic of a cross-section through a wearable injection guide with one or more injection needles.

FIG. 5C is a schematic of a cross-section through a wearable injection guide with one or more injection needles.

FIG. 9A is a schematic of a cross-section through a wearable injection guide prior to insertion of an injection needle.

FIG. 9B is a schematic of a cross-section through a wearable injection guide during insertion of an injection needle.

FIG. 9C is a schematic of a cross-section through a wearable injection guide after insertion of an injection needle.

FIG. 13 is a flowchart of a method of administering an injection treatment.

FIG. 14 is a flowchart illustrating aspects of a method such as shown in FIG. 13.

FIG. 17 is a flowchart illustrating aspects of a method such as shown in FIG. 13.

FIG. 20 is a flowchart of a method of administering an injection treatment.

FIG. 22 is a flowchart showing aspects of a method such as depicted in FIG. 20.

FIG. 25 is a flowchart showing aspects of a method such as depicted in FIG. 20.

FIG. 43 is a schematic of an article of manufacture.

DETAILED DESCRIPTION

Figure 1A:
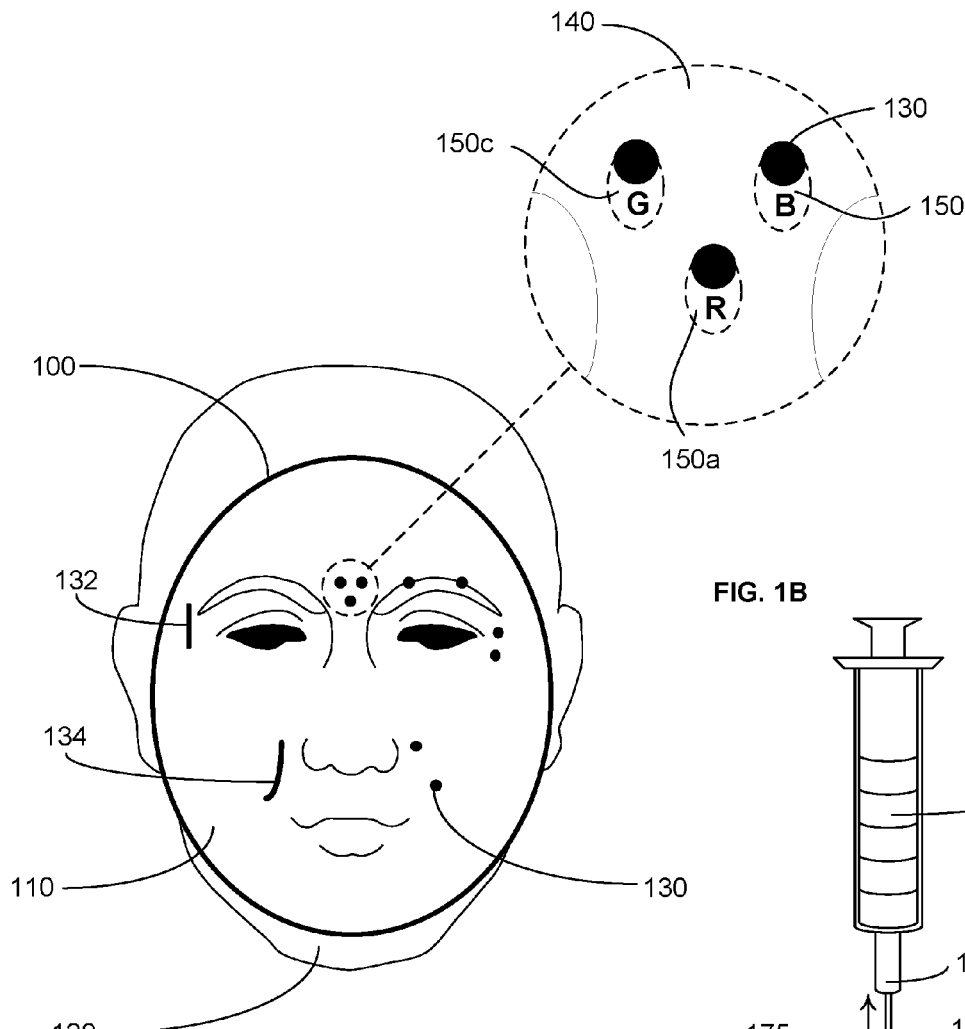
FIG. 1A is a schematic of a wearable injection guide on a face of an individual.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here.

A wearable injection guide is described for guiding injection of one or more injection needles containing at least one injectable agent into a body region of an individual for treatment of one or more conditions. A wearable injection guide can be configured for deployment on any of a number of body regions of an individual including but not limited to the face, torso, abdomen, head, neck, upper extremity, lower, extremity, buttocks, or any other body region assessable for needle injection. A wearable injection guide can be used for guiding injection of injectable agents used to treat any of a number of conditions including but not limited to a cosmetic condition (e.g., wrinkles, sagging skin), pain (e.g., migraine), neurological disorders (e.g., idiopathic neuropathy), neuromuscular disorder (e.g., cervical dystonia, blepharospasm), inflammation (e.g., arthritis, psoriasis), vascular disorder (e.g., varicose veins, rosacea, Reynaud's Syndrome), cancer, infection (e.g., bacterial or viral infection), endocrine condition, metabolic condition (e.g., diabetes), infertility (e.g., ovulatory stimulation for in vitro fertilization), or vitamin deficiency (e.g., vitamin B deficiency). The at least one injectable agent can include any of a number of injectable agents including but not limited to neurotoxins, subcutaneous volume enhancers, dermal fillers, insulin, antibiotics, hormones, chemotherapeutic, or biological agents.

With reference to FIG. 1, shown is a schematic view of a wearable injection guide 100 on a face of an individual. Wearable injection guide 100 includes rigid material 110 formed to substantially conform in shape to a topography of a body region of an individual, e.g., the face 120. In this non-limiting example, wearable injection guide 100 covers almost the entirety of the individual's face. In some embodiments, the rigid material 110 of the wearable injection guide 100 may be designed to cover less than the entirety of a body region. For example, a wearable injection guide for use in guiding injection of injectable agents into an individual's face may cover one or more of the forehead, eyes, cheeks or mouth, depending upon the treatment regimen. For example, a wearable injection guide for use in cosmetically treating frown lines of the forehead or crow's feet near the eyes may include rigid material covering only the forehead and eyes of an individual's face.

The rigid material 110 of the wearable injection guide 100 may be formed from one or more materials substantially impenetrable to an injection needle. The one or more material substantially impenetrable to an injection needle can include one or more material capable of being shaped, molded or printed to form the wearable injection guide 100. Non-limiting examples of shapeable, moldable or printable materials include acrylic, nylon, plastic, ceramic, resin, rubber, epoxy, thermoplastic, photopolymer, polyurethane, silicone, or latex. In some embodiments, all or part of the rigid material is transparent, to allow a physician, other practitioner, or the individual to see through the wearable injection guide to the underlying surface of the body region. The shapeable, moldable or printable materials may be further hardened into a material substantially impenetrable to an injection needle using one or more stimuli. In some embodiments, the shapeable, moldable or printable materials may simply harden over an elapsed time period or by exposure to ambient air. In some embodiments, the shapeable, moldable or printable material may be hardened in response to electromagnetic energy, e.g., light of a specific wavelength, or in response to elevated temperature.

The wearable injection guide 100 may be formed from shapeable, moldable, or printable materials by a variety of manufacturing methods. In some embodiments, the wearable injection guide 100 is generated from a mold made of the body region of the individual. For example, a mold of a body region of an individual can be generated by covering the body region, e.g., an individual's face, with a material that hardens to conform in shape to a topography of the body region. For example, alginate may be used in combination with plaster bandages to create a mold of a body region of an individual, e.g., the individual's face. In some embodiments, the mold itself can be used as a preformed wearable injection guide. Non-limiting examples of materials that can be used for generating a mold of a body region of an individual include modeling clay, plaster, alginate, or combinations thereof. In some embodiments, the mold can be a reusable template for forming one or more wearable injection guides with a material, e.g., latex, that is poured or spread into the mold, hardened, and removed from the mold.

In some embodiments, the wearable injection guide 100 is formed using digitized information, e.g., digital images, regarding the topography of the body region of an individual in combination with a manufacturing method. The topography of the body region can include both the micro-topography of the skin surface, e.g., skin texture and patterning, as well as the topography of body features, e.g., cheeks, nose, lips, eye sockets, joints, and the like. In some embodiments, a computing device is used to generate a digitally rendered model of the wearable injection guide based on the one or more digital images of the body region of the individual. Information regarding the digitally-rendered model of the wearable injection guide is sent to a manufacturing device which produces the wearable injection guide based on the received information. Non-limiting examples of methods for generating a three-dimensional structure from digitized information include stereolithography, laser sintering, fused deposition modeling, polyjet, three-dimensional printing, vacuum casting, reaction injection molding, or injection molding.

Returning to FIG. 1, the wearable injection guide 100 includes one or more injection needle access regions 130 arranged in a treatment pattern 140. The one or more injection needle access regions 130 are configured to allow an injection needle to pass through the rigid material 110 of the wearable injection guide 100 to the underlying tissue of the body region of the individual's face 120. In some embodiments, the one or more injection needle access regions are configured to allow injection needles to only pass through wearable injection guide 100 in a prescribed treatment pattern at the injection needle access regions 130. In some embodiments, the one or more injection needle access regions 130 are configured to allow an injection needle to readily pass through an otherwise needle-impenetrable rigid material 110. In some embodiments, at least one of the one or more injection needle access regions includes a diameter greater than an injection needle diameter. In some embodiments, the one or more injection needle access regions 130 include one or more portions of the rigid material 110 having a reduced thickness sufficient to permit an injection needle penetration. In some embodiments, the one or more injection needle access regions 130 include one or more portions of the rigid material 110 having a reduced hardness sufficient to permit an injection needle penetration. The material in the one or more injection needle access regions 130 can be the same material as rigid material 110, but it may be treated, processed, or cured differently to generate the access regions. In some embodiments, the material in the one or more injection needle access regions 130 can be the same material used in rigid material 110 but is thinner or softer in the access regions. In an embodiment, the material in the one or more injection needle access regions 130 can be different from rigid material 110 of wearable injection guide 100. In some embodiments, at least a portion of the rigid material is transparent proximal to or coincident with at least one of the one or more injection needle access regions.

In some embodiments, rigid material 110 can define one or more injection needle access regions 130 that are one or more openings in rigid material 110. The one or more injection needle access regions 130 including one or more openings defined by the rigid material can have a cross-section of any desired diameter. In some embodiments, the one or more openings defined by the rigid material have a diameter greater than an injection needle diameter. For example, the one or more injection needle access regions 130 including one or more openings defined by the rigid material can be sized to allow injection needles of a specified diameter, e.g., gauge, to pass through the wearable injection guide 100 and into the underlying tissue of the body region. The gauge of an injection needle is inversely proportional to its outer diameter. For example, the injection needle access regions 130 can range in a cross-sectional diameter from about 5 millimeters (mm) to about 0.2 mm, to accommodate standard needle gauges that range from 7 gauge (outer diameter approximately 4.6 mm) to 34 gauge (outer diameter approximately 0.19 mm). In an embodiment, the one or more injection needle access regions range in diameter from about 0.8 mm to about 0.3 mm to accommodate needles ranging in size from 21 gauge to 32 gauge, which are injection needle gauges commonly used to inject agents into the skin. Larger needles, i.e., needles with a larger diameter but a smaller gauge number, are associated with increased pain. Smaller needles, i.e., needles with smaller diameter but larger gauge number, are less painful but are less able to accommodate viscous injectable agents.

In some embodiments, the one or more injection needle access regions 130 of the wearable injection guide 100 are round in shape. However, the shape of the one or more injection needle access regions 130 is not restricted to being circular in shape and can include, for example, oval, square, rectangular, trapezoid or triangular shapes (for non-circular shapes, the term "diameter" as used herein refers to the largest diameter of a cylindrical injection needle that is able to pass through the opening). In general, the shape of the one or more injection needle access regions 130 is shaped to allow passage of an appropriately sized injection needle through the rigid material 110 of the wearable injection guide 100 and into the underlying tissue of the body region. The diameter of the one or more injection needle access regions 130 can be designed to permit the passage of the needle therethrough with very little gap between the injection needle and the rigid material 110. This is useful for injections that require precise placement of the injection needle into the underlying tissue. In an embodiment, the diameter of the one or more injection needle access regions 130 openings can be designed to permit the passage of the injection needle therethrough with a relatively large gap between the injection needle and the rigid material 110. This is useful for injections that can accommodate injection needle placement in a more general or gross area of the underlying tissue, where accurate placement of the injection needle is not as important.

In some embodiments, the one or more injection needle access regions are linear in shape, e.g., a line. One or more injection needle access regions that are linear in shape can accommodate serial needle sticks or linear threading along the path of the linear shape. As illustrated in FIG. 1, in some embodiments, the one or more injection needle access regions can be one or more straight slits 132 in the wearable injection guide. In some embodiments, the one or more injection needle access regions can be one or more curved slits 134 in the wearable injection guide. The one or more straight slits 132 and/or curved slits 134 can be continuous or discontinuous depending upon the preferred treatment pattern. In some embodiments, the one or more straight slits 132 and/or curved slits 134 represent portions of rigid material 110 having reduced thickness or hardness sufficient to permit an injection needle penetration. In some embodiments, the one or more straight slits 132 and/or curved slits 134 represent portions of rigid material 110 defining one or more openings.

In some embodiments, the wearable injection guide 100 includes one or more injection needle access regions 130 comprising one or more areas of the rigid material 110 having a reduced thickness sufficient to permit an injection needle penetration. The reduction in thickness of the rigid material in the injection needle access region can be about 0.1% to about 100%. For example, a wearable injection guide can be formed in which the thickness of the rigid material within the injection needle access region is about 1-10% of the overall thickness of the rigid material. The reduction in thickness of the rigid material within the injection needle access regions can be added to a digitally rendered model of the wearable injection guide and incorporated into the formed wearable injection guide during manufacture.

In some embodiments, the wearable injection guide 100 includes one or more injection needle access regions 130 comprising one or more areas of rigid material 110 having reduced hardness to permit an injection needle penetration. The reduction in hardness of the rigid material in the injection needle access region can be about 0.1% to about 100%. For example, a wearable injection guide can be formed in which the hardness of the rigid material within the injection needle access region is about 1-10% of the overall hardness of the rigid material. In some instances, the injection needle access regions can include a different material than that used for the overall wearable injection guide. For example, the wearable injection guide 100 can be formed from acrylic and the injection needle access regions formed from a soft rubber or latex. In some instances, the injection needle access regions can include the same material that is used for the bulk of the rigid material of the wearable injection guide, but treated, e.g., cured, differently from the rest of the rigid material.

The wearable injection guide 100 includes one or more injection needle access regions 130 arranged in a treatment pattern 140. In some embodiments, the one or more injection needle access regions 130 are arranged in a treatment pattern 140 that is predetermined. For example, the treatment pattern may be predetermined depending upon the type of injectable agent and/or the condition being treated. For example, cosmetic treatment of a portion of the face, e.g., the glabella frown lines, may follow a predetermined pattern of injection sites. In some embodiments, the predetermined treatment pattern is provided by a computing device that stores treatment patterns specific for a condition or specific for an injectable agent. In some embodiments, the one or more injection needle access regions arranged in a treatment pattern can be included in a digitally rendered model of the wearable injection guide. For example, the one or more injection needle access regions 130 may be arranged in a treatment pattern 140 based on the specific needs of the individual for whom the wearable injection guide is designed and manufactured. In this case, the number and placement of the one or more injection needle access regions are specifically prescribed for the individual.

In some embodiments, the one or more injection needle access regions 130 can be arranged in a treatment pattern 140 that is generic for a given treatment regimen. For example, the treatment pattern 140 can be a series of rows and/or columns of injection needle access regions, any one or more of which may be accessed during the course of treatment.

In some embodiments, the treatment pattern 140 is anatomical feature dependent. For example, a wearable injection guide designed for deployment on the face of an individual may have a treatment pattern dependent upon a particular anatomical feature of the face, e.g., the eye brow, the glabella, or cheek folds. In some embodiments, the anatomical feature can include an anatomical feature that might be contraindicated as an injection site, e.g., an underlying blood vessel, joint, or inside the orbit of the eye, and as such the one or more injection needle access regions are arranged in a treatment pattern to avoid this anatomical feature. In some embodiments, the anatomical features of the body region are fairly uniform, e.g., the anatomical features of the upper thigh, and as such the arrangement of the one or more injection needle access regions into a treatment pattern can be more generic or less specific to the individual.

In some embodiments, the arrangement of one or more injection needle access regions 130 into a treatment pattern 140 is dependent upon the specific needs of the individual. In the case of a wearable injection guide deployed on an individual's face for cosmetic use, for example, the arrangement of the one or more injection needle access regions into a treatment pattern can include situating the one or more injection needle access regions over, for example, one or more lines, wrinkles, folds, or pouches in need of treatment on the individual's face. The skin is composed of three layers: the outer epidermis, the dermis, and the subcutis (hypodermis) or lowest layer of the skin. The dermis can be further divided into the upper papillary region and the lower reticular region. During youth, elastin and collagen contained in the dermis allows the epidermis to stretch and hold large amounts of moisture. Over time, elastin and collagen are lost from the dermis and the skin becomes thinner and less elastic and stretchy. In addition, the dermis begins to have difficulty moving adequate amounts of moisture up to the epidermis, causing the epidermis to sag and wrinkles to form. During aging, mechanical lines also begin to appear and are commonly associated with squinting, e.g., crow's feet, smiling, e.g., laugh lines, or frowning, e.g., forehead frown lines. In some embodiments, the treatment pattern on the wearable injection guide can include one or more injection needle access regions situated over one or more horizontal forehead lines, glabellar frown lines, periorbital lines, preauricular lines, cheek lines, nasolabial folds, upper radial lip lines, lower radial lip lines, corner of the mouth lines, marionette lines, labiomental crease, and/or horizontal neck folds.

In some embodiments, a wearable injection guide 100 deployed on an individual's face 120 can include one or more injection needle access regions 130 arranged in a treatment pattern 140 that are situated over one or more muscles associated with creating lines and wrinkles on the individual's face 120. For example, the treatment pattern on the wearable injection guide can include one or more injection needle access regions situated over one or more of the occipito-frontalis muscle of the forehead for treatment of horizontal forehead wrinkles; the procerus muscle between the eyebrows for treatment of horizontal wrinkling above the bridge of the nose; the corrugators muscle for treatment of the "11" wrinkles that appear between the eyebrows or in the glabella during an angry facial expression; the orbicularis oculi muscles around the eyes for the treatment of "crow's feet;" the nasalis muscles of the nose for the treatment of "bunny lines" along the side of the nose; the orbicularis oris muscles around the lips for the treatment of radial pucker lines on the lips; and the depressor anguli oris muscles under the lips for the treatment of down turning of the corners of the mouth while frowning.

In some embodiments, the treatment pattern 140 can include one or more injection needle access regions 130 arranged in such a way as to create volume upon injection of a filler substance. For example, a series of injection needle access regions can be arranged on a wearable injection guide in a linear treatment pattern along a skin fold. In another example, the injection needle access regions can be arranged on a wearable injection guide in a square treatment pattern to facilitate threading of an injectable agent in a crisscross pattern.

Returning to the example in FIG. 1, the one or more injection needle access regions 130 of the wearable injection guide 100 arranged in a treatment pattern 140 can further include one or more fiducials, e.g., 150a, 150b, and 150c, indicative of at least one treatment parameter. In some embodiments, the one or more fiducials indicative of at least one treatment parameter mark the site at which an injection needle is intended to be inserted through the wearable injection guide. In some embodiments, the one or more fiducials indicative of at least one treatment parameter provide instructions as to what action should be taken at or near any of the one or more fiducials, e.g., what injectable agent to inject, the dose of the injectable agent, and/or how deep to insert a needle into the underlying tissue of the body region.

In some embodiments, at least one of the one or more fiducials indicative of the at least one treatment parameter is positioned proximal to at least one of the one or more injection needle access regions. For example, an injection needle access region that is an opening in the rigid material of the wearable injection guide may include one or more fiducials in proximity to the opening that indicate at least one treatment parameter relevant to that opening. In some embodiments, at least one of the one or more fiducials indicative of the at least one treatment parameter coincides with at least one of the one or more injection needle access regions. For example, the one or more fiducials may coincide with a portion of the rigid material that has reduced thickness or hardness corresponding to an injection needle access region.

In some embodiments, each of the one or more injection needle access regions include one or more fiducials indicative of at least one treatment parameter. In some embodiments, only a subset of the one or more injection needle access regions include one or more fiducials indicative of at least one treatment parameter. In some embodiments, the one or more fiducials indicative of at least one treatment parameter are generic and appropriate for use for anyone undergoing treatment for a specific condition. In some embodiments, the one or more fiducials indicative of at least one treatment parameter are specific to the individual for whom the wearable injection guide is designed and manufactured. For example, the type of injectable agent and/or dosage may be based on the specific condition of the individual as well as other criteria, e.g., weight, age, skin thickness, allergic response, or other physiological criteria relevant to administration of an injectable agent.

In some embodiments, the at least one treatment parameter is part of a treatment regimen indicated for treatment of a specific condition. The treatment regimen can include one or more injectable agents, dosing of the one or more injectable agents, timing of dosing of each of the one or more injectable agents, sequence of dosing of each of the one or more injectable agents, placement of dosing of each of the one or more injectable agents. For example, the treatment regimen may be represented by one or more fiducials indicating the time intervals at which an injectable agent should be repeatedly injected through the wearable injection guide at the same or different injection needle access region over a period of time, e.g., over the course of a 30 to 60 minute office visit. When two or more injectable agents are indicated for use in the condition, the treatment regimen may be represented by one or more fiducials indicative of the sequence of injection of the two or more injectable agents.

The one or more fiducials can include one or more colors, numbers, letters, shapes, crosshairs, or combinations thereof indicative of at least one treatment parameter. In the non-limiting example of FIG. 1, the one or more fiducials 150a, 150b, and 150c are depicted as being red (R), blue (B) and green (G), respectively, but it is understood that the one or more fiducials can include any combination of colors, numbers, letters, shapes, and/or crosshairs indicative of at least one treatment parameter.

In an embodiment, the one or more fiducials 150a, 150b, and 150c indicative of at least one treatment parameter include one or more fiducials 150a, 150b, and 150c indicative of at least one type of injectable agent to be injected at at least one of the one or more injection needle access regions. For example, a cosmetic treatment of the face can include one or more fiducials indicative of at least one injectable agent, e.g., a neurotoxin, subcutaneous volume enhancer, or dermal filler (see, e.g., Carruthers et al., *Plast. Reconstr. Surg.* (2008) 121 (Suppl):5S-30S, which is incorporated herein by reference). Non-limiting examples of other injectable agents include insulin, antibiotics, hormones, chemotherapeutics or biological agents. In an embodiment, the one or more fiducials 150a, 150b, and 150c indicative of at least one treatment parameter can include one or more fiducials 150a, 150b, and 150c indicative of at least one dosage of at least one injectable agent to be injected at at least one of the one or more injection needle access regions. The dosage of the injectable agent can include one or more units or parts thereof, one or more milliliters or parts thereof, or one or more other measures of dosage. For example, the neurotoxin onabotulinumtoxinA (BOTOX®) is typically injected in 3-5 unit increments per injection. The dosage can also include timing and sequence of injection of the injectable agent. For example, an injectable agent may be injected multiple times over the course of hours, days, or weeks. For example, a treatment regimen may include two or more injectable agents and each of two or more injectable agents may be injected in a preferred or prescribed sequence.

In an embodiment, the one or more fiducials 150a, 150b, and 150c indicative of at least one treatment parameter match a specific injectable agent, e.g., a red fiducial for a neurotoxin, a blue fiducial for a subcutaneous volume enhancer, and a green fiducial for a dermal filler. In an embodiment, the one or more fiducials 150a, 150b, and 150c indicative of at least one treatment parameter match a dose of a specific injectable agent, e.g., a red fiducial equals 5 units, a blue fiducial equals 10 units, and a green fiducial equals 15 units.

Figure 1B:
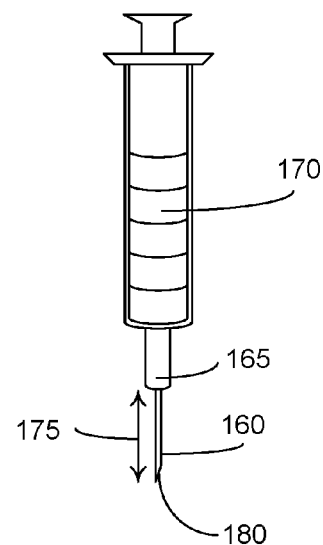
FIG. 1B is a schematic of an injection needle.

In some embodiments, the one or more fiducials 150a, 150b, and 150c indicative of at least one treatment parameter are indicative of at least one needle injection depth of at least one type of injectable agent to be injected at at least one of the one or more injection needle access regions. In some embodiments, the one or more needle injection depth is dependent upon the length of the injection needle. FIG. 1B illustrates a diagram of a typical injection needle 160 attached via a needle hub 165 to a syringe 170. The length 175 of the injection needle 160 or needle shank is the length of the injection needle 160 as measured from the needle hub 165 at the proximal end of the injection needle 160 to the tip of the bevel 180 at the distal end of the injection needle 160. The bevel 180 is the slanted portion of the injection needle 160 that creates a sharp, pointed tip. The length 175 of the injection needle 160 can be measured in inches or mm. In some embodiments, the length 175 of the injection needle 160 can vary from about 4 mm (5/32 inches) to about 12.7 mm (½ inches). Injection needles of shorter or longer length, e.g., up to about 50 mm (2 inches) or more can also be contemplated for use with the wearable injection guide.

In some embodiments, the rigid material 110 of the wearable injection guide includes a needle depth-limiting surface proximate to or at least partially coincident with at least one of the one or more injection needle access regions. In some embodiments, the needle depth-limiting surface is defined as the distance or thickness between an inner and outer surface of the rigid material of the wearable injection guide. For example, the rigid material can have a thickness that limits the depth to which an injection needle can be injected. For example, a rigid material that is 2 mm thick at an injection needle access region will allow a 4 mm needle to reach, at most, an injection depth of 2 mm. In some embodiments, the rigid material can have a uniform thickness throughout the wearable injection guide, including at the one or more injection needle access regions. In some embodiments, the rigid material may vary in thickness and may vary in thickness specifically at the one or more injection needle access regions. For example, the thickness may be 3 mm at one injection needle access region and 2 mm at a second injection needle access region, thereby permitting a 4 mm injection needle to penetrate the skin no more than 1 mm and 2 mm at the respective injection sites. The wearable injection guide 100 can vary in thickness across a single surface according to design and purpose, and can range from about 0.1 mm to about 25 mm or more.

In some embodiments, the depth to which the injection needle penetrates in to the underlying tissue of the body region of an individual is dependent upon whether or not the injection needle is inserted to a stop point defined by the needle hub bumping up against the outer surface of the wearable injection guide. In the instance where the injection needle is inserted all the way to a stop point, the depth to which the injection needle penetrates into the underlying tissue of the body region will be dependent upon the thickness of the wearable injection guide, the thickness of the injection needle access region itself, and/or the length of the injection needle. The one or more fiducials on the wearable injection guide related to needle injection depth can include information related to the preferred type of needle for use at a given injection needle access region and whether the preferred injection needle needs to be injected to a stop point as defined, for example, by the needle hub.

In some embodiments, the wearable injection guide includes at least one needle-penetrable membrane covering at least a portion of at least one surface of the rigid material. In some embodiments, the at least one needle-penetrable membrane serves as a needle-depth limiting surface, limiting the depth to which an injection needle can be inserted through the one or more injection needle access regions, e.g., openings in the rigid material, and into the underlying tissue.

In some embodiments, the wearable injection guide 100 can be used in conjunction with one or more depth-limiting adapters. The one or more depth-limiting adapters are configured to limit the depth to which an injection needle can be injected into the skin tissue of an individual. In an embodiment, a depth-limiting adapter can be configured as a tube with an inner diameter sufficient to accommodate passage of an injection needle of a specific gauge and a length sufficient to limit the depth to which an injection needle can be injected into the underlying tissue of the body region of the individual. The inner diameter can range from about 5 mm to about 0.2 mm. In an embodiment, the inner diameter of the depth-limiting adaptor can range from about 0.8 mm to about 0.3 mm to accommodate an injection needle ranging in size from 21 to 32 gauge, which are injection needle gauges commonly used for injecting agents tissue. The inner diameter of the depth-limiting adapter can also be sufficiently small to allow insertion of the injection needle up to but not including the hub of the needle. For example, a depth-limiting adapter of about 5 mm in length would allow a needle of about 12.7 mm in length to be injected to a stop point defined by the needle hub and to reach a skin depth of about 7.7 mm if used alone or to a skin depth of about 4.7 mm if used in conjunction with a wearable injection guide with a thickness of about 3 mm. In some embodiments, the one or more depth-limiting adapters can have a shape, e.g., a diameter, to facilitate at least partial insertion of the depth-limiting adapter into at least one of the one or more injection needle access regions. For example, the depth-limiting adapter can be a hollow cylinder with an outer diameter that is configured for insertion into an injection needle access region that is an opening defined by the rigid material of the wearable injection guide. The one or more depth-limiting adapters can range in length from about 1 mm to about 25 mm or more. In some embodiments, the depth-limiting adapter is telescoping, allowing for adjustment of the length of the depth-limiting adapter and consequently the depth to which an injection needle can be injected into an underlying tissue.

In some embodiments, the one or more injection needle access regions 130 arranged in a treatment pattern 140 are incorporated into the wearable injection guide 100 at the time of manufacture. In some embodiments, the one or more fiducials, e.g., 150a, 150b, and 150c, indicative of at least one treatment parameter specific to the individual are also incorporated into the wearable injection guide 100 at the time of manufacture. For example, the digitized image of the body region, e.g., an individual's face 120, can be incorporated into a digitally rendered model of a wearable injection guide intended for three-dimensional printing and can include the one or more injection needle access regions, indicating the injection sites as well as the one or more fiducials e.g., 150a, 150b, and 150c, indicative of the at least one treatment parameter.

In some embodiments, the one or more injection needle access regions 130 are incorporated into the wearable injection guide 100 at the time of manufacture, but the one or more fiducials indicative of at least one treatment parameter, e.g., the actual sites and/or treatment parameter intended for injection on a given treatment day, can be marked on the wearable injection guide after the wearable injection guide has been manufactured. For example, the treating physician, other practitioner, or the individual themselves (in the case of self-injection) can place the one or more fiducials indicative of at least one treatment parameter on the wearable injection guide using a pen or other marking device at the prescribed injection sites.

In some embodiments, the wearable injection guide is used by a physician or other practitioner to guide injection of injectable agents into a patient. In some embodiments, the wearable injection guide is used by an individual to guide self-injection of an injectable agent.

Figure 2:
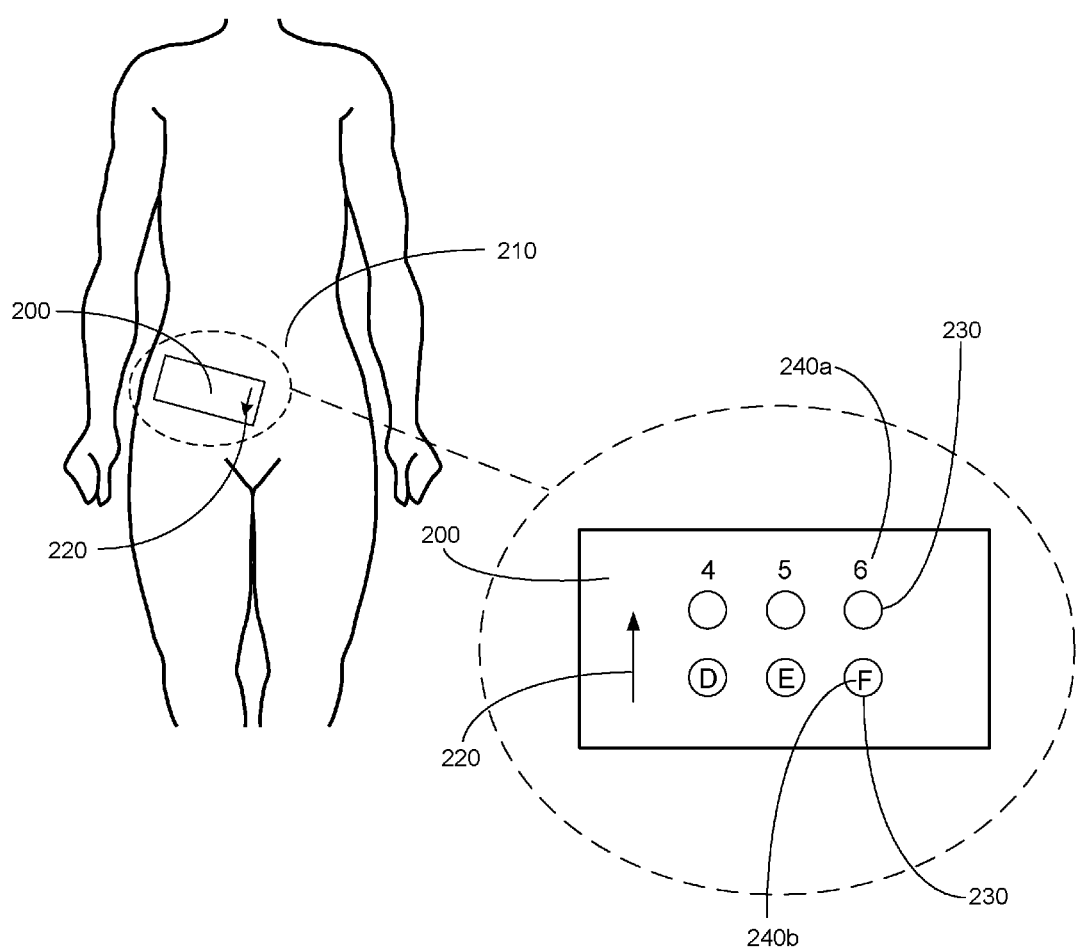
FIG. 2 is a schematic of a wearable injection guide on an abdominal region of an individual.

The wearable injection guide can be configured for placement on a body region of the individual including, but not limited to, the face, the torso, the abdomen, the neck, the head, the upper extremities, the lower extremities, the buttocks, or any other body region of the individual accessible to injection. FIG. 2 is a non-limiting embodiment that illustrates a wearable injection guide 200 for use on body on the lower abdomen of an individual. The wearable injection guide 200 includes one or more injection needle access regions 230. The one or more injection needle access regions 230 are annotated with one or more fiducials 240a or 240b indicative of at least one treatment parameter and can include one or more of colors, numbers, letters, shapes, crosshairs, or combinations thereof. In some embodiments, the one or more injection needle access regions 230 can be annotated with one or more fiducials 240a that are positioned proximal to the one or more injection needle access regions 230. In some embodiments, the one or more injection needle access regions 230 can be annotated with one or more fiducials 240b that are coincident with or superimposed on the one or more injection needle access regions 230. The one or more treatment parameters indicated by the one or more fiducials can include one or more of a type of injectable agent, a dosage of the injectable agent and/or a needle injection depth.

In some embodiments the wearable injection guide 200 is configured for use by the individual for self-injection of an injectable agent. Non-limiting examples of injectable agents for self-injection include antibiotics, insulin, fertility hormones (e.g., FSH, ganirelix, cetrotide, Lupron, HCG), immunomodulators (e.g., etanercept), glatiramer (injected daily to treat multiple sclerosis), teriparatide (injected daily to treat osteoporosis), enoxaparin (injected daily to treat deep vein thrombosis), vitamins (e.g., vitamin B12). In some embodiments, the wearable injection guide 200 may have an orientation as indicated by an orientation indicium 220 that allows an individual to decipher the one or more fiducials 240a and 240b, e.g., letters and/or numbers, on the wearable injection guide 200 when it is deployed on the individual's abdomen 210 but would otherwise appear upside-down to another person viewing the wearable injection guide 200 on said individual's abdomen 210.

Figure 3A:
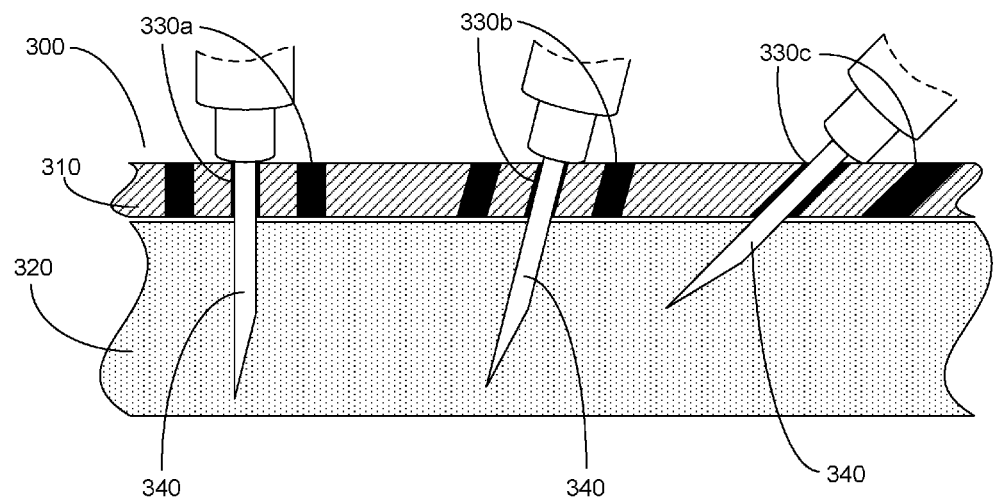
FIG. 3A is a schematic of a cross-section through a wearable injection guide on a body region.
Figure 3B:
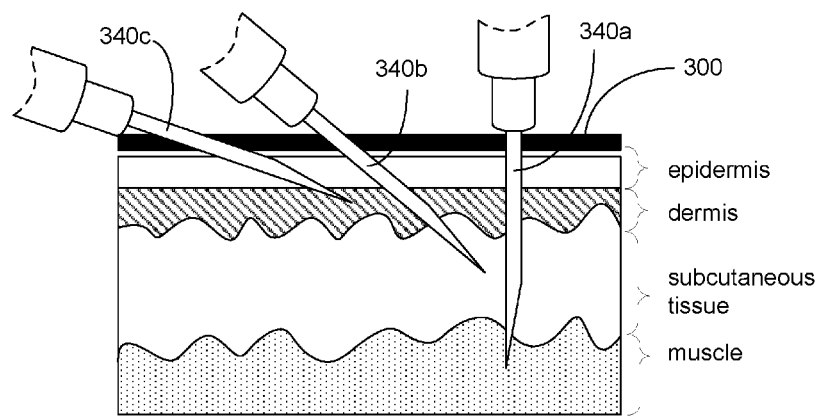
FIG. 3B is a schematic of a cross-section through a wearable injection guide and tissue layers.

FIGS. 3A and 3B depict further aspects of some embodiments of a wearable injection guide including one or more injection needle access regions that allow one or more injection needles to pass through the rigid material at various angles and into the underlying tissue of the body region of the individual. FIG. 3A is a cross-sectional view through wearable injection guide 300 and depicts an injection needle 340 passing through the rigid material 310 of the wearable injection guide 300 at various angles and into the underlying tissue of the body region 320 of an individual. In some embodiments, the one or more injection needle access regions 330a transect the rigid material 310 at an angle of 90 degrees relative to an adjacent surface of the rigid material 310. As such, injection needle 340 is able to pass through the wearable injection guide 300 and into the underlying tissue of the body region 320 of the individual at a 90 degree angle relative to the surface of the wearable injection guide 300. In this manner, the injection needle 340 can be injected straight into the underlying tissue of the body region 320 of an individual to a preferred depth. In some embodiments, the one or more injection needle access regions transect the rigid material at an angle of less than 90 degrees relative to an adjacent surface of the rigid material. For example, one or more injection needle access regions 330b can be configured to allow an injection needle 340 to pass through the wearable injection guide 300 and into an underlying tissue of the body region 320 of the individual at an angle of about 60 degrees. In another example, one or more injection needle access regions 330c can be configured to allow an injection needle 340 to pass through the wearable injection guide 300 and into an underlying tissue of the body region 320 of the individual at an angle of about 30 degrees. The one or more injection needle access regions, e.g., one or more areas of the rigid material 310 defining one or more openings, one or more portions of the rigid material having a reduced hardness, and/or one or more portions of the rigid material having a reduced thickness, can be configured to allow an injection needle 340 to pass through the wearable injection guide 300 and into the underlying tissue of the body region 320 of the individual at an angle ranging from greater than 0 degrees and less than or equal to 90 degrees.

The angle of the one or more injection needle access regions, e.g., 330a, 330b and/or 330c, through the rigid material 310 of the wearable injection guide 300 can be dependent on the injectable agent and the desired depth of the needle injection into the underlying tissue of the body region 320 of the individual and the desired pattern of injection. For example, as illustrated in FIG. 3B, injections into the muscle, i.e., intramuscular injection, may be done with an injection needle 340a through the wearable injection guide 300 at a 90 degree angle; injections into the subcutis, i.e, subcutaneous injection, may be done with an injection needle 340b through the wearable injection guide 300 at a 45 degree angle; and injections into the epidermis or dermis may be done with an injection needle 340c through the wearable injection guide 300 at a 10 to 15 degree angle.

In some embodiments, the wearable injection guide comprises a rigid needle-penetrable material having an inner surface and an outer surface, the inner surface having form-fitting contours substantially conforming to the topography of a body region of an individual and the outer surface having one or more fiducials indicative of at least one treatment parameter.

Figure 4:
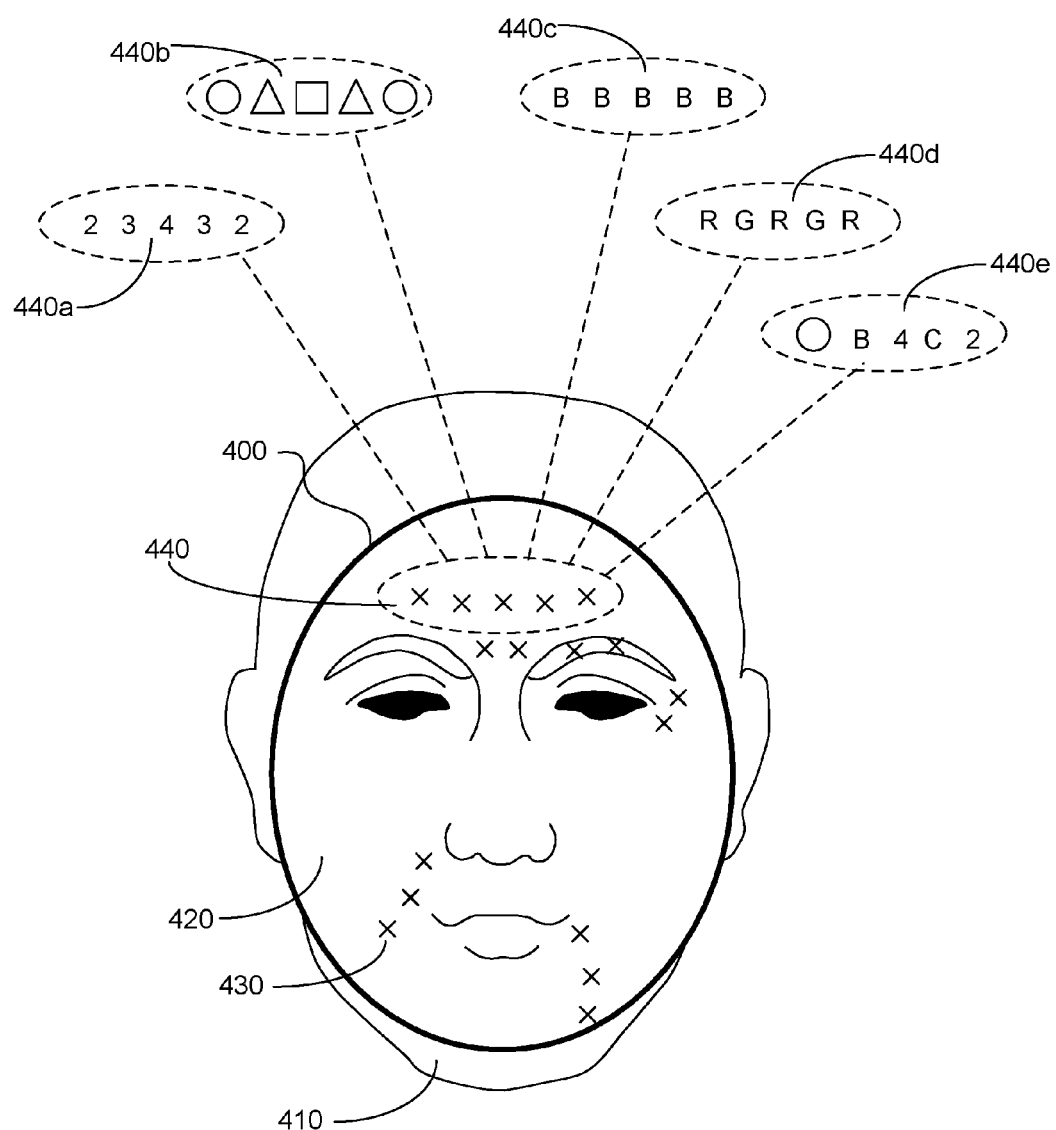
FIG. 4 is a schematic of a wearable injection guide on a face of an individual.

FIG. 4 illustrates a non-limiting embodiment of a wearable injection guide 400 deployed on the body region 410 of an individual. The wearable injection guide 400 formed from one or more rigid needle-penetrable materials has an outer surface 420 including one or more fiducials 430 indicative of at least one treatment parameter. The one or more fiducials indicative of at least one treatment parameter include one or more shapes, colors, numbers, letters, crosshairs, or combinations thereof. Non-limiting examples of the at least one treatment parameter include at least one type of injectable agent to be injected at said one or more fiducials, at least one dosage amount of an injectable agent to be injected at said one or more fiducials, at least one angle of injection of the injection needle to be injected at said one or more fiducials, or at least one needle injection depth of at least one type of injectable agent to be injected at said one or more fiducials. In some embodiments, the one or more treatment parameters are part of a treatment regimen. In some embodiments, the treatment regimen is specific to the individual. In some embodiments, at least a portion of the rigid needle-penetrable material is transparent at at least one of a location proximal to or coincident with the one or more fiducials. For example, the rigid material may be transparent in a portion of the wearable injection guide including one or more fiducials such that an underlying treatment area on the body region of the individual is visible through the wearable injection guide.

Returning to FIG. 4, in some embodiments, the one or more fiducials 430 indicative of at least one treatment parameter are arranged in a treatment pattern 440 on the outer surface 420 of the wearable injection guide 400. The one or more fiducials arranged in a treatment pattern can include one or more shapes, colors, numbers, letters, crosshairs, or combinations thereof arranged in a treatment pattern. FIG. 4 illustrates various embodiments of one or more fiducials arranged in a treatment pattern including treatment pattern 440a including one or more numbers, treatment pattern 440b including one or more shapes, treatment pattern 440c including one or more letters, treatment pattern 440d including one or more colors, or treatment pattern 440e including combinations of numbers, shapes, letters, and colors.

In some embodiments, the one or more fiducials 430 are merely indicative of where an injection needle should be inserted through the wearable injection guide. For example, the wearable injection guide may be designed for use with one specific injectable agent with one specific injection dose and one specific needle depth such that the only variable indicated by the one or more fiducials, e.g., crosshairs, is the actual site of injection. In some embodiments, any given injection site may include a first fiducial indicating the injection site and at least one second fiducial indicating one or more treatment parameters for said associated injection site. In some embodiments, a first set of fiducials are used to indicate the treatment parameters while a second set of fiducials are used to indicate the injection sites, the first set of fiducials not necessarily proximal to or coincident with the injection sites. For example, the first set of fiducials may be distributed along an edge of the wearable injection guide and providing treatment parameter information, e.g., injection information, for a second set of fiducials arranged in treatment pattern on the wearable injection guide.

In some embodiments, the one or more fiducials 430 are indicative of the presence of one or more agents incorporated into wearable injection guide 400, either in or on the inner surface of the wearable injection guide 400 or in at least one agent-containing reservoir associated with the wearable injection guide. The one or more agents can include one or more analgesics, disinfectants, antiseptics, sterilants, therapeutic agents or combinations thereof.

In some embodiments, the one or more fiducials 430 indicative of at least one treatment parameter and arranged in a treatment pattern 440 are arranged in one or more predetermined treatment patterns. For example, the treatment pattern of the one or more fiducials may be predetermined depending upon the type of injectable agent and/or the condition being treated. For example, cosmetic treatment of a portion of the face, e.g., the glabella frown lines, may follow a predetermined pattern of injection sites. In some embodiments, the predetermined treatment pattern of one or more fiducials is provided by a computing device that stores treatment patterns specific for a condition, specific for an injectable agent, and/or specific for the individual. For example, one or more digitally rendered fiducials indicative of the one or more fiducials can be incorporated into a digitally rendered model of the wearable injection guide in a predetermined treatment pattern and subsequently incorporated into a formed wearable injection guide during a manufacturing process, e.g., three-dimensional printing.

In some embodiments, the one or more fiducials 430 can be placed onto wearable injection guide 400 by a physician or other practitioner at some point after the guide is formed but prior to treatment. In an embodiment, the one or more fiducials can be manually placed on the wearable injection guide by an individual at some point after the guide is formed but prior to self-injection treatment. The one or more fiducials are placed onto the wearable injection guide based on the desired treatment parameters. In some embodiments the one or more fiducials are placed on the wearable injection guide by the physician, other practitioner, or the individual in a predetermined treatment pattern based on one or more of the condition, the injectable agent or specific topography and/or anatomical features of the individual. In this manner, multiple personalized wearable injection guides can be generated at one time for a particular individual and the treatment options for a given treatment period, e.g., a given treatment day or office visit, can be marked on the wearable injection guide at the time of treatment, providing flexibility in the treatment regimen.

In some embodiments, the arrangement of one or more fiducials 430 in a treatment pattern 440 on the wearable injection guide 400 is dependent upon the specific needs of the individual. In some embodiments, the one or more fiducials are arranged in a treatment pattern that coincides with a treatment area on the body region of the individual. For example, in the case of a wearable injection guide 400 deployed on an individual's face, the arrangement of the one or more fiducials 430 in a treatment pattern 440 can include one or more fiducials 430 situated over or proximal to one or more lines, wrinkles, folds, or pouches in need of treatment on the body region 410 of the individual. For example, a wearable injection guide can include one or more fiducials arranged in a treatment pattern which when deployed on the individual's face are situated over or proximal to lines, wrinkles, folds, or pouches associated with a forehead, a glabella, a periorbital region, an auricular region, an ear, a lip, a cheek, a nasolabial fold, a labial region, a perilabial region, a sublabial region, a labiomental crease, or a neck region of the individual.

In some embodiments, the treatment pattern 440 includes one or more fiducials 430 situated over one or more muscles associated with creating lines and/or wrinkles on the body region 410 of the individual. For example, in treating an individual's face, the wearable injection guide can include one or more fiducials arranged in a treatment pattern that are situated over or proximal to one or more of the occipitofrontalis muscle of the forehead for treatment of horizontal forehead wrinkles; the procerus muscle between the eyebrows for treatment of horizontal wrinkling above the bridge of the nose; the corrugators muscle for treatment of the "11" wrinkles that appear between the eyebrows or glabella during an angry facial expression; the orbicularis oculi muscles around the eyes for the treatment of "crow's feet;" the nasalis muscles of the nose for the treatment of "bunny lines" along the side of the nose; the orbicularis oris muscles around the lips for the treatment of radial pucker lines on the lips; and the depressor anguli oris muscles under the lips for the treatment of down turning of the corners of the mouth while frowning.

In some embodiments, the treatment pattern 440 can include one or more fiducials 430 arranged in a treatment pattern so as to avoid portions of the underlying tissue of the body region that might be contraindicated for administration of the injectable agent. For example, the one or more fiducials on the wearable injection guide may be arranged so as to avoid injection of an injectable agent into an underlying blood vessel. Other non-limiting examples of contraindicated injection sites include areas of infection, skin disease or inflammation (unless the injectable agent is being used to treat said conditions) or areas too close to the orbits (to prevent ptosis). In another example, the one or more fiducials may be arranged in a treatment pattern so as to avoid injection of an injectable agent into a site that has been previously injected.

FIGS. 5A-5C illustrate further non-limiting embodiments of a wearable injection guide. FIGS. 5A, 5B, and 5C are cross-sectional views of wearable injection guide 500 deployed on body region 510 of an individual. The wearable injection guide 500 includes an inner surface 520 and an outer surface 530 separated by a rigid needle-penetrable material 540. The rigid needle-penetrable material 540 can include one or more of acrylic, nylon, plastic, ceramic, resin, rubber, epoxy, thermoplastic, photopolymer, polyurethane, latex, or silicone. In some embodiments, at least a portion of the rigid needle-penetrable material 540 is transparent.

The inner surface 520 of wearable injection guide 500 includes form-fitting contours substantially conforming to a topography of a body region 510 of an individual. In some embodiments, the inner surface 520 includes form-fitting contours substantially conforming to the topography of one or more of the individual's facial region, torso region, abdominal region, head region, neck region, upper extremity, lower extremity, buttocks, or any other body region accessible for injection. In an embodiment, the inner surface 520 can include form-fitting contours substantially conforming to the topography of one or more regions of the individual's face including but not limited to an individual's forehead region, eye region, cheek region, mouth region, or combinations thereof. The portion of the body region 510 covered by the wearable injection guide 500 can be dependent upon the desired treatment location. For example, the wearable injection guide 500 can include an inner surface 520 with form-fitting contours substantially conforming to the combined forehead and eye regions of the individual for treatment of lines and/or wrinkles around the forehead and eyes. In another example, the wearable injection guide 500 can include an inner surface 520 with form-fitting contours substantially conforming to a body region associated with an individual's upper thigh or lower abdominal region.

The outer surface 530 of the wearable injection guide 500 is configured to limit the depth to which an injection needle is capable of penetrating the underlying tissue of the body region 510. In some embodiments, the outer surface of the rigid needle-penetrable material includes an outer contour with one or more portions separated from the inner surface of the rigid needle-penetrable material by at least one needle depth-limiting distance. In some embodiments, the needle-depth-limiting distance is about 0.5 mm to about 25 mm. In some embodiments, a needle depth-limiting distance is equivalent to a thickness of the rigid material of the wearable injection guide. For example, outer surface 530 has a contour defined by one or more needle depth-limiting distance 550 of rigid needle-penetrable material 540 separating the outer surface 530 from the inner surface 520 of the wearable injection guide 500. In some embodiments, as illustrated in FIG. 5A, the outer surface 530 has a uniform contour defined by needle depth-limiting distance 550 of rigid needle-penetrable material 540 separating the outer surface 530 from the inner surface 520 of the wearable injection guide 500. Needle depth-limiting distance 550 of the rigid needle-penetrable material 540 is uniform across the entirety of the wearable injection guide 500. Needle depth-limiting distance 550 can be based on the length of needle used for the injection. Alternatively, needle depth-limiting distance 550 can be based on how deep into the underlying tissue of the body region 510 of the individual the injection needle is intended to go. For example, needle depth-limiting distance 550 can be uniformly about 0.5 mm to about 12.5 mm across the entirety of the wearable injection guide 500. Needle depth-limiting distance 550 of the rigid needle-penetrable material 540 can be a thickness such that the one or more injection needles used to inject one or more injectable agents will reach the appropriate tissue depth when inserted through the wearable injection guide 500 as far as they will go. For example, as shown in the embodiment of FIG. 5A, a first needle with a first needle length 560a penetrates through the outer surface 530 of the rigid needle-penetrable material 540 into the underlying tissue of the body region 510 to a first depth 570a while a second needle with a second needle length 560b penetrates through the outer surface 530 of the rigid needle-penetrable material 540 into the underlying tissue of the body region 510 to a second depth 570b.

In some embodiments, the outer surface 530 of the wearable injection guide 500 includes one or more fiducials indicating whether the first needle with the first needle length 560a or the second needle with the second needle length 560b should be used at a given site on the wearable injection guide 500.

In some embodiments, as illustrated in FIG. 5B, the outer surface 530 has a varied contour defined by more than needle depth-limiting distance 550 of rigid needle-penetrable material 540 separating the outer surface 530 from the inner surface 520 of the wearable injection guide 500. For example, the outer surface 530 and the inner surface 520 of the wearable injection guide 500 can be separated by at least one first needle depth-limiting distance 550a and at least one second needle depth-limiting distance 550b. The proportion of the rigid needle-penetrable material with at least one first needle depth-limiting distance 550a and at least one second thickness 550b can vary across the entirety of the wearable injection guide 500. The at least one first needle depth-limiting distance 550a and at least one second needle depth-limiting distance 550b can be based on the length of injection needle used for the injection. The at least one first needle depth-limiting distance 550a and at least one second needle depth-limiting distance 550b can be based on how deep the injection needle is intended to be injected into the underlying tissue of the body region 510. For example, the at least one first needle depth-limiting distance 550a and the at least one second needle depth-limiting distance 550b can vary from about 0.5 mm to about 12.5 mm across the entirety of the wearable injection guide 500. The at least one first needle depth-limiting distance 550a and the at least one second needle depth-limiting distance 550b of the rigid needle-penetrable material 540 can vary such that the one or more injection needles used to inject the one or more injectable agents will reach the appropriate tissue depth when they are inserted as far as they will go. For example, as illustrated in the embodiment of FIG. 5B, needle 560 penetrates a first portion of the outer surface 530 with a first needle depth-limiting distance 550a and through the rigid needle-penetrable material 540 into the underlying tissue of the body region 510 to a first depth 570a while needle 560 penetrates a second portion of the outer surface 530 with a second needle depth-limiting distance 550b and through the rigid needle-penetrable material 540 into the underlying tissue of the body region 510 to a second depth 570b.

In some embodiments, as illustrated in FIG. 5B, the injection needle may reach a stop point when the needle hub 580 comes in contact with the outer surface 530 of the wearable injection guide 500. The needle hub 580 (or syringe adapter) can be located at the proximal end of the injection needle 560 (also see FIG. 1B) and used to attach the injection needle to the barrel of a syringe by means of a press-fit or a twist-on mechanism.

In some embodiments, as illustrated in FIG. 5C, the outer surface 530 of the wearable injection guide 500 can include a downward tapered access surface 590. In an embodiment, the downward tapered access surface 590 can be used to help direct an injection needle 560 towards the center of an injection site defined by the one or more fiducials. In some embodiments, the downward tapered access surface 590 of the outer surface 530 accommodates the injection needle 560 to a stop point dependent upon the size of the needle hub 580 or the diameter of the syringe 585, allowing the injection needle 560 to penetrate the underlying tissue of the body region 510 to a specific depth 570.

In some embodiments, at least one of the one or more fiducials indicative of a treatment parameter is placed so as to coincide with one or more portions of the outer surface of the wearable injection guide, e.g., at one or more of at least a first needle depth-limiting distance or one or more of at least second needle depth-limiting distance between the outer and inner surfaces of the rigid needle-penetrable material.

In some embodiments, the depth to which an injection needle is injected through the wearable injection guide and into the underlying tissue of the body region is dependent upon both the specific features of the body region and on the injectable agent being injected at said injection site. For example, specific features of an individual's face could dictate injection depth, including the severity of lines or wrinkles and/or the thickness of the tissue layers at any given injection site. Dermal thickness in most areas of the face is less than 1 mm thick. For example, the thickness of the epidermis (top layer of skin) is about 0.05 mm near the eye lids while the epidermis on the rest of the face is on average of about 0.1 to 0.3 mm. In addition, the injection depth may be dependent upon the age of the individual, as the tissue layers thin with increasing age. Furthermore the depth may be dependent upon the injectable agent being injected and the type of tissue into which said injectable agent is injected. For example, a dermal filler, e.g., hyaluronic acid, can be injected into the superficial papillary dermis for treating fine wrinkles and scars, but is injected deeper into the reticular dermis for deeper lines. Similarly, bovine or human collagen filler is injected into the papillary and middle dermis to treat fine lines and wrinkles in, e.g., the perioral area (e.g., the cutaneous upper lip), the periorbital area, and glabella of the face. Polymethylmethacrylate microspheres filler can be injected subdermally, e.g., into the border of the dermis and subcutaneous fat, to treat rhytids and scars. The botulinum neurotoxin, for example, is injected to about 2 to 3 mm below the surface of the skin.

In some embodiments, the at least one injectable agent is injected into the muscle of the underlying tissue of the body region of the individual. Non-limiting examples of injectable agents that are injected intramuscularly include neurotoxins, codeine, morphine, methotrexate, metoclopramide, olanzapine, streptomycin, diazepam, prednisone, penicillin, interferon beta-la, testosterone, estradiol, dimercaprol, ketamine, Lupron, maloxone, quinine, vitamin B12, Gardasil, hepatitis A vaccine, rabies vaccine, and influenza vaccine.

In some embodiments, the at least one injectable agent is injected subcutaneously. Non-limiting examples of injectable agents that are injected subcutaneously include insulin, morphine, diacetylmorphine, and goserelin.

In some embodiments, the at least one injectable agent is injected intradermally. Non-limiting examples of injectable agents that are injected intradermally include influenza vaccines, tuberculosis skin tests, and allergy shots.

Figure 6A:
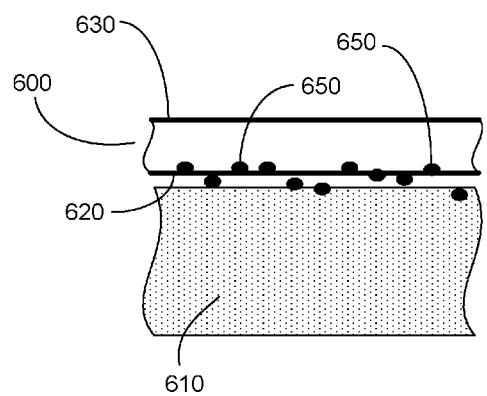
FIG. 6A is a schematic of a cross-section through a wearable injection guide with an agent.

In some embodiments, the wearable injection guide can further include one or more agents dispensed to the individual's skin, exemplary aspects of which are illustrated in FIGS. 6A-6D. FIGS. 6A-6D illustrate a cross-sectional view of a wearable injection guide 600 that includes an inner surface 620 having form-fitting contours substantially conforming to the topography of a body region 610 of an individual and an outer surface 630. FIG. 6A illustrates a cross-sectional view of an embodiment of wearable injection guide 600 in which the inner surface 620 of the wearable injection guide 600 is coated or impregnated with one or more agents 650 capable of dispersing from the inner surface 620 to an underlying tissue of the body region 610. In some embodiments, the one or more agents 650 are added as a thin coating over the inner surface 620 of the wearable injection guide 600 either at the time of manufacture or just prior to use. In some embodiments, the one or more agents 650 are impregnated into an inner surface 620 of wearable injection guide 600 that is highly porous. In some embodiments, the one or more agents 650 are released from the inner surface 620 of the wearable injection guide 600 in a time-dependent manner, being fully dispersed over the course of a treatment period. For example, the one or more agents 650 incorporated into a porous inner surface 620 of a wearable injection guide 600 may leach out from the inner surface and onto the underlying tissue of the body region at a rate dependent upon the porosity of the wearable injection guide, with more rapid release from larger pores relative to release from smaller pores. In some embodiments, the one or more agents 650 can be dispersed from the inner surface 620 of the wearable injection guide 600 over the course of a treatment period lasting from about 5 minutes to about 120 minutes, e.g., the time spent in a physician's or other practitioner's office receiving treatment. It is also contemplated that the treatment time could be shorter than 5 minutes or longer than 120 minutes and take place in the context of self-treatment with an injectable agent.

In some embodiments, release of the one or more agents 650 from the inner surface 620 of the wearable injection guide 600 is initiated by one or more stimulus such as, for example, exposure to light, skin pH, and/or temperature. For example, the one or more agents can be released from the inner surface 620 of wearable injection guide 600 in response to exposure to normal skin surface temperature, e.g., about 31 degrees Centigrade to about 35° degrees Centigrade. For example, the one or more agents can be released from the inner surface 620 of wearable injection guide 600 in response to heating the wearable injection guide prior to deployment onto the individual. Rozman et al. describe a non-limiting example of a temperature-sensitive microemulsion for delivery of an agent (see, e.g., Rozman, et al., *AAPS PharmSciTech* (2009) 10:54-61, which is incorporated herein by reference). For example, the one or more agents can be released from the inner surface 620 of wearable injection guide 600 in response to exposure to normal skin pH, e.g., about pH 5.4. Non-limiting examples of pH sensitive delivery systems are described in Slepushkin et al., *J. Biol. Chem.* (1997) 272:2382-2388, which is incorporated herein by reference. In some embodiments, the one or more agents can be released from the inner surface of the wearable injection in response to exposure to ambient light or other light source. Non-limiting examples of light-triggered delivery systems are described in Yavlovich et al., *Mol. Membr. Biol.* (2010) 27:364-381, which is incorporated herein by reference. In some embodiments, the one or more agents 650 are released from the inner surface 620 of the wearable injection guide 600 immediately after removal of a cover that otherwise prevents premature release of the one or more agents 650.

Figure 6B:
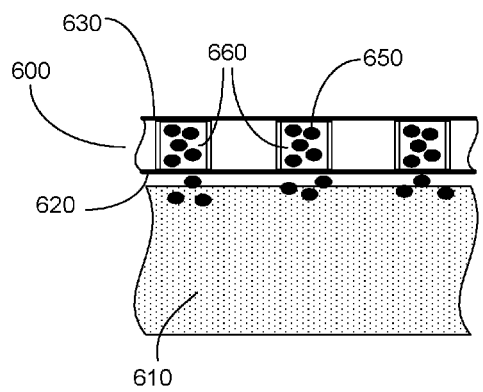
FIG. 6B is a schematic of a cross-section through a wearable injection guide with an agent.

FIG. 6B illustrates a cross-sectional view of an embodiment of a wearable injection guide 600 that includes at least one agent-containing reservoir 660 containing one or more agents 650. The at least one agent-containing reservoir 660 is preferably positioned on or near the inner surface 620 of the wearable injection guide 600 and in close proximity to the surface of a body region 610. The at least one agent-containing reservoir 660 can include one or more agents 650 configured to be released from the at least one agent-containing reservoir 660 and on to the underlying surface of a body region 610. In some embodiments, the one or more agents 650 are released from the at least one agent-containing reservoir 660 prior to injection of the one or more needles into the underlying tissue of the body region 610. For example, the one or more agents 650 can include one or more analgesic agents released from the at least one agent-containing reservoir 660 prior to injection of the one or more needles to mitigate any pain associated with needle injection. The agent-containing reservoir may have a seal, e.g., an adhesive film or tape, which is removed just prior to deploying the wearable injection guide, allowing for release of the one or more agents. In some embodiments, the one or more agents 650 are released from the at least one agent-containing reservoir 660 at any time prior, during and/or following insertion of the one or more injection needles through the wearable injection guide and into an underlying tissue of the body region of the individual. The timing for release of the one or more agents 650 from the at least one agent-containing reservoir 660 is dependent upon the nature of the one or more agents 650 and the type of treatment. In some embodiments, the at least one agent-containing reservoir 660 is incorporated into the rigid material at or near at least one of the one or more injection needle access regions. In some embodiments, the at least one agent-containing reservoir 660 is in close proximity to the one or more injection needle access regions. In some embodiments, the at least one agent-containing reservoir 660 is incorporated into at least one of the one or more injection needle access regions.

Figure 6C:
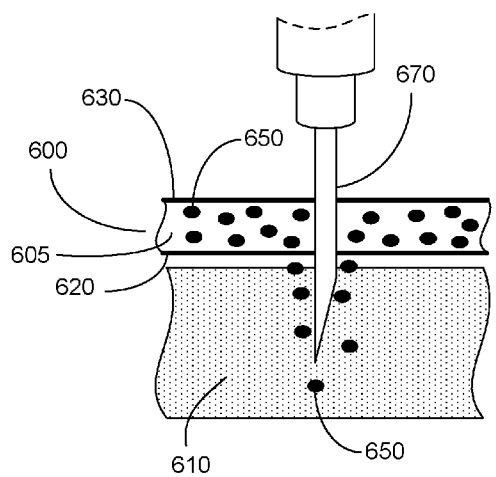
FIG. 6C is a schematic of a cross-section through a wearable injection guide with an injection needle with an agent.

FIG. 6C illustrates a cross-sectional view of an embodiment of a wearable injection guide 600 including one or more agents 650 contained in layer 605 between the inner surface 620 and the outer surface 630 of wearable injection guide 600. Upon insertion of a needle 670 through wearable injection guide 600, the one or more agents 650 are released from layer 605 of the wearable injection guide 600 and onto or into the underlying tissue of body region 610. For example, the injection needle may be coated with the agent as it passes through the wearable injection guide, carrying the agent into the underlying tissue of the body region during the injection process. In this way, an analgesic or antiseptic, for example, can be released in concert with injection of one or more needles into the underlying tissue of the body region 610. In some embodiments, at least a portion of layer 605 between the inner surface 620 and the outer surface 630 includes a single needle-penetrable reservoir containing one or more agents 650. In some embodiments, at least a portion of layer 605 includes multiple needle-penetrable reservoirs wherein only one of the multiple needle-penetrable reservoirs is punctured at any given time during insertion of needle 670.

Figure 6D:
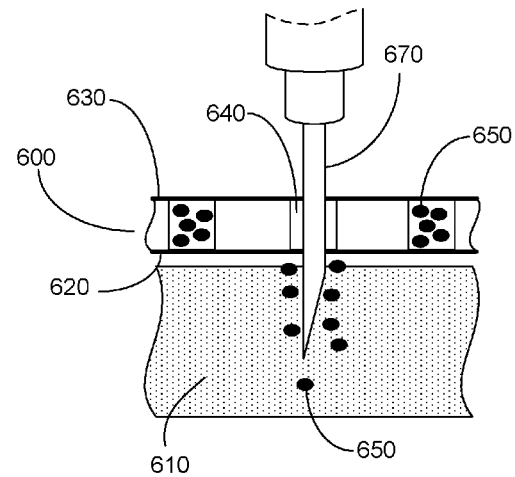
FIG. 6D is a schematic of a cross-section through a wearable injection guide with an injection needle with an agent.

FIG. 6D illustrates a cross-sectional view of a wearable injection guide 600 including one or more agents 650 contained within one or more injection needle access regions 640 of the wearable injection guide 600. The one or more agents 650 contained within the one or more injection needle access regions 640 are released onto or into the underlying tissue of the body region 610 upon insertion of needle 670. In an embodiment, the one or more agents can be contained in a reservoir, e.g., a needle-penetrable bubble-like reservoir, which is inserted into the injection needle access region following manufacture. In an embodiment, the one or more agents can be contained in a gel placed into one or more of the injection needle access regions. The gel can include, but is not limited to, one or more of a cationic polymer, a hydrogel, or organogel. In this way, an analgesic or antiseptic, for example, can be released in concert with needle injection into the underlying tissue of the body region 610.

In some embodiments, the one or more agents released from the wearable injection guide include one or more analgesics for reducing pain associated with the injection treatment. Non-limiting examples of analgesics include lidocaine, prilocaine, tetracaine, cocaine, pramoxine, dibucaine, benzocaine, dyclonine, a NSAID, or an opiate. For example, lidocaine, either alone or in combination with prilocaine as a eutectic mixture (2.5% lidocaine/2.5% prilocaine) can be used to ease the acute pain of needle insertion (see, e.g., McCleane, *Curr. Opin. Anesthesiol.*, (2010) 23:704-707; Kundu & Achar, *Am. Fam. Physician* (2002) 66:99-102, which are incorporated herein by reference).

In some embodiments, the at least one analgesic can include one or more of a vapocoolant or skin refrigerant, e.g., menthol; ethyl chloride; dichlorodifluromethane mixed with trichloromonofluoromethane; or pentafluoropropane mixed with tetrafluoroethane; and the like.

In some embodiments, the one or more agents released from the wearable injection guide include one or more of a disinfectant, antiseptic or sterilant for disinfecting the surface of the body region prior to or during injection of the injectable agent. Non-limiting examples of disinfectants, antiseptics and/or sterilants include isopropanol, silver compounds, ethanol, povidone, iodine, glutaraldehyde, formaldehyde, chlorhexidine gluconate, sodium hypochlorite, quaternary ammoniums compounds, hydrogen peroxide, and phenols.

In some embodiments, the one or more agents released from the wearable injection guide include one or more therapeutic agents. Non-limiting examples of therapeutic agents include retinoids, corticosteroids, chemotherapeutics, antimicrobials (i.e., antibacterial agents, antiviral agents, or antifungal agents).

In some embodiments, the one or more agents released from the wearable injection guide include at least one retinoid. Retinoids can be used for treating various conditions of the skin including, but not limited to, acne, psoriasis, photodamaged skin and cancers including AIDS-related Kaposi's sarcoma and cutaneous T-cell lymphoma. Non-limiting examples of retinoids for topical use include alitretinoin, bexarotene, adapalene, tazarotene, and isotretinoin.

In some embodiments, the one or more agents released from the wearable injection guide include at least one corticosteroid. Corticosteroids can be used for treating various inflammatory dermatoses including, but not limited to, atopic dermatitis, psoriasis, lupus erythematosus, and the like. Non-limiting examples of corticosteroids for topical use include hydrocortisone and derivatives, betamethasone and derivatives, dexamethasone, prednisolone and derivatives, fluocinolone acetonide, fluorometholone, alclometasone dipropionate, triamcinolone acetonide, clocortolone pivalate, flumethasone pivalate, mometasone furoate, flurandrenolide, prednicarbate, fluticasone propionate, desonide, halcinonide, desoximetasone, flurandrenolide, fluocinonide, amcinonide, fluocinolone acetonide, and diflorasone diacetate.

In some embodiments, the one or more agents released from the wearable injection guide include at least one chemotherapy agent for treating a cancer or other condition the body region. Non-limiting examples of chemotherapy agents for topical use include fluorouracil used for treating actinic keratoses and some types of basal cell carcinomas of the skin. In an embodiment, the at least one chemotherapy agent includes an immunomodulator, non-limiting examples of which include imiquimod, tacrolimus and pimecrolimus. In an embodiment, the at least one chemotherapy includes at least one agent for modulating pigmentation, non-limiting examples of which include hydroquinone, monobenzene, mequinol, trioxsalen and methoxsalen.

In some embodiments, the one or more agents released from the wearable injection guide include one or more antimicrobial agents. The one or more antimicrobial agents can further include at least one of an antibacterial agent, antiviral agent, or antifungal agent.

In some embodiments, the one or more antimicrobial agents released from the wearable injection guide include at least one antibacterial agent configured to prevent or minimize bacterial infection on the surface of the body region. In some embodiments, the at least one antibacterial agent released from the wearable injection guide is configured to prevent or minimize bacterial infection associated with injecting one or more injectable agents into the underlying tissue of the body region. In some embodiments, the at least one antibacterial agent released from wearable injection guide is configured to treat or prevent or minimize other bacterial infections on the individual's skin such as those associated with acne or rosacea, for example. Non-limiting examples of antibacterial agents commonly used for topical applications include benzoyl peroxide, sodium sulfacetamide, erythromycin, mupirocin, retapamulin, bacitracin, neomycin, polymyxin b/e, silver sulfadiazine, or tetracycline.

In some embodiments, the one or more antimicrobial agents released from the wearable injection guide include at least one antiviral agent to prevent or treat a viral infection. For example, the at least one antiviral agent can be released from the wearable injection guide to prevent or treat a viral infection on the individual's face such as that associated with herpes simplex types 1 and 2. Non-limiting examples of antiviral agents commonly used for topical applications include acyclovir, docosanol, famciclovir, imiquimod, penciclovir, valacyclovir, and vidarabine.

In some embodiments, the one or more antimicrobial agents released from the wearable injection guide include at least one antifungal agent to prevent or treat fungal infection on the individual's skin. In some embodiments, the at least one antifungal agent is released from the wearable injection guide to prevent or treat a fungal infection on the individual's face such as that associated with rosacea, for example. Non-limiting examples of antifungal agents commonly used for topical applications include amphotericin B, butaconazole, butenafine, ciclopirox olamine, clotrimazole, econazole, ketoconazole, miconazole, naftifine, natamycin, nystatin, oxiconazole, sulconazole, terbinafine, terconazole, tioconazole, tolnaftate, and metronidazole.

The one or more agents included in either at least one agent-containing reservoir or coated or impregnated on the inner surface of the wearable injection guide can further include a formulation. In some embodiments, the one or more agents can be formulated as part of a stimulus responsive polymer or gel, as described above herein. In some embodiments, the one or more agents can be formulated as polymers, gels, microparticles, nanoparticles, or solutions.

The wearable injection guide further includes means for immobilizing the wearable injection guide onto a body region of an individual. In some embodiments, the means for immobilizing the wearable injection guide can include a reversible adhesive on a surface of the rigid material of the wearable injection guide. The reversible adhesive can be incorporated into or released from the inner surface of the wearable injection guide. In some embodiments, the reversible adhesive can be one or more pressure sensitive adhesive, e.g., adhesive tape, applicable for skin contact. Non-limiting examples of adhesives designed for healthcare use include any of a number of silicone-based pressure sensitive adhesives from, for example, Dow Corning, Midland, Mich. or 3M, St. Paul, Minn.

In some embodiments, the reversible adhesive can be applied to at least a portion of the surface of the body region of the individual prior to placement of the wearable injection guide onto the body region. In an embodiment, the adhesive is simply a gel, e.g., a skin lotion or petroleum jelly, which causes the wearable injection guide to stay in one place on the surface of the body region. In an embodiment, the reversible adhesive is mixed with one or more other agent, e.g., an analgesic agent and/or an antiseptic agent.

Figure 7:
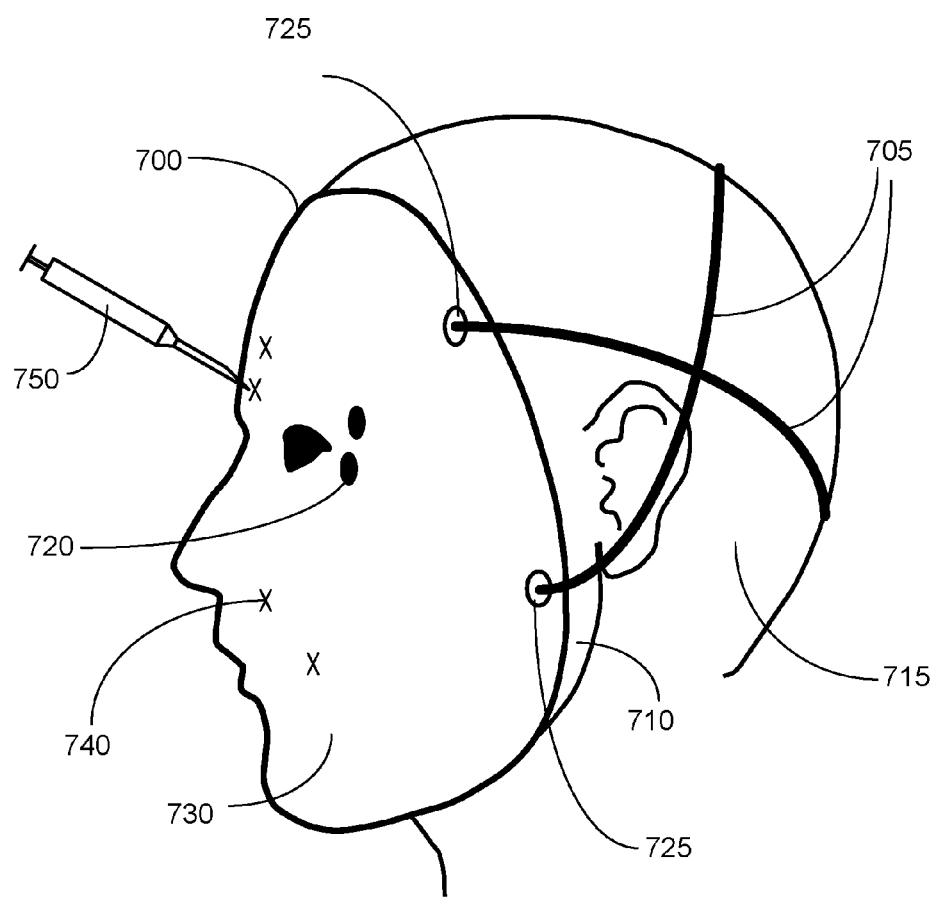
FIG. 7 is a schematic of a wearable injection guide on a face of an individual.

In some embodiments, the means for immobilizing the wearable injection guide on the body region of an individual can include one or more body portion-encircling piece. FIG. 7 illustrates a non-limiting example of a wearable injection guide 700 strapped to a body region 710 of an individual's face. The one or more body portion-encircling piece, e.g., straps 705 can be secured at one or both ends to attachment sites 725 associated with the wearable injection guide 700. The one or more straps 705 can be secured in one or more directions around the individual's head 715. Alternatively, the one or more straps 705 can be secured around the ears. The one or more straps 705 can include one or more of an elastic strap, leather strap, plastic strap or other material suitable for a strap. The one or more straps 705 can further include one or more attaching devices. Non-limiting examples of attaching devices include one or more buckles, snaps, buttons, or other interlocking attaching devices. In some embodiments, the one or more straps adjustably adhere to one another using hook and loop surfaces, e.g., Velcro®. The wearable injection guide 700 is kept immobilized on the body region 710, allowing for insertion of one or more injection needles 750 through the one or more injection needle access regions 720 and/or the one or more fiducials 740 and into an underlying tissue of the body region 710. Similar body portion-encircling pieces are contemplated for immobilizing a wearable injection guide to other parts of an individual's body, e.g. the torso, abdomen, head, neck, lower extremities, upper extremities, buttocks, and/or any other body region accessible for injection.

The body portion-encircling piece can further include other means of immobilizing the wearable injection guide to the body region of the individual such as, for example, a sleeve or a clamp. For example, the wearable injection guide may be incorporated into a sleeve that fits over an upper or lower extremity or around the neck. In some embodiments, the wearable injection guide may be incorporated into a piece of clothing, e.g., a shirt or shorts, that allows the wearable injection guide to be firmly kept in place on the surface of the body region. For example, the wearable injection guide may include a clamp in the shape of a "C" that fits snuggly around an upper or lower extremity.

In some embodiments, the means for immobilizing the wearable injection guide can include a portion of the wearable injection guide that is inserted into the individual's mouth and held in place with the teeth. In some embodiments, the means for immobilizing the wearable injection guide can include one or more prongs extending from the inner surface of the wearable injection guide that insert into each nostril of the individual's nose.

In some embodiments, the wearable injection guide can further include one or more alignment marks configured to align with one or more reference points on the body region of the individual. In some embodiments, the wearable injection guide can include one or more alignment marks configured to align with one or more reference marks placed on a surface of the body region of the individual. For example, the one or more alignment marks may be configured to align with one or more reference marks placed on the surface of the body region by a physician, other practitioner or the individual. In some embodiments, the wearable injection guide can include one or more alignment marks configured to align with one or more topographical landmarks of the body region. Examples of topographical landmarks include but are not limited to pigmentation, a pigmented area, e.g., freckle, mole, or birthmark, a skin texture pattern, a tattoo, a subsurface blood vessel, an anatomical feature, an eye, a nose, or lips. In some embodiments, at least a portion of the rigid material of the wearable injection guide may be transparent near the one or more alignment marks to facilitate alignment of the alignment marks with one or more underlying reference points on the body region.

In some embodiments, the wearable injection guide can further include a barcode or radiofrequency identification tag for verifying that a given wearable injection guide is suitable for a given individual. For example, a barcode specific for a given individual may be placed on the wearable injection guide either during or after manufacturing and used to verify who the wearable injection guide was designed and manufactured for. Similarly, a radiofrequency identification tag may be placed on the wearable injection guide following manufacture and used for verifying appropriate use with a given individual.

The wearable injection guide can further include a thermal-regulating mechanism. The thermal-regulating mechanism can be used to alter the temperature of the wearable injection guide to a temperature above or below about 98.6 degrees Fahrenheit (° F.) (37 degrees centigrade (° C.)).

In some embodiments, the thermal-regulating mechanism is a cooling mechanism configured to reduce the temperature of the wearable injection guide to a temperature below about 98.6° F. (37° C.) or normal body temperature. The cooling mechanism can be configured to reduce pain during needle injection and/or to prevent potential swelling following needle injection. In an embodiment, the wearable injection guide can include a material having a relatively high heat capacity, e.g., a ceramic material or a gel, and may not need a separate cooling mechanism. For example, following refrigeration, the wearable injection guide containing or formed from a high heat capacity material can maintain a cool temperature while in contact with the body region for an extended period of time. In some embodiments, the wearable injection guide is cooled by placing the wearable injection guide in a cooling device prior to placement on a body region of an individual. For example, the wearable injection guide can be stored in a cooling device until use. Alternatively, the wearable injection guide can be placed into the cooling device just prior to use for a sufficient time to cool the wearable injection guide to an appropriate temperature. The cooling temperature can be about 10° C. to about 0° C. It is understood that the cooling temperature can fall outside this range, but is contemplated to be sufficiently cool enough to reduce pain and swelling but not so cold as to be painful or damaging to the underlying tissue of the body region. Non-limiting examples of cooling devices for this purpose include a refrigerator, a freezer, or an ice bath.

In some embodiments, the wearable injection guide is cooled by incorporating a cooling mechanism directly into and/or on the wearable injection guide. In an embodiment, the cooling mechanism can include a chemical endothermic reaction using, for example, water and ammonium nitrate. For example, the components of a chemical endothermic reaction can be included in or on the inner surface of the wearable injection guide and activated upon removal of the wearable injection guide from a protective wrap. In an embodiment, the cooling mechanism can include thermoelectric cooling with, for example, a Peltier cooling device. Components of a Peltier cooling device can be incorporated into the inner surface of the wearable injection guide.

In some embodiments, the thermal-regulating mechanism is a heating mechanism configured to raise the temperature of the wearable injection guide to a temperature above about 98.6° F. (37° C.). The heating mechanism can be configured to increase vasodilation and/or circulation in the underlying tissue covered by the wearable injection guide prior to, during, and/or after injection of an injectable agent. In an embodiment, the wearable injection guide can include a material having a relatively high heat capacity, e.g., a ceramic material, and may not need a separate heating mechanism. For example, following heating in a warming oven, the wearable injection guide containing or made from a high heat capacity material can maintain a warm temperature while in contact with the body region for an extended period of time. In some embodiments, the wearable injection guide is warmed by heating the wearable injection guide in a heating device prior to placement onto a body region of an individual. For example, the wearable injection guide can be stored in a heating device until use. Alternatively, the wearable injection guide can be placed into the heating device just prior to use for a sufficient time to heat the wearable injection guide to an appropriate temperature. The heating temperature can be about 40° C. to about 45° C. It is understood that the heating temperature can fall outside this range, but is contemplated to be sufficiently hot enough to increase circulation but not so hot as to be painful or damaging to the underlying tissue of the body region. Non-limiting examples of heating devices for this purpose include a warming oven, a microwave, or hot water bath.

In some embodiments, the wearable injection guide is heated by incorporating a heating mechanism directly into and/or on the wearable injection guide. In an embodiment, the heating mechanism can include a chemical exothermic reaction using, for example, components of an air-activated, iron-based warmer including a combination of cellulose, iron, activated carbon, vermiculite and salt. For example, the components of a chemical exothermic reaction can be included in or on the inner surface of the wearable injection guide and activated upon removal of the wearable injection guide from a protective wrap. In an embodiment, the heating mechanism can include thermoelectric heating with, for example, a Peltier heating device. Components of a Peltier heating device can be incorporated into the inner surface of the wearable injection guide.

In some embodiments, a wearable injection guide includes a rigid material substantially impenetrable to an injection needle, the rigid material including one or more injection needle access regions arranged in a treatment pattern, the one or more injection needle access regions including one or more activatable injection event indicators. The one or more activatable injection event indicators are configured to allow the user of the wearable injection guide to determine which of the injection needle access regions have been previously used for insertion of an injection needle and consequently which portions of the underlying body region have previously been injected. In addition, the one or more activatable injection event indicators are configured to allow the user of the wearable injection guide to determine how many previous injections have been completed and where. For example, the activatable injection event indicators can indicate where insulin has previously been injected into the lower abdomen or the upper thigh. Repeatedly injecting insulin near the same place can lead to hard lumps or extra fatty deposits, and as such should be avoided. In some embodiments, the one or more activatable injection event indicators can include one or more pressure sensitive materials, e.g., one or more pressure sensitive dyes. In some embodiments, the one or more activatable injection event indicators can include one or more flowable materials, e.g., dyes, released upon penetration of an injection needle through the wearable injection guide. In some embodiments, the one or more activatable injection event indicators can include one or more materials activated by exposure to air, e.g., exposure to oxygen or moisture in the atmosphere.

Figure 8:
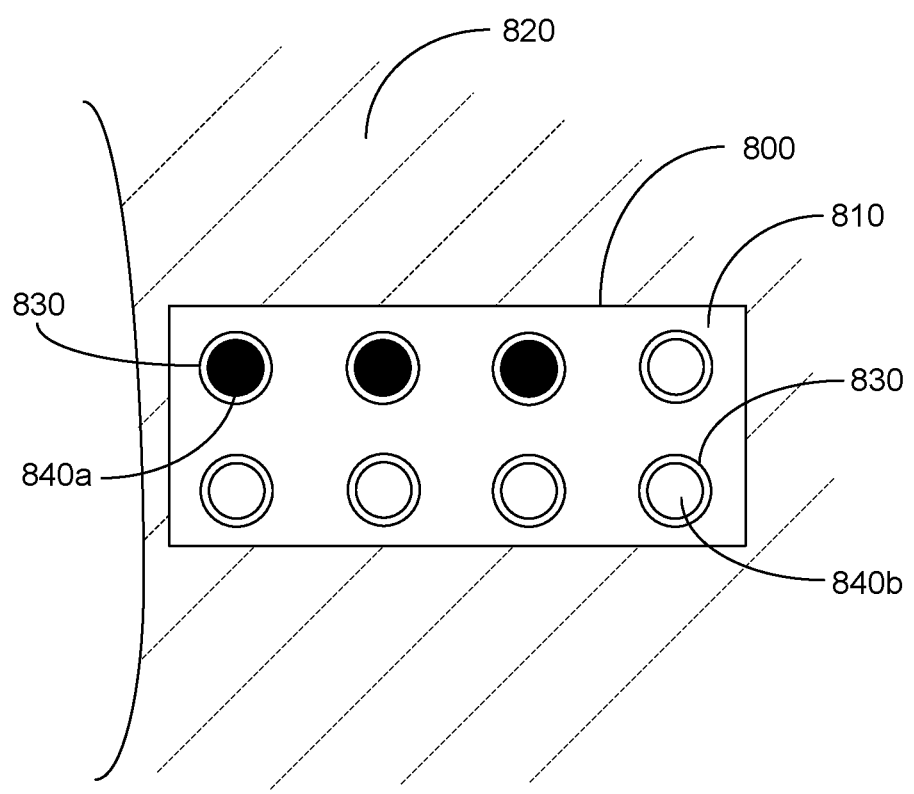
FIG. 8 is a schematic of a wearable injection guide with activatable injection event indicators.

FIG. 8 illustrates an embodiment of a wearable injection guide with one or more activatable injection event indicators. The wearable injection guide 800 comprises rigid material 810 deployed on a body region 820 of an individual. The rigid material 810 of wearable injection guide 800 includes one or more injection needle access regions 830. The one or more injection needle access regions 830 include an activatable injection event indicator in a first state 840a or in a second state 840b. In some embodiments, the one or more activatable injection event indicators include one or more materials stored in a needle-penetrable reservoir incorporated into a least one of the one or more injection needle access regions. The one or more materials stored in the needle-penetrable reservoir can include, but are not limited to, one or more flowable dyes, one or more of an oxygen sensitive, or one or more of a moisture sensitive dye.

In some embodiments, an activatable injection event indicator in a first state 840a has a first color and the activatable injection event indicator in a second state 840b has a second color. The transition from the first state 840a to the second state 840b can be triggered by insertion of an injection needle through the injection needle access region 830, resulting in a color change detectable by the user. In some embodiments, the transition from the first state 840a to the second state 840b is triggered by releasing one or more material from the injection needle access region 830. In some embodiments, the one or more material released from the injection needle access region is a flowable dye that either flows away from the injection needle access region and leaving it "colorless" or stains an otherwise colorless injection needle access region. In some embodiments, the one or more material released from the injection needle access region changes color in response to air, e.g., in response to oxygen or moisture in the atmosphere. Non-limiting examples of dyes or other materials that change color in response to oxygen include materials including methylene blue (see, e.g., U.S. Pat. No. 4,526,752, which is incorporated herein by reference). Non-limiting examples of dyes or other materials that change color in response to moisture include materials including cobalt, e.g., cobaltous chloride (see, e.g., U.S. Pat. No. 4,990,284, which is incorporated herein by reference). In some embodiments, the injection needle can puncture a seal that permits two or more materials to come into contact with each other thereby providing a colorimetric change or indicator. Other embodiments include using an indicator paper layer, e.g., pH paper, which is physically separated from a layer of a slightly basic or slightly acidic liquid, e.g., acetic acid, or baking soda and water. Once punctured by the injection needle, the liquid contacts the indicator paper, causing the indicator paper to change color.

In some embodiments, an activatable injection event indicator in a first state 840a represents an intact portion of the injection needle access region 830 while the second state 840b represents a ruptured portion of the injection needle access region 830. For example, the one or more activatable injection event indicators can include one or more needle-penetrable membranes covering at least a portion of one or more surfaces of the wearable injection guide. The difference between the first state 840a and the second state 840b can be differentiated by the user based on sight or based on touch.

FIGS. 9A-9C illustrate cross-sectional views of an embodiment of a wearable injection guide with one or more activatable injection event indicators that include one or more flowable dyes. FIG. 9A illustrates a cross-sectional view of wearable injection guide 900 prior to insertion of an injection needle, the wearable injection guide 900 comprised of rigid material 910 and deployed on a body region 920 of an individual. Rigid material 910 includes one or more injection needle access regions 930. The one or more injection needle access regions 930 include at least one needle-penetrable reservoir 940 that contains one or more flowable dyes 950. In some embodiments, the needle-penetrable reservoir contains one or more agents, as described herein, as well as the one or more flowable dyes. For example, the needle-penetrable reservoir may include one or more analgesic as well as one or more flowable dyes. FIG. 9B is a cross-sectional view of penetration of injection needle 960 through the rigid material 910 of the wearable injection guide 900 at one of the one or more injection needle access regions 930 and into the underlying tissue of body region 920 of an individual. Injection needle 960 punctures the needle-penetrable reservoir 940, releasing one or more flowable dyes 950. FIG. 9C illustrates flow of one or more flowable dyes 950 out of needle-penetrable reservoir 940 after injection needle 960 has been removed from injection-needle access region 930. In some embodiments, the one or more flowable dyes flow laterally between the inner surface of the wearable injection guide and the surface of the body region. In some embodiments, the one or more flowable dyes are carried into the underlying tissue of the body region with insertion of the injection needle.

Figure 10A:
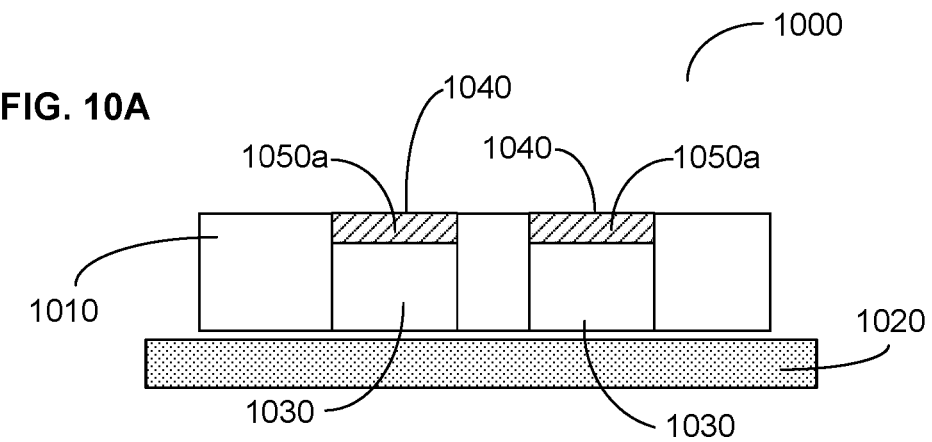
FIG. 10A is a schematic of a cross-section through a wearable injection guide prior to insertion of an injection needle.
Figure 10B:
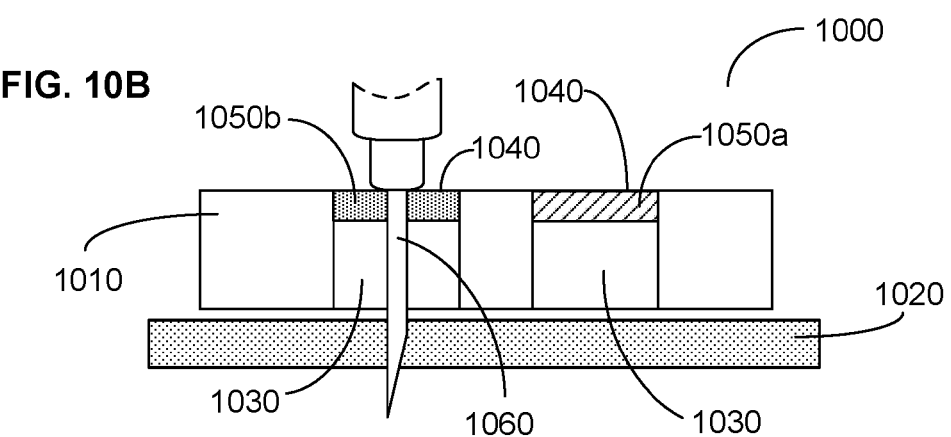
FIG. 10B is a schematic of a cross-section through a wearable injection guide during insertion of an injection needle.
Figure 10C:
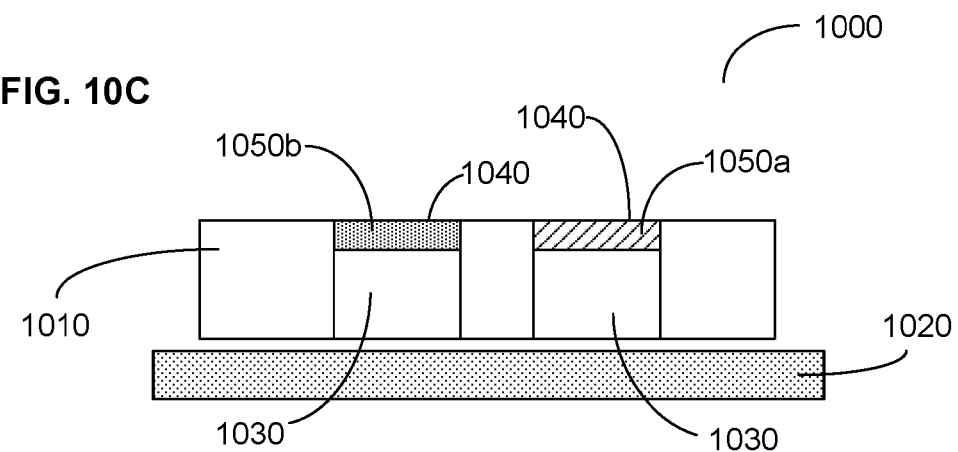
FIG. 10C is a schematic of a cross-section through a wearable injection guide after insertion of an injection needle.

FIGS. 10A-10C illustrate cross-sectional views of an embodiment of a wearable injection guide 1000 with one or more activatable injection event indicators that include one or more pressure sensitive materials. FIG. 10A illustrates a cross-section through wearable injection guide 1000 prior to insertion of an injection needle, the wearable injection guide 1000 composed of rigid material 1010 and deployed on a body region 1020 of an individual. Rigid material 1010 includes one or more injection needle access regions 1030. The one or more injection needle access regions 1030 include an upper portion 1040 with one or more pressure sensitive materials in a first state 1050a. FIG. 10B illustrates a cross-sectional view of wearable injection guide 1000 composed of rigid material 1010 through which injection needle 1060 has been inserted. As a result of inserting injection needle 1060 through the upper portion 1040 of the one or more injection needle access regions 1030, the one or more pressure sensitive materials of upper portion 1040 shift to a second state 1050b. The first state 1050a is activatable to the second state 1050b by pressure exerted during insertion of injection needle 1060. In some embodiments, the shift from first state 1050a to second state 1050b may be accompanied by a change in color detectable by a user of the wearable injection guide 1000. FIG. 10C illustrates a cross-sectional view of wearable injection guide 1000 composed of rigid material 1010 and deployed on a body region 1020 of an individual after withdrawal of injection needle 1060. The wearable injection guide 1000 has upper portion 1040 in a first state 1050a, e.g., a first color, indicative of an injection needle access region 1030 that has not been accessed and has upper portion 1040 in a second state 1050b, e.g., a second color, indicative of an injection needle access region that has been accessed. It is contemplated that the pressure sensitive materials can be incorporated into any portion, e.g., upper, middle, lower or throughout, the one or more injection needle access regions. In some embodiments, the one or more pressure sensitive materials are incorporated near the one or more injection needle access regions. For example, the one or more pressure sensitive materials can be incorporated into at least a portion of the outer surface of the rigid material that is contacted by a needle hub or syringe body associated with an injection needle when the injection needle is inserted to a stop point through the rigid material at an injection needle access region defined by an opening.

One or more pressure sensitive materials can be incorporated into the wearable injection guide for use as an activatable injection event indicator. In some embodiments, pressure sensitive dye chemistries can be applied directly to the wearable injection guide or applied as a film that is layered into or onto the wearable injection guide. Various carrier plastics and/or layers, e.g., polyester can be used as carrier layers for pressure sensitive dyes.

In some embodiments, the one or more pressure sensitive materials include encapsulated single or multiple component dye systems wherein the coating of the encapsulated dye system ruptures in response to a specific pressure, releasing the encapsulated dye. In some embodiments, the one or more pressure sensitive materials include polymeric dyes that undergo a conformational change in response to an exerted pressure. In some embodiments, the one or more pressure sensitive materials include a diffusion based dye system in which a dye is induced to diffuse vertically and/or horizontally, e.g., through a porous diffusion layer, in response to an exerted pressure. In some embodiments, the one or more pressure sensitive materials include hydrochromatic dyes in which exerted pressure causes movement of an aqueous medium to come into contact with a hydrochromatic dye layer. In some embodiments, the one or more pressure sensitive materials include phase change compositions in which exerted pressure induces a chemical composition to undergo a transition from one physical state to a second physical state, e.g., irreversible crystallization of a liquid material in response to exerted pressure with an associated color change.

Non-limiting examples of pressure sensitive materials include encapsulated dyes and dye systems, polyacetylenes, leuco dyes, solvent chemically initiated color change systems, frictionally sensitive dyes, separated dye layers, partition dyes, electron transfer dyes, two-component chemical dyes, organic and inorganic color change dye systems, acid/base dye systems, melting waxes, sublimation dyes and the like.

In some embodiments, the one or more pressure sensitive materials include encapsulated leuco dye compositions. For example, a dye and an activator can be separately encapsulated in microspheres and affixed to a surface of the wearable injection guide. The combination of the encapsulated dye microspheres and the activator microspheres are otherwise colorless or of a first color, but upon exposure to an exerted pressure, the capsules break, the dye and activator combine, resulting in a detectable color change. Encapsulated dyes for this purpose are commercially available (from, e.g., NuCoat, Inc., Minneapolis, Minn.; Appleton Papers, Inc., Appleton, Wis.; Mircotek Laboratories, Inc., Dayton, Ohio).

In some embodiments, a wearable injection guide includes a rigid needle-penetrable material having an inner surface, and outer surface, and one or more activatable injection event indicators, the inner surface having form-fitting contours substantially conforming to a topography of a body region of an individual and the outer surface including one or more fiducials indicative of at least on treatment parameter. The one or more activatable injection event indicators are configured to allow the user of the wearable injection guide to determine where the rigid needle-penetrable material has been accessed with an injection needle and consequently which portions of the underlying body region have previously been injected. In some embodiments, the one or more activatable injection event indicators are positioned on top of at least a portion of the outer surface of the rigid-needle penetrable material. In some embodiments, the one or more activatable injection event indicators are incorporated into at least a portion of the outer surface and/or inner surface of the rigid needle-penetrable material. In some embodiments, the one or more activatable injection event indicators are incorporated into at least a portion of the rigid needle-penetrable material between the outer surface of the rigid-needle penetrable material and the inner surface of the rigid-needle penetrable material. The one or more activatable injection event indicators can be incorporated into at least one of a coating, a film, a layer, or an injection needle-penetrable reservoir. The one or more activatable injection event indicators can include at least one pressure sensitive material, pressure sensitive dye, flowable dye, oxygen-sensitive dye, or moisture sensitive dye, or combinations thereof.

Figure 11A:
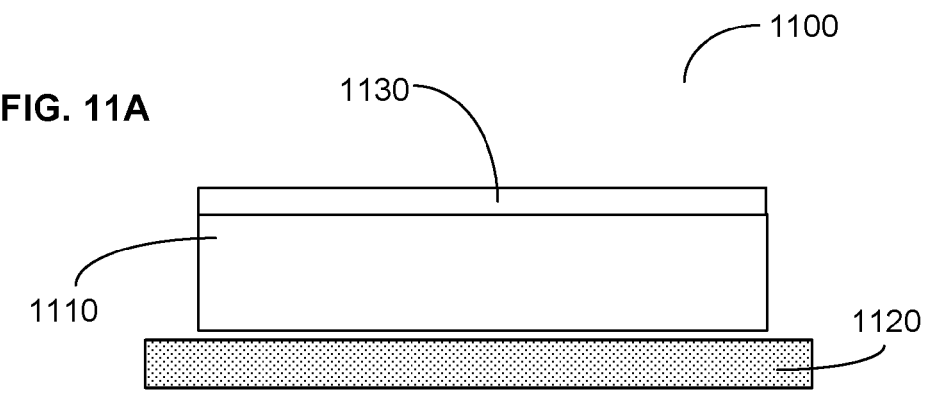
FIG. 11A is a schematic of a cross-section through a wearable injection guide prior to insertion of an injection needle.
Figure 11B:
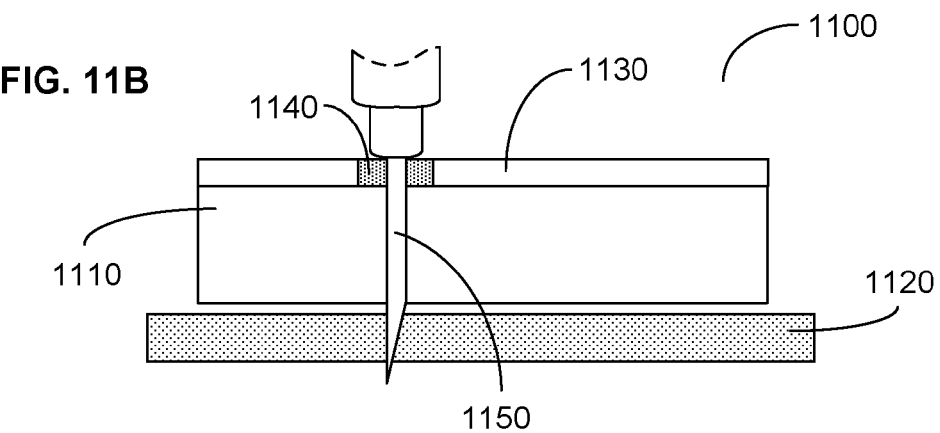
FIG. 11B is a schematic of a cross-section through a wearable injection guide during insertion of an injection needle.
Figure 11C:
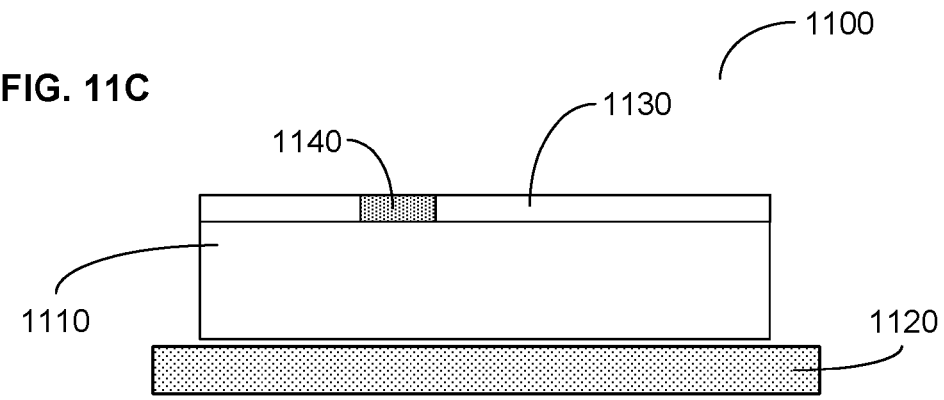
FIG. 11C is a schematic of a cross-section through a wearable injection guide after insertion of an injection needle.

FIGS. 11A-11C illustrate cross-sectional views of an embodiment of a wearable injection guide 1100 with one or more activatable injection event indicators that include one or more pressure sensitive materials. FIG. 11A illustrates a cross-section through wearable injection guide 1100 composed of needle-penetrable material 1110 and deployed on a body region 1120 of an individual. The wearable injection guide 1100 further includes a layer of pressure sensitive material in a first state 1130. The pressure sensitive material in a first state 1130 can be colorless or a first color. FIG. 11B illustrates a cross-section through a wearable injection guide 1100 composed of needle-penetrable material 1110 through which injection needle 1150 has been inserted. As a result of inserting injection needle 1150 through the layer of pressure sensitive material and the needle-penetrable material 1110, a portion of the pressure sensitive material in a first state 1130 has changed to a pressure sensitive material in a second state 1140 that differs from the first state 1130. The pressure sensitive material in a second state 1140 can be colorless, a first color or a second color. FIG. 11C illustrates a cross-sectional view of wearable injection guide 1100 composed of rigid material 1110 and deployed on a body region 1120 of an individual after withdrawal of injection needle 1150. The wearable injection guide 1100 has a layer of pressure sensitive material in a first state 1130, e.g., a first color, indicative of an area of the wearable injection guide 1100 that has not been accessed and has a portion of the pressure sensitive material in a second state 1140 that has changed to a second state that differs from the first state, e.g., a second color, indicative of where an injection needle has previously been inserted.

In some embodiments, the one or more pressure sensitive materials include pressure sensing films that can be incorporated onto or into the wearable injection guide. Non-limiting examples of pressure sensing films include carbon papers, Fujifilm Prescale™ pressure sensing film (extreme low pressure sensitive films to super high pressure sensitive films; from FujiFilm, distributed by Tekscan, Boston, Mass.), and/or Pressurex® films (from Sensor Products Inc., Madison, N.J.) can be utilized by way of example as film layers that can be incorporated into a laminated layer.

Additional examples of pressure sensitive materials include, but are not limited to those dyes disclosed in U.S. Pat. No. 5,990,199 and U.S. Patent Application 2010/0326198, which are incorporated herein by reference. Other examples include, but are not limited to, tamper evident dyes that respond to a pressure event through a color change, security inks that can be printed in a particular manner or pattern, indicator inks used in sterilization processes, tactile pressure indicating films, inks used in pressure mapping, compressible "puff" inks made with ink additives used for printing expanded patterns and print, dye migration inks where dyes migrate only under pressure, dye transfer inks where dyes transfer only under pressure.

Figure 12A:
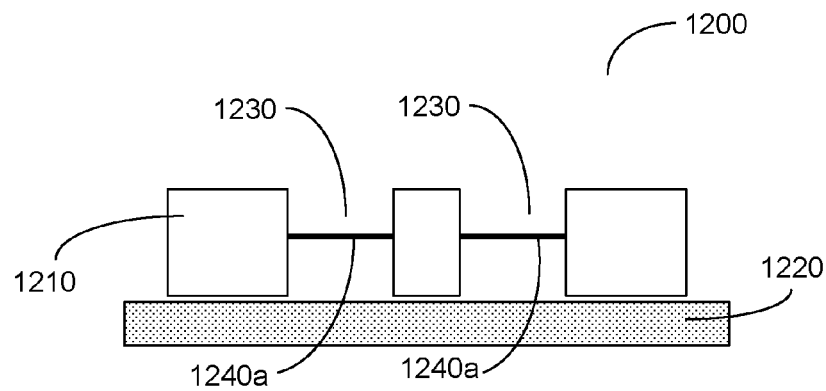
FIG. 12A is a schematic of a cross-section through a wearable injection guide prior to insertion of an injection needle.
Figure 12B:
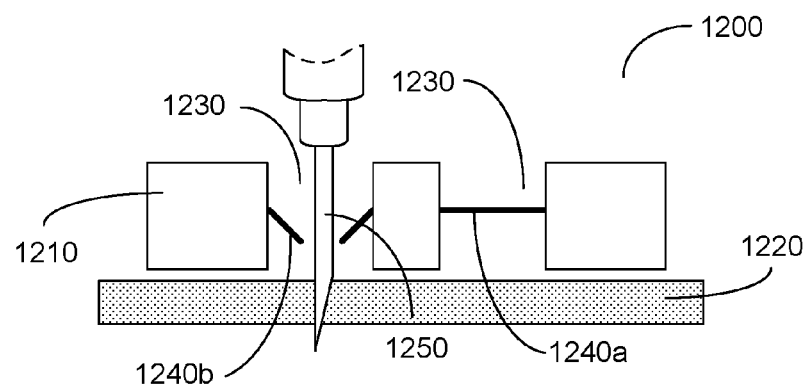
FIG. 12B is a schematic of a cross-section through a wearable injection guide during insertion of an injection needle.
Figure 12C:
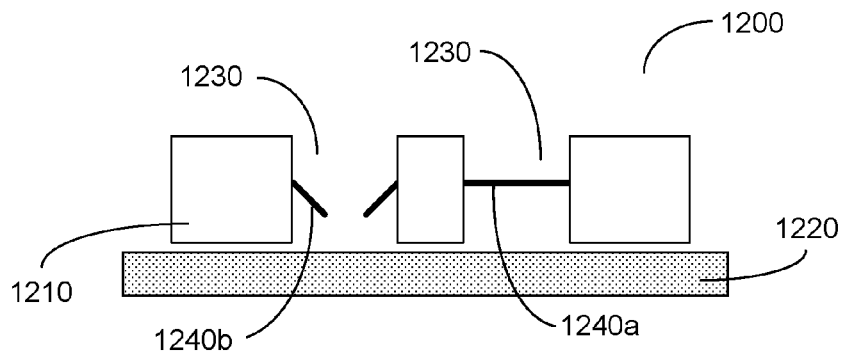
FIG. 12C is a schematic of a cross-section through a wearable injection guide after insertion of an injection needle.

In some embodiments, the activatable event indicators can be openings defined by the rigid material of the wearable injection guide indicating that injection has already been made into that site. FIGS. 12A-12C illustrate an embodiment of a wearable injection guide that includes an activatable event indicator that is the opening defined by the rigid material left after inserting and then removing an injection needle. FIG. 12A illustrates a cross-sectional view of wearable injection guide 1200 composed of rigid material 1210 and deployed on a body region 1220 of an individual. The rigid material 1210 includes one or more injection needle access regions 1230. The one or more injection needle access regions 1230 can further include a needle-penetrable membrane in an intact state 1240a. FIG. 12B illustrates penetration of injection needle 1250 through the one or more injection needle access regions 1230 and into the underlying body region 1220 of an individual. As a result of inserting the injection needle 1250, the needle-penetrable membrane is in a punctured state 1240b, otherwise creating an opening in the rigid material 1210 of the wearable injection guide 1200. FIG. 12C illustrates wearable injection guide 1200 comprised of rigid material 1210 and deployed on surface skin area 1220 of an individual after removal of injection needle 1250. The wearable injection guide 1200 has at least one needle-penetrable membrane in a first state 1240a, e.g., intact and indicative of an injection needle access region 1230 that has not been accessed and at least one needle-penetrable membrane in a second state 1240b, e.g., punctured and indicative of an injection needled access region 1230 that has been accessed. In some embodiments, the user can visually see if the needle-penetrable membrane is intact or punctured. In some embodiments, the user can feel if the needle-penetrable membrane is intact or punctured. In this way, the user can determine which injection needle access regions have been accessed and which have not been accessed.

FIG. 13 illustrates a method for administering a treatment to an individual implemented with a wearable injection guide, the wearable injection guide constructed of a rigid material formed to substantially conform in shape to a topography of a body region of an individual and including one or more injection needle access regions arranged in a treatment pattern. The method includes deploying the wearable injection guide onto the body region of the individual, wherein the body region can include at least a portion of a face, torso, abdomen, head, neck, upper extremity, lower extremity, or buttocks region of an individual. In some embodiments, the wearable injection guide is deployed on all or part of a head or neck region, e.g., face, scalp, nose, forehead, or ear regions. Block 1300 shows inserting one or more injection needles through the one or more injection needle access regions of the wearable injection guide. Block 1310 depicts injecting at least one injectable agent through the one or more injection needles into an underlying tissue of the body region of the individual.

FIG. 14 illustrates aspects of the method depicted in FIG. 13. FIG. 14 illustrates that in some embodiments, block 1300 can include one or more of optional blocks 1400 and 1410. In some embodiments, inserting the one or more injection needles through the one or more injection needle access regions of the wearable injection guide can include inserting the one or more injection needles at a 90 degree angle relative to the underlying tissue of the body region of the individual, as illustrated in block 1400. In some embodiments, inserting the one or more injection needles through the one or more injection needle access regions of the wearable injection guide includes inserting the one or more injection needles through the one or more injection needle access regions at less than a 90 degree angle relative to the underlying tissue of the body region of the individual, as illustrated in block 1410. The angle at which the one or more injection needles are inserted through the one or more injection needle access regions of the wearable injection guide is dependent upon the nature of the injectable agent and the location of the underlying tissue of the body region of the individual into which the injectable agent is being injected. For example, injections into the muscle with, e.g., penicillin may be done with an injection needle through the wearable injection guide at a 90 degree angle; injections into the subcutaneous tissue with, e.g., morphine, may be done with an injection needle through the wearable injection guide at a 45 degree angle; and injections into the epidermis or dermis with, e.g., a vaccine may be done with an injection needle through the wearable injection guide at a 10 to 15 degree angle.

In an embodiment, the angle at which the one or more injection needles are inserted through the one or more injection needle access regions of the wearable injection guide is dependent upon the angle of the one or more injection needle access regions transecting the wearable injection guide, e.g., one or more areas of rigid material of the wearable injection guide defining one or more openings, that have been manufactured into the wearable injection guide.

Figure 15:
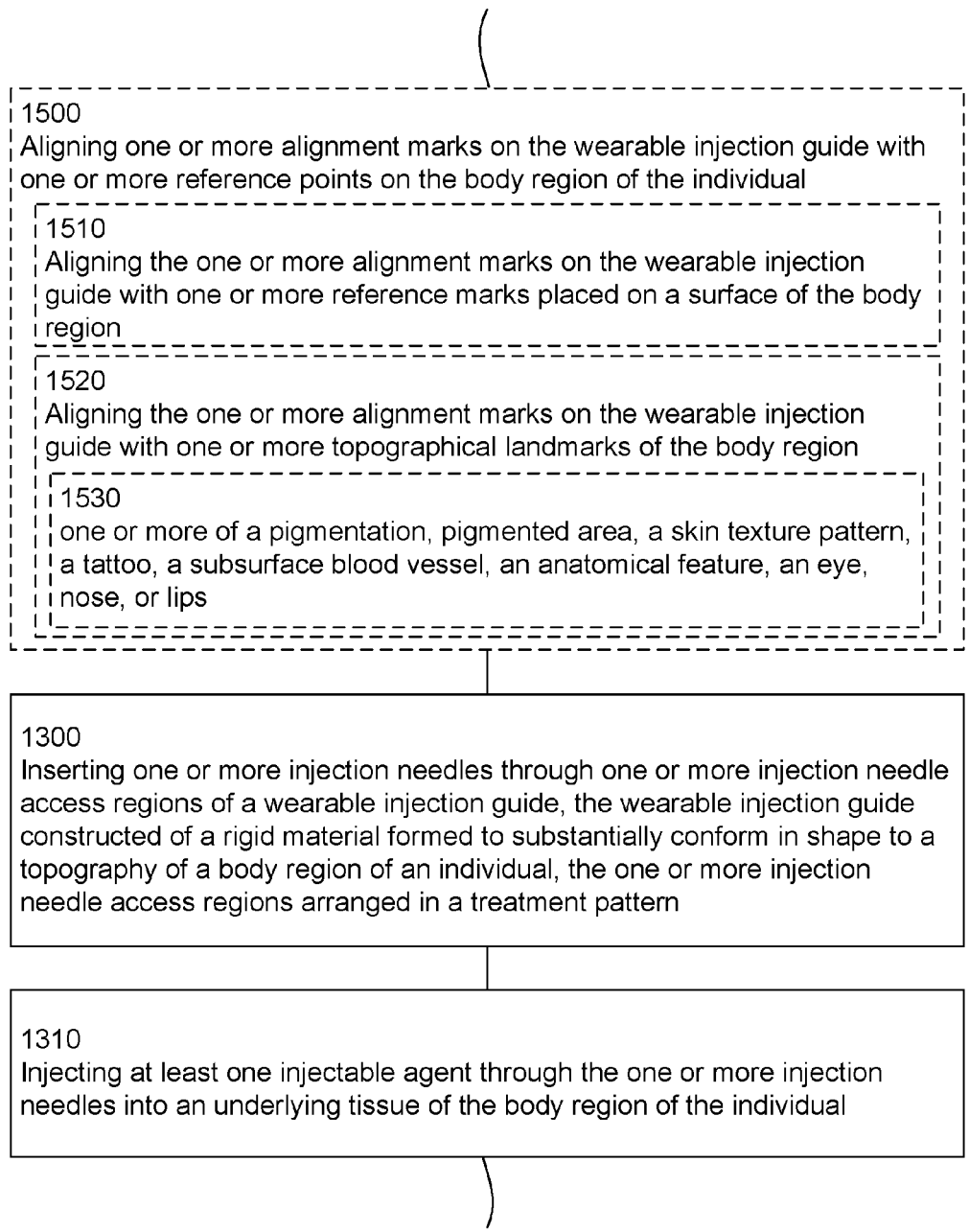
FIG. 15 is a flowchart showing aspects of a method such as depicted in FIG. 13.

FIG. 15 shows further aspects of the method illustrated in FIG. 13 for administering an injection treatment to an individual with a wearable injection guide. FIG. 15 illustrates that in some embodiments, the method can include block 1500. Block 1500 depicts aligning one or more alignment marks on the wearable injection guide with one or more reference points on the body region of the individual. Block 1500 can include one or more optional blocks 1510 and 1520. Block 1510 illustrates aligning one or more alignment marks on the wearable injection guide with one or more reference marks placed on a surface of the body region of the individual by a physician, other practitioner, or the individual themselves. For example, a physician, other practitioner, or the user, in the case of self-injection, can place reference marks in ink on the surface of the body region of the individual for use in aligning with one or more alignment marks on the wearable injection guide. Block 1520 illustrates aligning one or more alignment marks on the wearable injection guide with one or more topographical landmarks of the body region. Block 1520 further includes optional block 1530 which illustrates aligning the one or more alignment marks on the wearable injection guide with one or more of a pigmentation, a pigmented area, a skin texture pattern, a tattoo, a subsurface blood vessel, an anatomical feature, an eye, nose, or lips. Non-limiting examples of a pigmented area include freckles, moles, birth marks, or other pigmented areas on the surface of an individual's skin. Non-limiting examples of anatomical features include eyes, nose, lips, cheek bones, a joint, a belly button, or any other anatomical feature that can be used to align a wearable injection guide onto a body region of an individual. For example, a wearable injection guide for use on an individual's face may conform in shape to a topography of the individual's face including the nose and eye regions and as such fit snuggly into place. An extensive list of topographical landmarks of the facial area are described in Buckley et al., *Am. J. Psychiatry* (2005) 162:606-608, which is incorporated herein by reference.

Figure 16:
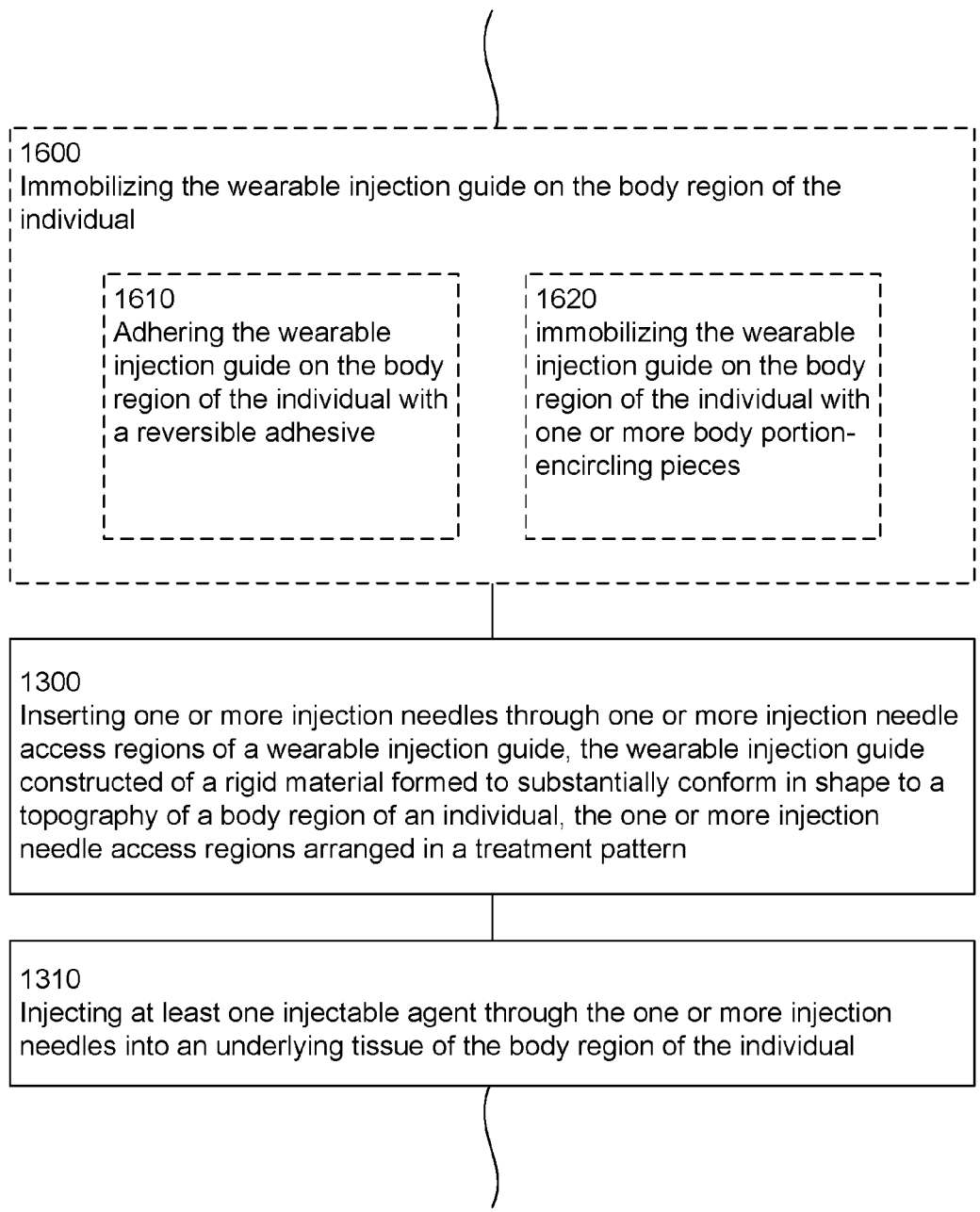
FIG. 16 is a flowchart depicting aspects of a method such as illustrated in FIG. 13.

FIG. 16 shows further aspects of the method illustrated in FIG. 13 for administering an injection treatment to an individual with a wearable injection guide. FIG. 16 illustrates that in some embodiments, the method can include block 1600. Block 1600 depicts immobilizing the wearable injection guide on the body region of the individual. In some embodiments, the wearable injection guide is immobilized on to the body region of the individual for only a short period of time, e.g., during an office visit to a physician or other practitioner. In some embodiments, the wearable injection guide is immobilized on the body region of the individual for a prolonged period of time, e.g., days or weeks, to accommodate a full course of injection treatment. Block 1600 can include one or more optional blocks 1610 and 1620. Block 1610 depicts immobilizing the wearable injection guide by adhering the wearable injection guide on the body region of the individual with a reversible adhesive. For example, the wearable injection guide can be adhered on the body region of the individual with one or more strips of medical rated double stick tape. As another example, the wearable injection guide can be adhered on the body region of the individual with a coating of adhesive, e.g., URO-Bond® IV Silicone Skin Adhesive (from, UROCARE Products, Pomona, Calif.). In some embodiments, the wearable injection guide is immobilized by using a lotion or gel, e.g., petroleum jelly, to coat the inner surface of the wearable injection guide and create friction with the underlying skin of the individual. Block 1620 depicts immobilizing the wearable injection guide by strapping the wearable injection guide on the body region of the individual with one or more body portion-encircling pieces. For example, the wearable injection guide can be strapped on the body region of the individual using a series of nylon straps including compatible portions of an adjustable loop and hook system, e.g., Velcro®. In some embodiments, the body portion-encircling pieces can include a sleeve or a clamp. For example, a snug-fitting sleeve can be used to immobilize the wearable injection guide on an upper or lower extremity. In some embodiments, the wearable injection guide is incorporated into a piece of clothing, e.g., a tee-shirt or shorts.

FIG. 17 shows further aspects of the method illustrated in FIG. 13 for administering an injection treatment to an individual with a wearable injection guide. FIG. 17 illustrates that in some embodiments, block 1310 can include one or more of optional blocks 1700 and 1710. Block 1700 depicts optionally injecting the at least one injectable agent through the one or more injection needles into one or more of epidermis, papillary dermis, reticular dermis, subcutis, or muscle of the underlying tissue of the body region of the individual. For example, the method can include using the wearable injection guide to inject one or more doses of botulinum neurotoxin into the papillary dermis of an individual's face. For example, the method can include using the wearable injection guide to inject one or more doses of fertility hormones into the muscle of an individual's upper thigh. In some embodiments, the method can include injecting the at least one injectable agent into one or more lines, wrinkles or folds on an individual's face, e.g., as part of a cosmetic treatment. Block 1710 depicts optionally injecting the at least one injectable agent into the underlying tissue of one or more of a forehead, a glabella, a periorbital region, a preauricular region, an ear, a cheek, a lip, a nasolabial fold, a labial region, a perilablial region, a sublabial region, a labiomental crease, or a neck region of the individual. For example, the method can include using the wearable injection guide to inject one or more doses of collagen into one or more of the nasolabial folds of an individual's face.

FIG. 18 shows further aspects of the method illustrated in FIG. 13 for administering an injection treatment to an individual with a wearable injection guide. FIG. 18 illustrates that in some embodiments, block 1310 can include one or more of optional blocks 1800, 1810, 1820, 1830, 1840, and 1850. Block 1800 depicts optionally injecting at least one neurotoxin. In some embodiments, the at least one neurotoxin can include one or more forms of the neuromuscular blocking agent botulinum toxin. In some embodiments, at least one botulinum toxin is used for treating wrinkles in a facial region of an individual. For example, the wearable injection guide can be used to guide injection of at least one botulinum toxin into wrinkles associated with the forehead, e.g., glabellar frown lines, of an individual's face. In some embodiments, at least one botulinum toxin is used in conjunction with the wearable injection guide to treat one or more of primary axillary hyperhidrosis (excessive sweating), blepharospasm (eye twitching), strabismus (cross-eyed), cervical dystonia, chronic migraine, and upper limb spasticity. Non-limiting examples of botulinum toxin for use as an injectable agent include onabotulinumtoxinA, ab otulinumtoxinA, incobotulinymtoxinA, rimabotulinumtoxinB and like agents (see, e.g., Park et al., *Clin. Ophthalmol.* (2011) 5:725-732, which is incorporated herein by reference).

Block 1810 of FIG. 18 depicts optionally injecting at least one of a subcutaneous volume enhancer or dermal filler. Block 1810 further includes optional blocks 1820, 1830, and 1840. Block 1820 illustrates optionally injecting at least one collagen filler into an underlying tissue of the body region of the individual. For example, the wearable injection guide can be used to guide injection of at least one collagen filler into the upper or lower lip of an individual to achieve lip augmentation. Other non-limiting examples of injecting collagen filler include injecting into the grooves and/or lines that form wrinkles and sagging skin of the face. In some embodiments, the at least one collagen filler can be used to treat depressed scars, e.g., pitted acne scars. Non-limiting examples of bovine-, porcine-, or human-derived collagen fillers include Artefill, Cosmoplast/Cosmoderm, Evolence, and Zyderm/Zyplast. For example, Zyplast can be injected using a 30-gauge needle into the middle and deep reticular dermis to correct deeper lines and wrinkles or for lip augmentation. In some embodiments, the collagen filler can be combined with one or more other agents such as, for example, botulinum toxin or an analgesic. A non-limiting example of a collagen filler combined with another agent includes Zyderm which includes lidocaine as an analgesic. Collagen fillers can be used for wrinkles, fine lines, deep folds, and lip augmentation. The depth of injection can vary from superficial/papillary dermis for treatment of wrinkles and fine lines to mid to deep dermis for treatment of moderate to deep facial wrinkles and folds (see, e.g., Hanke et al., *J. Am. Acad. Dermatol.* (2011) 64:S66-85, which is incorporated herein by reference).

Block 1830 of FIG. 18 depicts optionally injecting at least one hyaluronic acid filler into an underlying tissue of the body region of the individual. For example, injecting at least one hyaluronic acid filler can be used to temporarily smooth wrinkles, augment lips, reduce facial folds, and attenuate scars. Non-limiting examples of hyaluronic fillers include Belotero Balance (from Merz Aesthetics); Hyalaform, Juvederm Ultra and Juvederm Ultra Plus (from Allergan, Inc.); Perlane and Restylane (from Medicis Aesthetics Inc.) PREVELLE and Puragen (from Mentor Corp.).

Hyaluronic acid can be injected with needles ranging in size from 27 to 30 gauge to a depth ranging from the mid to deep dermis to the superficial subcutaneous space (see, e.g., Allemann & Baumann *Clinical Interventions in Aging* (2008) 3:629-634; Brant & Cazzaniga *Clinical Interventions in Aging* (2008) 3:153-159, which are incorporated herein by reference).

Figure 18:
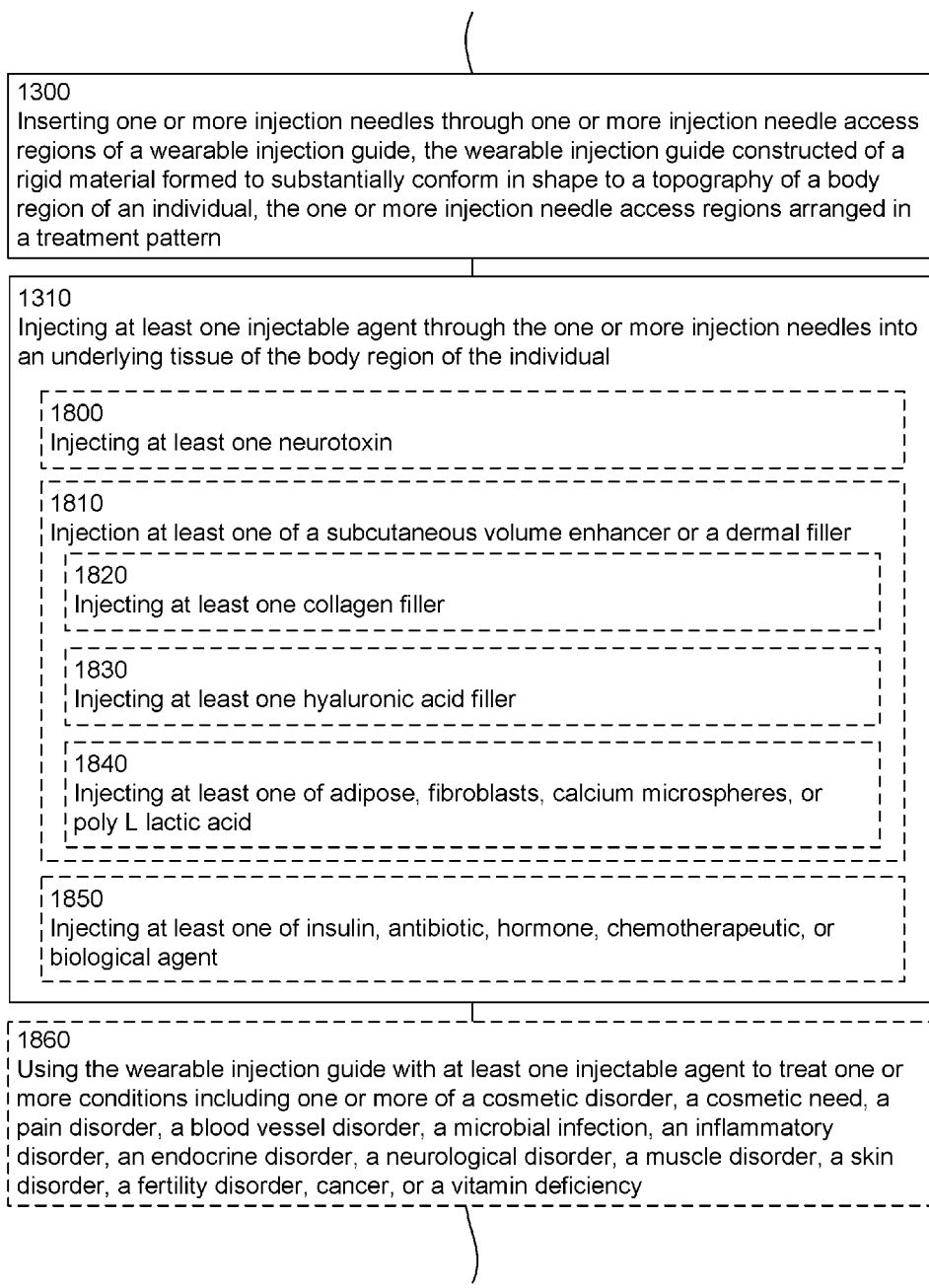
FIG. 18 is a flowchart showing aspects of a method such as depicted in FIG. 13.

Block 1840 of FIG. 18 depicts optionally injecting at least one of adipose, fibroblasts, calcium microspheres, or poly L lactic acid into an underlying tissue of the body region of the individual. In some embodiments, adipose tissue can be isolated from one region of the individual's body, e.g., the abdomen or thigh, and reinjected into another region of the individual's body, e.g., the face, to augment or repair features of the facial region (see, e.g., Meier et al., *Arch. Facial Plast. Surg.* (2009) 11:24-28, which is incorporated herein by reference). In some embodiments, fibroblasts can be isolated from the individual, expanded in vitro, and reinjected into the individual (see, e.g., U.S. Pat. No. 7,846,465, which is incorporated herein by reference). In some embodiments, calcium hydroxyapatite microspheres (e.g., Radiesse®; BioForm Medical, Inc., San Mateao, Calif.) can be injected using a 27 gauge needle, e.g., to correct moderate to severe nasolabial folds. The calcium hydroxyapatite microspheres can be injected with an aqueous gel, the latter of which is highly viscous, requiring a larger bore needle, e.g., a 27 gauge needle. The gel degrades over the course of several months, leaving behind the calcium microspheres to stimulate collagen synthesis. In some embodiments, poly L lactic acid (PLLA, e.g., Sculptra®; Dermik Laboratories, Bridgewater, N.J.) can be injected at or below the level of the dermal-subcutaneous junction for augmentation of the lower two-thirds of the face in individuals with lipoatrophy associated with HIV infection. PLLA can also be used for cosmetic purposes as a deep dermal filler (see, e.g., Sherman *Clin. Dermatol.* (2009) 27:S23-S32, which is incorporated herein by reference). PLLA is viscous solution and as such requires injection using larger bore needles, e.g., 25- or 26-gauge needles. In some embodiments, PLLA may be used in conjunction with lidocaine and/or epinephrine to lessen the pain of injection with a relatively large needle. For example, lidocaine and/or epinephrine can be included in the injection needle along with the PLLA. In some embodiments, lidocaine and/or epinephrine may be included as part of the wearable injection guide, e.g., as a coating on the inner surface of the wearable injection guide.

Block 1850 of FIG. 18 depicts optionally injecting at least one of insulin, an antibiotic, a hormone, a chemotherapeutic, or a biological agent into an underlying tissue of the body region of the individual. In some embodiments, injecting at least one of insulin includes injecting at least one of a rapid acting insulin, short-acting insulins, intermediate-acting insulins, premixed insulins, or long-acting insulins. Commercial sources of insulin are available from, e.g., Eli Lilly (Indianapolis, Ind.), Sanofi-Aventis (Bridgewater N.J.), Novo Nordisk Inc. (Princeton, N.J.), or Pfizer (New York, N.Y.). In some embodiments, injecting at least one antibiotic includes injecting at least one of penicillins, e.g., penicillin, ampicillin, piperacillin; cephalosporins and other beta-lactam drugs, e.g., cefazolin, ertapenem; tetracyclines, e.g., doxycycline; macrolides, e.g., erythromycin; clindamycin; aminoglycosides, e.g., streptomycin, gentamicin; spectino-mycin; sulfonamides; quinolones and fluoroquinolones. In some embodiments, injecting at least one hormone includes injecting at least one of a hypothalamic or pituitary hormone, synthetic analogs, and/or antagonist thereof, e.g., adrenocorticotropic hormone, corticotropin-releasing hormone, follicle stimulating hormone, gonadotropin-releasing hormone and synthetic analogs, luteinizing hormone, pro-lactin; at least one of an adrenocoricosteroid, synthetic analogs, and/or antagonists thereof, e.g., dexamethasone, hydrocortisone, prednisolone, methylprednisolone, triamicinolone; gonadal hormones, e.g., estrogens, progestins, androgens, and anabolic steroids; glucagon and analogs thereof. In some embodiments, injecting at least one cancer chemotherapeutic or associated therapy includes injecting at least one of alpha interferon, erythropoietin and derivatives thereof, colony stimulating factor and analogs thereof, somatostatin and analogs thereof. In some embodiments, injecting at least one biological agent includes injecting at least one of teriparatide, etanercept, interferon, abatacept, anakinra, bevacizumab, cetuximab, cyclophosphamide, gemtuzumab, muromonab-CD3, omalizumab, pegademase, immune globulin, tacrolimus, or tositumomab.

In some embodiments, injecting the at least one injectable agent through the one or more injection needles into an underlying tissue of the body region of an individual includes injecting at least one injectable agent in combination with one or more analgesic agents, for example lidocaine, to lessen the pain associated with injection.

Block 1860 of FIG. 18 depicts further aspects of the method of FIG. 13 for administering an injection treatment to an individual with a wearable injection guide. block 1860 illustrates optionally using the wearable injection guide with at least one injectable agent to treat one or more conditions including one or more of a cosmetic disorder, a cosmetic need, a pain disorder, a blood vessel disorder, a microbial injection, an inflammatory disorder, an endocrine disorder, a neurological disorder, a muscle disorder, a skin disorder, a fertility disorder, cancer, or a vitamin deficiency.

Figure 19:
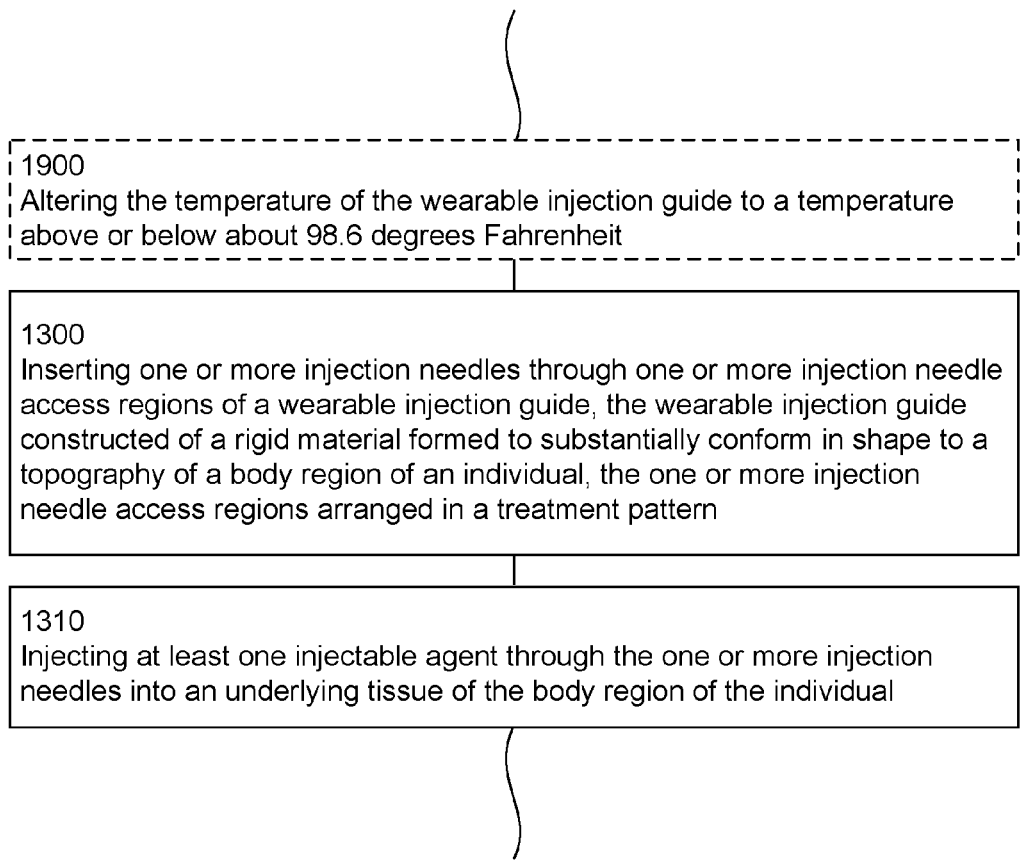
FIG. 19 is a flowchart depicting aspects of a method such as illustrated in FIG. 13.

FIG. 19 shows further aspects of the method illustrated in FIG. 13 for administering an injection treatment to an individual with a wearable injection guide. FIG. 19 illustrates that in some embodiments, the method can include block 1900. Block 1900 depicts altering the temperature of the wearable injection guide to a temperature above or below about 98.6° F. (or above or below about 37° C.).

In some embodiments, the wearable injection guide is cooled below about 98.6° F. (37° C.) prior, during and/or after injection with an injectable agent. Cooling the body region may lessen the pain associated with injecting the one or more injection needles and/or prevent swelling and/or bruising post injection. In some embodiments, the wearable injection guide is cooled by placing the wearable injection guide in a cooling device prior to placement onto a body region of an individual. For example, the wearable injection guide can be stored in a cooling device until use. Alternatively, the wearable injection guide can be placed into the cooling device just prior to use for a sufficient time to cool the wearable injection guide to an appropriate temperature. The cooling temperature can range from about 10° C. to about 0° C. It is understood that the cooling temperature can fall outside this range, but is contemplated to be sufficiently cool enough to reduce pain and swelling but not so cold as to be painful to the underlying tissue of the body region. Non-limiting examples of cooling devices for this purpose include a refrigerator, a freezer, or an ice bath. In some embodiments, cooling the wearable injection guide can include using a cooling mechanism associated with the wearable injection guide, e.g., a chemical or thermoelectric cooling mechanism as discussed above herein.

In some embodiments, the wearable injection guide is heated above about 98.6° F. (37° C.) prior, during and/or after injection with an injectable agent. Heating the body region covered by the wearable injection guide may increase vasodilation and/or circulation in the underlying tissue. In some embodiments, the wearable injection guide is heated by placing the wearable injection guide in a heating device prior to placement onto a body region of an individual. For example, the wearable injection guide can be stored in a heating device until use. Alternatively, the wearable injection guide can be placed into the heating device just prior to use for a sufficient time to heat the wearable injection guide to an appropriate temperature. The heating temperature can range from about 40° C. to about 45° C. It is understood that the heating temperature can fall outside this range, but is contemplated to be sufficiently hot enough to increase circulation but not so hot as to be painful or damaging to the underlying tissue of the body region. Non-limiting examples of heating devices for this purpose include a warming oven, a microwave, or hot water bath. In some embodiments, heating the wearable injection guide can include using a heating mechanism associated with the wearable injection guide, e.g., a chemical or thermoelectric heating mechanism as discussed above herein.

FIG. 20 illustrates a method of administering an injection treatment to an individual with a wearable injection guide, the wearable injection guide including a rigid needle-penetrable material with an inner surface and an outer surface, the inner surface having a form fitting contour substantially conforming to the topography of the body region of the individual and the outer surface having one or more fiducials indicative of at least one treatment parameter. Block 2000 shows aligning one or more alignment marks of a wearable injection guide with one or more reference points on a body region of an individual. Block 2010 depicts immobilizing the wearable injection guide on the body region of the individual. Block 2020 depicts inserting one or more injection needles through the rigid needle-penetrable material of the wearable injection guide at or near the one or more fiducials. Block 2030 depicts injecting at least one injectable agent from the one or more injection needles into an underlying tissue of the body region of the individual.

Figure 21:
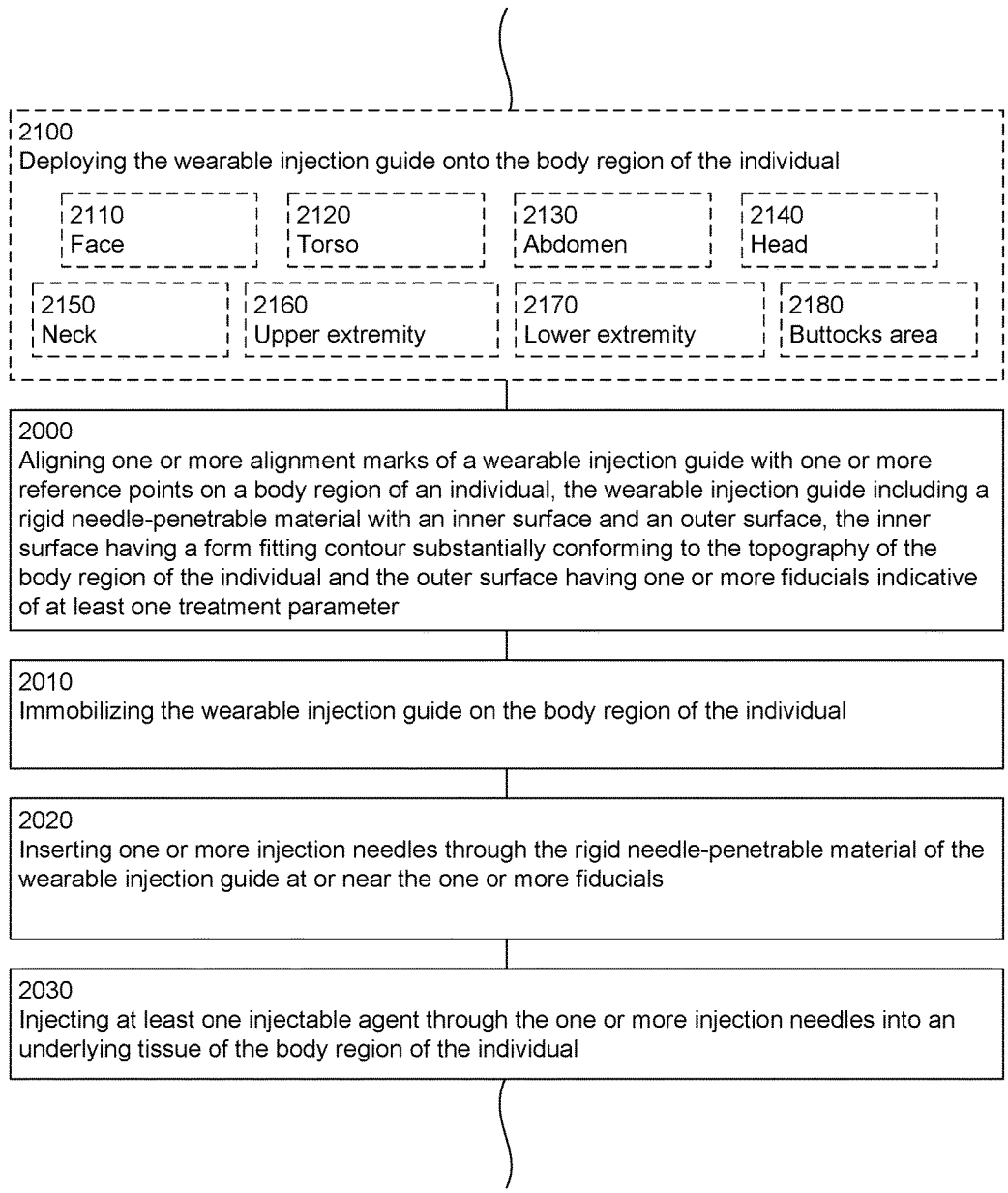
FIG. 21 is a flowchart illustrating aspects of a method such as shown in FIG. 20.

FIG. 21 illustrates further aspects of the method of FIG. 20. FIG. 21 illustrates that in some embodiments, the method of FIG. 20 can include the optional step of block 2100. Block 2100 depicts deploying the wearable injection guide onto the body region of the individual. Block 2100 further includes the optional steps of deploying the wearable injection guide onto the body region of a face of the individual as illustrated in block 2110; onto the body region of a torso of the individual as illustrated in block 2120; onto the body region of an abdomen of the individual as illustrated in block 2130; onto the body region of a head of an individual as illustrated in block 2140; onto the body region of a neck of the individual as illustrated in block 2150; onto the body region of an upper extremity area of the individual as illustrated in block 2160; onto the body region of a lower extremity area of the individual as illustrated in block 2170; or onto the body region of a buttocks area of the individual as illustrated in block 2180. The deployment of the wearable injection guide on a specific body region of the individual is dependent upon the condition being treated and the treatment regimen. For example, specific treatment of the individual's face or the individual's neck would necessarily include a wearable injection guide specifically designed for use on a face or neck, respectively. In another example, a self-injection treatment regimen that includes intramuscular injections, e.g., antibiotic or fertility treatment, may include a wearable injection guide designed for use on any of a number of body regions easily accessible to the individual, e.g., the thigh or abdomen areas.

FIG. 22 illustrates further aspects of the method of FIG. 20. In some embodiments, aligning one or more alignment marks of a wearable injection guide with one or more reference points on a body region of an individual can include aligning the one or more alignment marks with one or more reference marks placed on the body region of the individual by the individual, a physician, or other person with, for example, a washable ink. In some embodiments, the one or more reference points represent permanent features of the body region. Block 2000 further includes optional block 2200. Block 2200 depicts optionally aligning the one or more alignment marks of the wearable injection guide with one or more topographical landmarks on the body region of the individual. Block 2200 can optionally include block 2210. Block 2210 depicts optionally aligning the one or more alignment marks of the wearable injection guide with one or more pigmentation, pigmented area, skin texture pattern, tattoo, blemish, scar, anatomical feature, or subsurface blood vessel of at least at portion of the body region of the individual. Two and preferably three or more reference points are used to align the wearable injection guide onto the body region of the individual.

Returning to FIG. 20, in some embodiments, the method for administering an injection treatment to an individual with a wearable injection guide including immobilizing the wearable injection guide on the body region of the individual, as illustrated in block 2010, can include adhering the wearable injection guide on the body region of the individual with a reversible adhesive. In some embodiments, the reversible adhesive is included on the inner surface of the wearable injection guide. In some embodiments, the reversible adhesive is applied to the inner surface of the wearable injection guide and/or the body region of the individual just prior to deploying the wearable injection guide. In some embodiments, immobilizing the wearable injection guide on the body region of the individual, as illustrated in block 2010, can include immobilizing the wearable injection guide on the body region of the individual with one or more body portion-encircling pieces.

Returning to FIG. 20, in some embodiments, the method for administering an injection treatment to an individual with a wearable injection guide including inserting one or more injection needles through the rigid needle-penetrable material of the wearable injection guide at or near the one or more fiducials, as illustrated in block 2020, can include inserting the one or more injection needles at a 90 degree angle relative to the outer surface of the wearable injection guide. In some embodiments, injecting the one or more needles containing at least one injectable agent through the rigid needle-penetrable material of the wearable injection guide at or near the one or more fiducials, as illustrated in block 2020, can include inserting the one or more injection needles at less than a 90 degree angle relative to the outer surface of the wearable injection guide. In some embodiments, all insertions of the one or more injection needles through the wearable injection guide are done at either 90 degrees or less than 90 degrees. In some embodiments, the insertions of the one or more injection needles through the wearable injection guide can vary from 90 degrees or less. The angle of the needle insertion will be dependent upon the injectable agent, the needle depth, and the portion of the body region being injected. For example, intramuscular injection with penicillin, e.g., may be injected at 90 degree, i.e., straight through the wearable injection guide. In contrast, subcutaneous injections with collagen filler, e.g., may be injected at less than 90 degrees, i.e., at an angle relative to the outer surface of the wearable injection guide.

Figure 23:
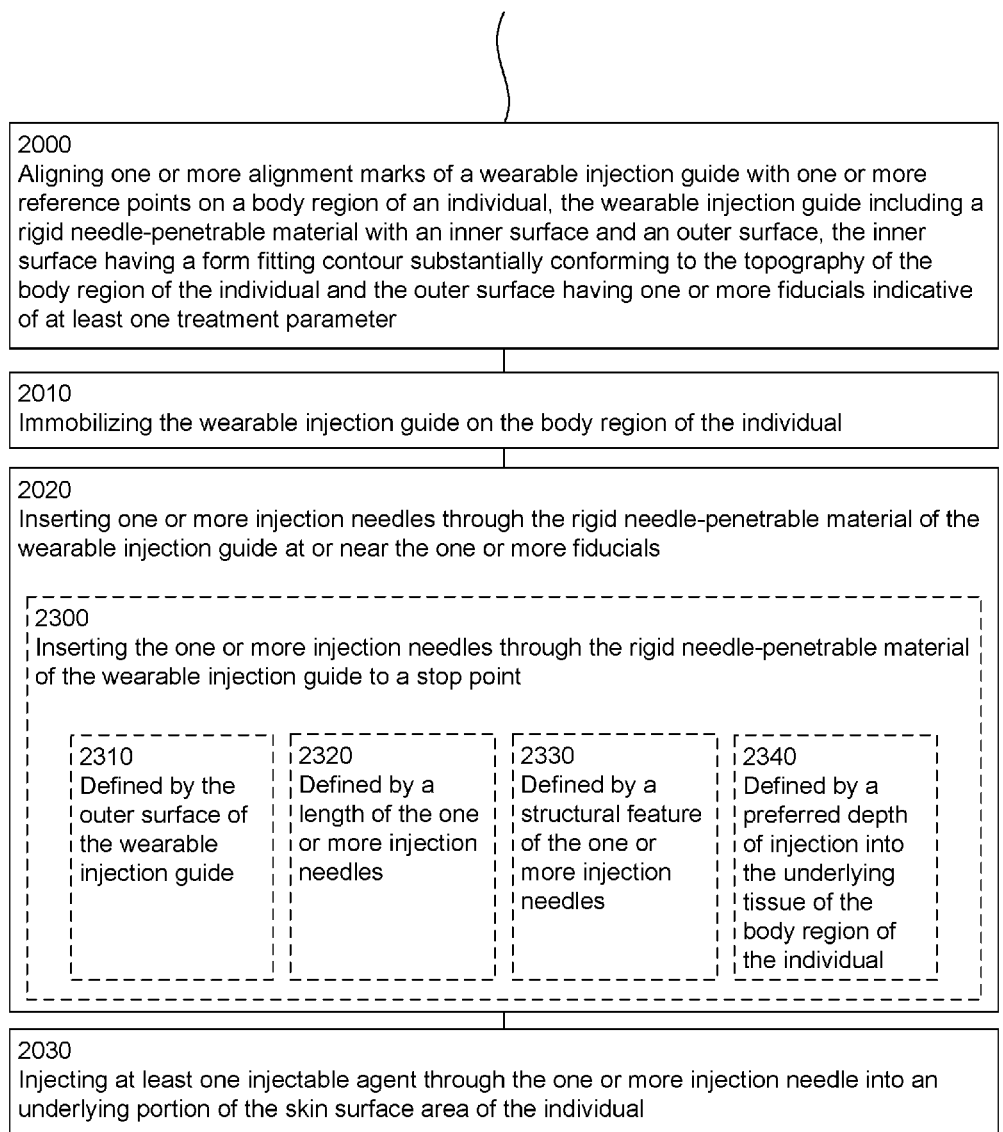
FIG. 23 is a flowchart depicting aspects of a method such as illustrated in FIG. 20.

FIG. 23 illustrates further aspects of the method of FIG. 20. FIG. 23 illustrates that in some embodiments, the method of FIG. 20 can optionally include block 2300. Block 2300 depicts optionally inserting the one or more injection needles through the needle-penetrable material of the wearable injection guide to a stop point. Block 2300 can optionally include blocks 2310, 2320, 2330, or 2340. Block 2310 depicts optionally inserting the one or more injection needles through the rigid needle-penetrable material of the wearable injection guide to a stop point defined by the outer surface of the wearable injection guide. For example, the outer surface may be separated from the inner surface of the wearable injection guide by a thickness of rigid needle-penetrable material that limits how far an injection needle of a given length can be inserted through the wearable injection guide and into the underlying tissue of the body region. Block 2320 depicts optionally inserting the one or more injection needles through the rigid needle-penetrable material of the wearable injection guide to a stop point defined by a length of the one or more injection needles. For example, standard injection needles can range in length from ³⁄₁₆ inches (5 mm) to 1½ inches (38 mm) from the tip of the needle bevel to the needle hub. The choice of injection needle will also be dependent upon how deep the injection is intended to go. For example, needles ranging in length from ½ inch to ⅝ inch can be used for subcutaneous injections while needles ranging in length from 1 inch to 1½ inch can be used for intramuscular injections. Furthermore, the needle length may also be considered in the context of the desired needle depth required and the thickness of the wearable injection guide. Block 2330 depicts optionally inserting the one or more injection needles through the rigid needle-penetrable material of the wearable injection guide to a stop point defined by a structural feature of the one or more injection needles. For example, the stop point may be defined by a structural feature of the one or more injection needles, e.g., the needle hub or the attached syringe. The rigid needle-penetrable material of the wearable injection guide may allow for penetration of a sharp injection needle, but inhibits further insertion of the injection needle once the needle hub or attached syringe reaches the outer surface of the wearable injection guide. Block 2340 depicts optionally inserting the one or more injection needles through the rigid needle-penetrable material of the wearable injection guide to a stop point defined by a preferred depth of injection into the underlying tissue of the body region of the individual. For example, a physician, other practitioner, or the individual may have knowledge as to how deep an injection needle should be injected based on the type of injectable agent being injected and the location of the injection. In some embodiments, the one or more fiducials on the outer surface of the wearable injection guide may provide guidance as to the injection depth and/or length of needle for use at any given injection site.

Figure 24:
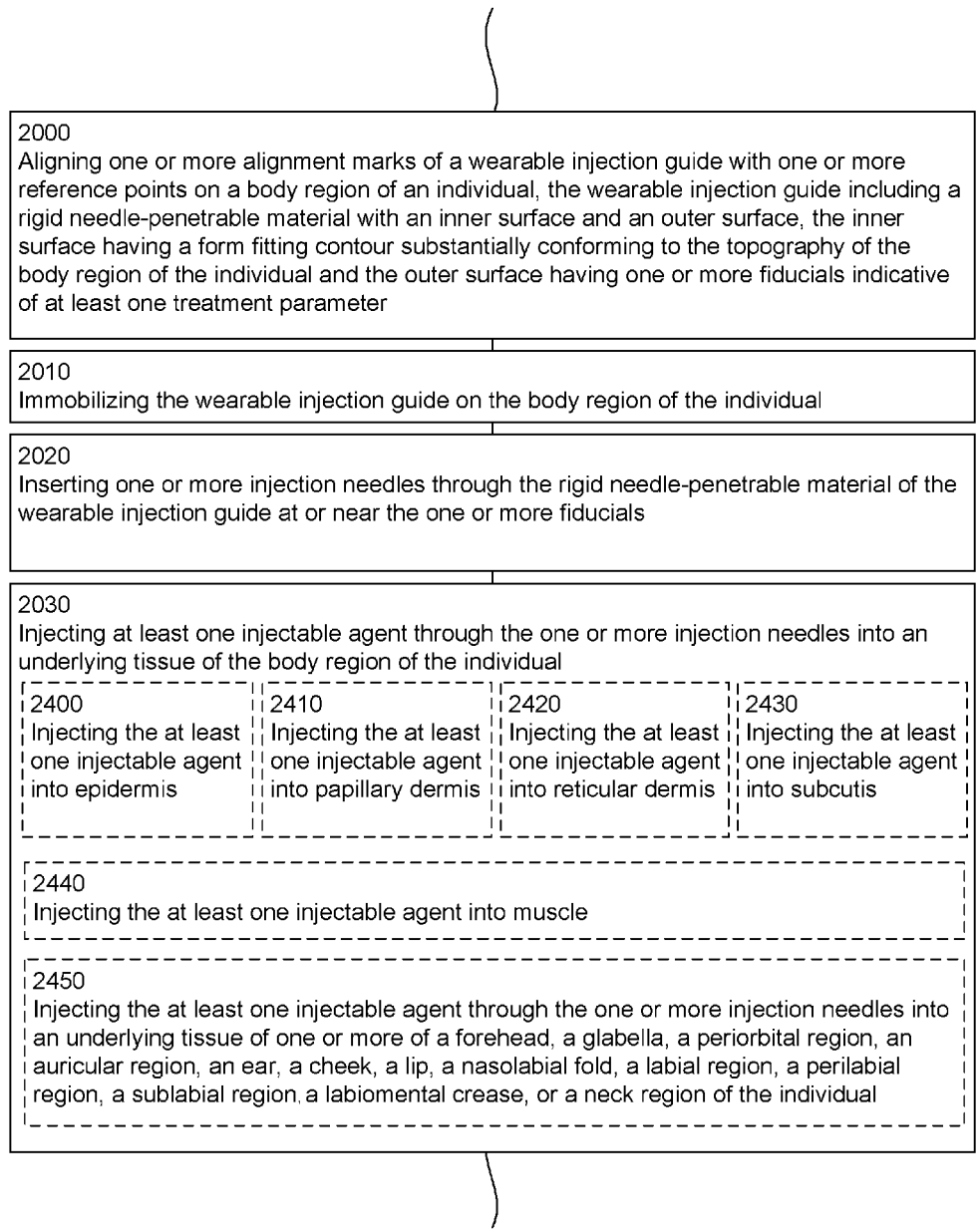
FIG. 24 is a flowchart illustrating aspects of a method such as shown in FIG. 20.

FIG. 24 illustrates further aspects of the method of FIG. 20. FIG. 24 illustrates that in some embodiments, the method of FIG. 20 including injecting at least one injectable agent through the one or more injection needles into the underlying tissue of the body region of the individual optionally includes blocks 2400, 2410, 2420, 2430, or 2440. Block 2400 depicts optionally injecting the at least one injectable agent into epidermis. Block 2410 depicts optionally injecting the at least one injectable agent into papillary dermis. Block 2420 depicts optionally injecting the at least one injectable agent into reticular dermis. Block 2430 depicts optionally injecting the at least one injectable agent into subcutis. Block 2440 depicts optionally injecting the at least one injectable agent into muscle. Block 2030 optionally includes block 2450. Block 2450 depicts optionally injecting the at least one injectable agent into a forehead, a glabella, a periorbital region, an auricular region, an ear, a cheek, a lip, a nasolabial fold, a labial region, a perilabial region, a sublabial region, a labiomental crease, or a neck region of the individual. The depth to which a needle is injected is dependent on the condition being treated and the injectable agent being injected, as discussed above herein.

FIG. 25 illustrates further aspects of the method of FIG. 20. FIG. 25 illustrates that in some embodiments, the method of FIG. 20 including injecting the at least one injectable agent from the one or more injection needles into the underlying tissue of the body region of the individual optionally includes blocks 2500, 2510, 2520, 2530, or 2540. Block 2500 depicts optionally injecting at least one neurotoxin, non-limiting examples of which have been described above herein. Block 2510 depicts optionally injecting at least one of a subcutaneous volume enhancer or dermal filler. Block 2510 further optionally includes blocks 2520, 2530, and 2540. Block 2520 depicts optionally injection at least one of a collagen filler, non-limiting examples of which have been described above herein. Block 2530 depicts optionally injecting at least one of a hyaluronic acid filler, non-limiting examples of which have been described above herein. Block 2540 depicts optionally injecting at least one of adipose, fibroblasts, calcium microspheres, or poly L lactic acid, non-limiting examples of which have been described above herein. Block 2030 further optionally includes block 2550 which depicts optionally injecting at least one of insulin, antibiotic, hormone, chemotherapeutic, or biological agent, non-limiting examples of which have been described above herein.

Figure 26:
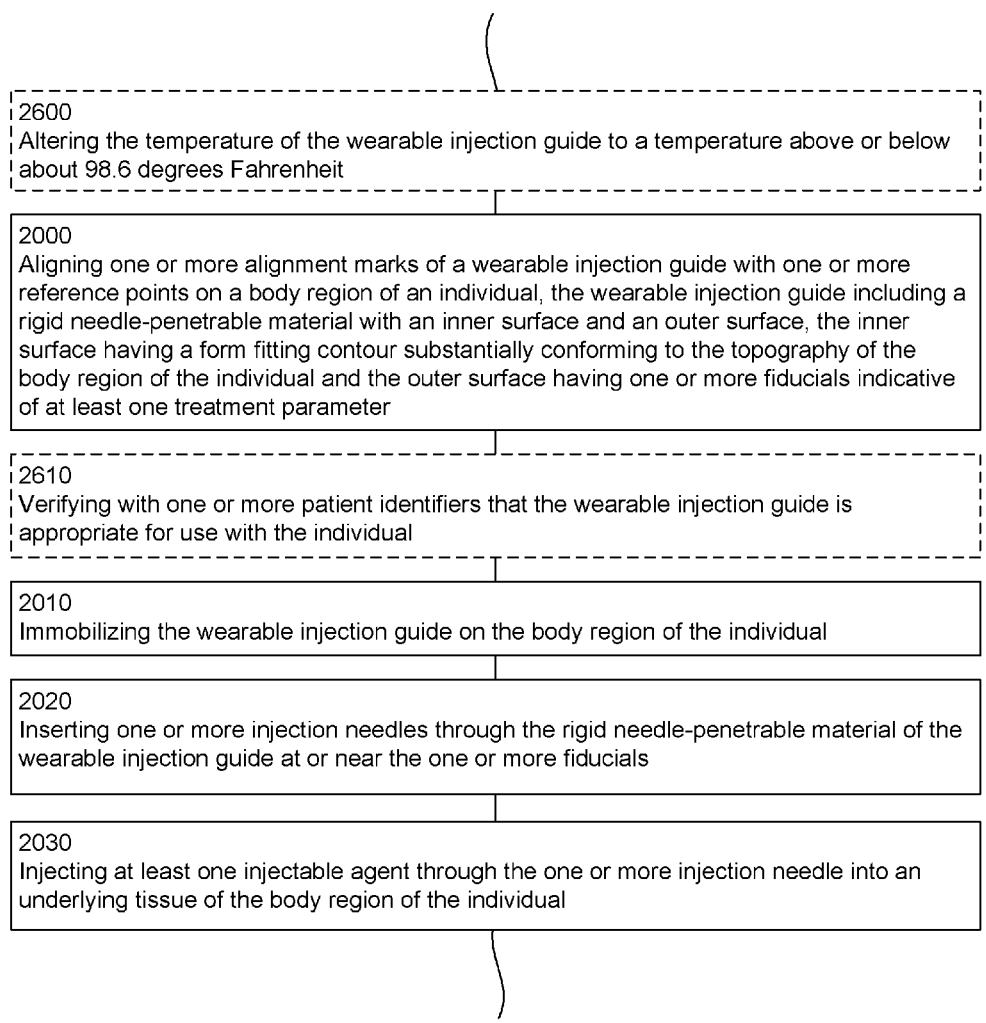
FIG. 26 is a flowchart depicting aspects of a method such as illustrated in FIG. 20.

FIG. 26 illustrates further aspects of the method of FIG. 20. FIG. 26 illustrates that in some embodiments, the method of FIG. 20 for administering an injection treatment to an individual with a wearable injection guide can optionally include blocks 2600 and/or 2610. Block 2600 depicts optionally altering the temperature of the wearable injection guide to a temperature above or below about 98.6° F. Cooling the wearable injection guide before and/or during the injection treatment and consequently cooling the body region upon which the wearable injection guide is deployed can reduce the pain of injection and/or reduce swelling or bruising associated with injection. Heating the wearable injection guide before and/or during the injection treatment and consequently heating the body region upon with the wearable injection guide is deployed can increase vascular dilation and blood circulation. In some embodiments, the wearable injection guide is heated or cooled by placing the guide into a heating or cooling device, respectively, prior to deployment on the individual. In some embodiments, the wearable injection guide has a thermal-regulating mechanism that allows it to heat or cool, e.g., a chemical or thermoelectric mechanism as discussed above herein.

Block 2610 of FIG. 26 depicts optionally verifying with one or more patient identifiers that the wearable injection guide is appropriate for use with the individual. In some embodiments, the one or more patient identifiers can include a bar code or RFID tag that is specific to the individual and is read prior to or after deployment of the wearable injection guide onto the body region of the individual. In some embodiments, the one or more patient identifiers can include one or more reference points on the body region of the individual. The ability to align one or more alignment marks on the wearable injection guide with one or more reference points on the body region of the individual, e.g., a unique pattern of topographical landmarks, can be used to determine if the wearable injection guide is appropriate for use for the individual. In some embodiments, other forms of patient identifiers can be used, non-limiting examples of which include vein pattern recognition, facial recognition, iris recognition, or voice recognition. In some embodiments, verifying with one or more patient identifiers that the wearable injection guide is appropriate for use on the individual can be done using one or more skin measurements, e.g., skin thickness, melanin measurement, skin surface pH, skin roughness, skin conductance, sweat ducts, sebum secretions, and the like (see, e.g., Wa & Maibach *Skin Res. Technol.* (2010) 16:38-54, U.S. Patent Application 2008/0166029, which are incorporated herein by reference). In some embodiments, the one or more patient identifiers can be assessed using one or more sensors incorporated into the wearable injection guide. Some examples of biometric sensor, for example, are described in U.S. Patent Application 2008/0262376, which is incorporated herein by reference.

The method of FIG. 20 further includes using the wearable injection guide with at least one injectable agent to treat one or more conditions, non-limiting examples of which include one or more of a cosmetic disorder, a cosmetic need, a pain disorder, a blood vessel disorder, a microbial infection, an inflammatory disorder, an endocrine disorder, a neurological disorder, a muscle disorder, a skin disorder, a fertility disorder, cancer, or a vitamin deficiency.

Figure 27:
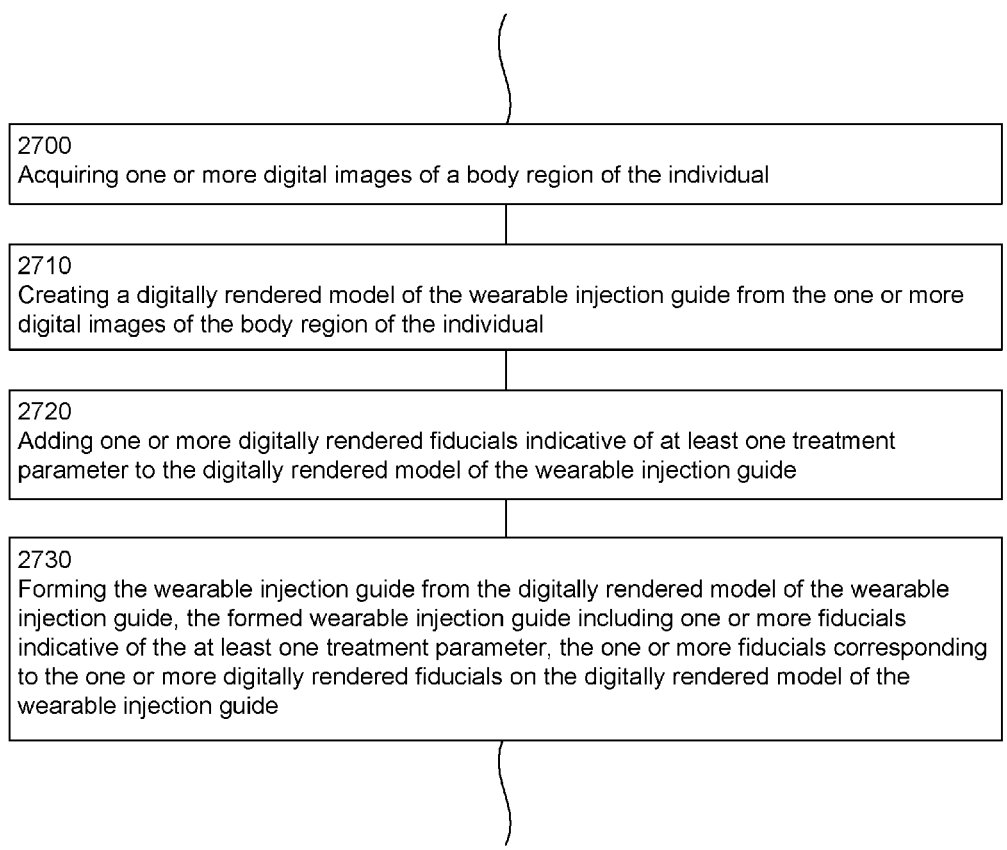
FIG. 27 is a flowchart of a method of generating a wearable injection guide.

FIG. 27 illustrates a method of generating a wearable injection guide for an individual. Block 2700 shows acquiring one or more digital images of a body region of the individual. As defined herein, digital images includes any digital information related to the body region and the underlying tissue. In some embodiments, acquiring one or more digital images of the body region of an individual includes acquiring one or more images of the surface topography of the body region. In some embodiments, one or more contact scanners can be used to acquire one or more digital images of the body region of an individual by running a probe over the surface of the body region. In some embodiments, one or more non-contact scanners can be used to acquire one or more digital images of the body region of an individual by measuring reflected or deflected radiation or light from the body region. In some embodiments, the one or more digital images of a body region of the individual can be acquired using one or more of an image capture system, e.g., a digital camera. In some embodiments, the one or more images can be captured using one or more of a laser scanner in combination with one or more charge-coupled device. Block 2710 depicts creating a digitally rendered model of the wearable injection guide from the one or more digital images of the body region of the individual. For example, surface scanning software can be used to import individual points of the body region, e.g., of the face, and then combine them in the X, Y, and Z axes to render a three-dimensional representation of the topography of the body region. The three-dimensional representation of the topography of the body region can be combined with information regarding the final thickness of the wearable injection guide, e.g., uniform or variable, to create the digitally rendered model of the wearable injection guide. Any of a number of modeling programs can be used for this purpose, as will be described below. Block 2720 illustrates adding one or more digitally rendered fiducials indicative of a treatment parameter to the digitally rendered model of the wearable injection guide. The one or more digitally rendered fiducials can include one or more colors, letters, shapes, numbers, crosshairs, or combinations thereof. Block 2730 illustrates forming the wearable injection guide from the digitally rendered model of the wearable injection guide, the formed wearable injection guide including one or more fiducials indicative of the at least one treatment parameter, the one or more fiducials corresponding to the one or more digitally rendered fiducials on the digitally rendered model of the wearable injection guide. For example, forming the wearable injection guide can include using a three-dimensional printing technology. The at least one treatment parameter can include one or more injectable agents to be injected at said one or more fiducials, one or more dosages of one or more injectable agents to be injected at said one or more fiducials, and the depth of the needle injection for injecting one or more injectable agents at said one or more fiducials.

Figure 28:
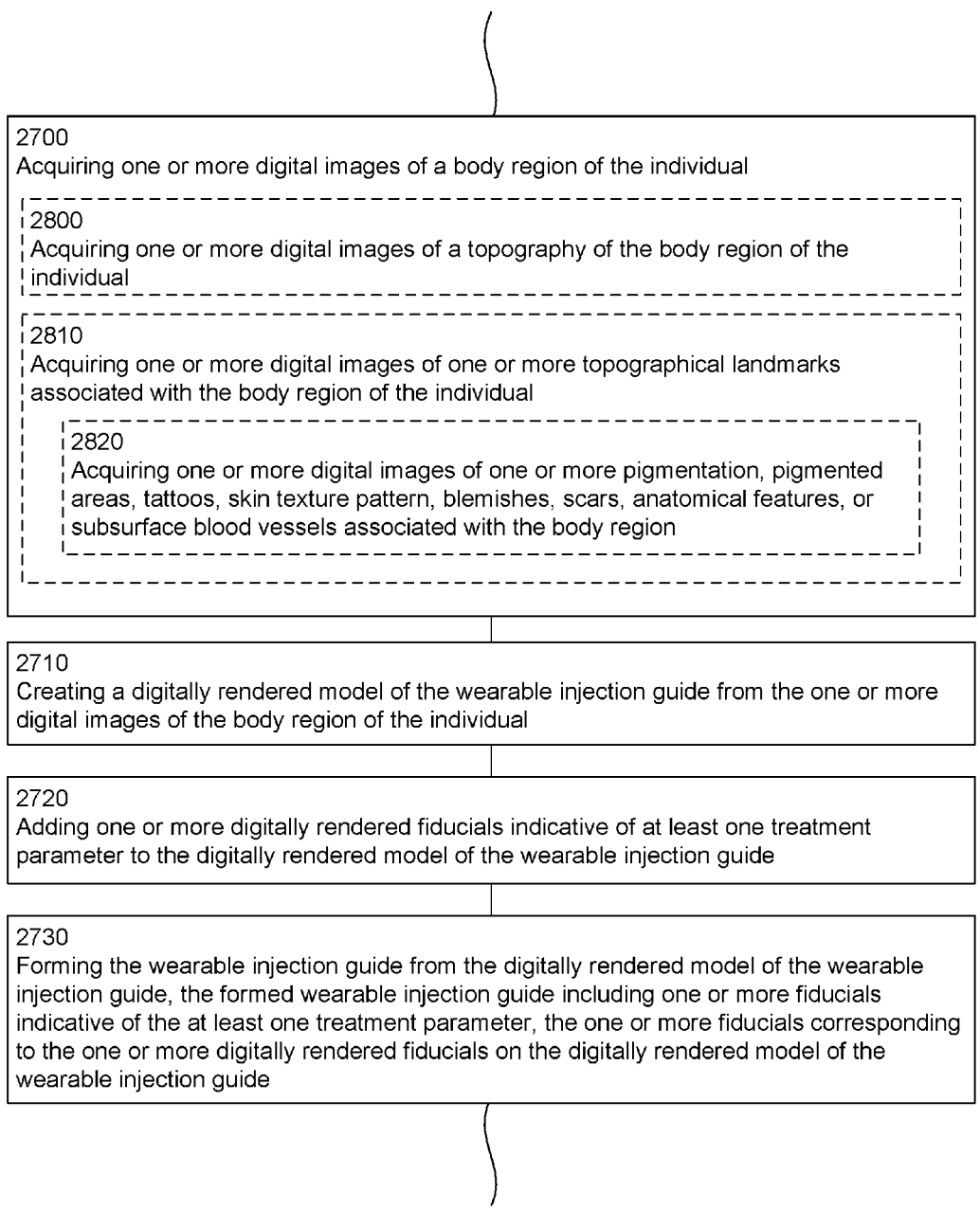
FIG. 28 is a flowchart illustrating aspects of a method such as shown in FIG. 27.

FIG. 28 shows further aspects of the method of FIG. 27. FIG. 28 shows optional steps in blocks 2800, 2810, and 2820 for acquiring one or more digital images of the body region of the individual. Block 2800 depicts optionally acquiring one or more digital images of the topography of the body region of the individual. The topography of the body region can include both the micro-topography, e.g., the texture and/or pattern of the skin surface, and the macro-topography, e.g., anatomical features such as nose, lips, cheeks, large wrinkle, joints, and the like.

Block 2810 depicts optionally acquiring one or more digital images of one or more topographical landmarks associated with the body region of the individual. Block 2820 further depicts optionally acquiring one or more digital images of one or more pigmentation, pigmented areas, tattoos, skin texture pattern, blemishes, scars, anatomical features, or subsurface blood vessels associated with the body region.

In some embodiments, the one or more digital images of one or more topographical landmarks associated with the body region of the individual can include one or more reference points for aligning the wearable injection guide to the body region of the individual. The one or more reference points observed in the one or more digital images can be used to determine where alignment marks should be added to the digitally rendered model of the wearable injection guide prior to manufacture.

In some embodiments, the one or more digital images of one or more topographical landmarks associated with the body region of the individual can include features of the body region that are themselves the focus of treatment, for example a scar (e.g., an acne scar) or other blemish on the surface of the skin. For example, one or more digital images of a scar on the body region can aide in determining where the one or more digitally rendered fiducials indicative of a treatment parameter should be added to the digitally rendered model of the wearable injection guide. As an example, injectable dermal fillers can be used to raise depressions in the surface of the skin caused by severe acne scarring.

In some embodiments, the one or more digital images of one or more topographical landmarks associated with the body region of the individual can include features contraindicated as sites of injection. For example, injecting a neurotoxin, e.g., botulinum toxin, or other injectable agents directly into a blood vessel may lead to unwanted systemic complications. As such, a treatment regimen that includes botulinum toxin injection, for example, would necessarily avoid overlaying the one or more fiducials on the wearable injection guide with one or more blood vessels associated with the body region of the individual. In an embodiment, one or more of the superficial blood vessels on the body region of the individual can be imaged and incorporated into the digitally rendered model of the wearable injection guide.

Non-limiting examples of non-invasive imaging techniques for superficial blood vessels include photoacoustic imaging, ultrasound, near-infrared imaging (see, e.g., Wieringa et al., *Ann Biomed Eng* (2006) 34:1870-1878, which is incorporated herein by reference). Images of superficial blood vessels generated using one or more of these methods can be combined with the images of the topography of the body region of the individual to aid in adding the one or more digitally rendered fiducials to the digitally rendered model of the wearable injection guide.

Figure 29:
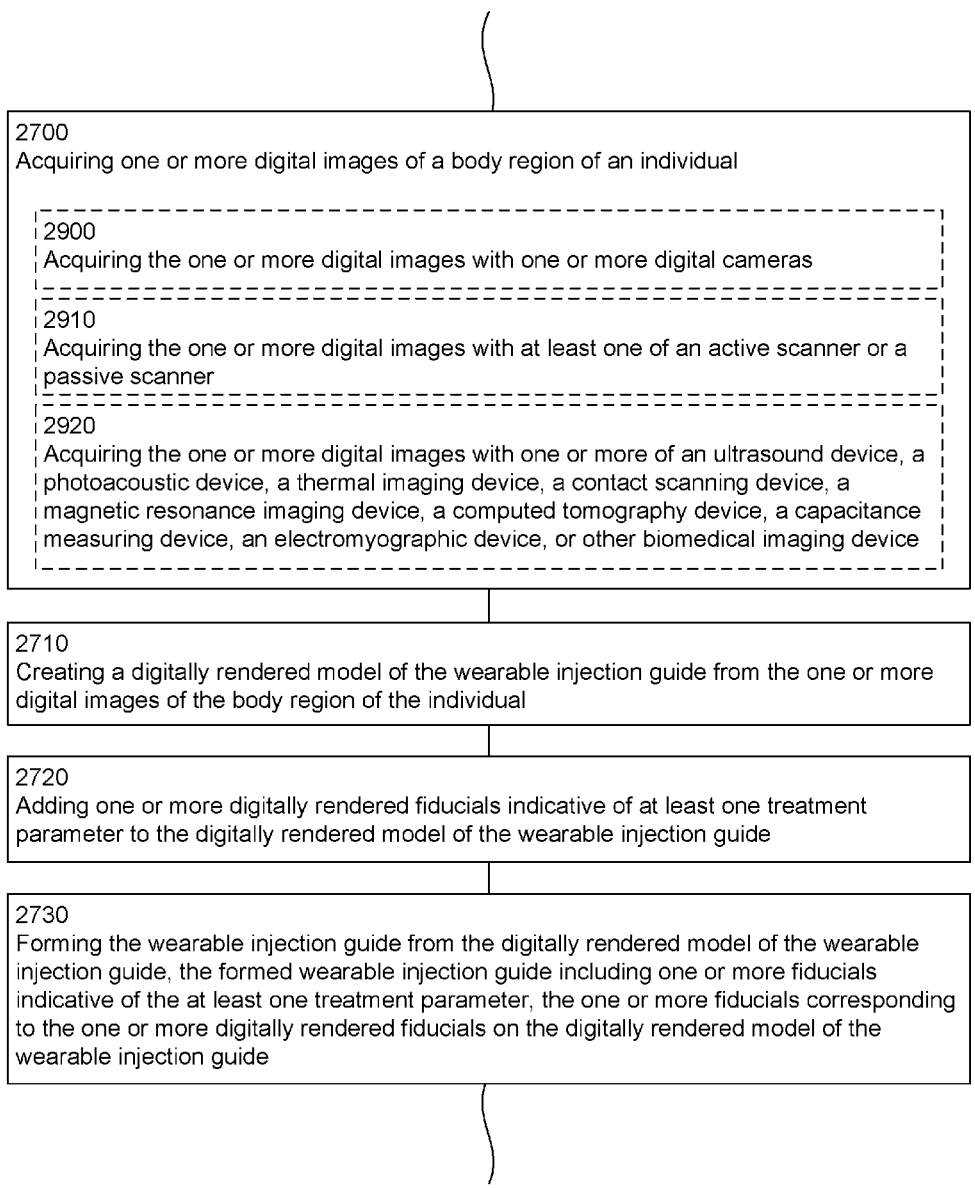
FIG. 29 is a flowchart showing aspects of a method such as depicted in FIG. 27.

FIG. 29 shows further aspects of the method illustrated in FIG. 27 for generating a wearable injection guide. FIG. 29 illustrates that in some embodiments, block 2700 can optionally include block 2900. Block 2900 depicts optionally acquiring the one or more images with one or more digital cameras. For example, one or more digital cameras can be set up to acquire one or more images of the body region of the individual from various angles and/or directions in a process known as stereophotogrammetry. In some embodiments, the one or more digital images can include one or more camera images with sufficient contrast to differentiate between the color of the skin and other skin features, e.g., freckles, tattoo, moles, or blemishes.

Block 2910 of FIG. 29 depicts options acquiring the one or more digital images with at least one of an active scanner or a passive scanner. The at least one active or passive scanner can acquire one or more scans of the individual. The at least one active or passive scanner can acquire one or more scans of the individual from one or more directions. For example, multiple scans taken from multiple directions will allow for obtaining information from all sides of the individual.

In some embodiments, the one or more digital images are acquired with at least one active scanner. An active scanner emits some form of radiation or light which when beamed on an individual creates a measureable reflection. The emitted radiation or light can include electromagnetic radiation, ultrasound or x-ray. Non-limiting examples of active non-contact scanners include hand-held laser scanners as well as a number of three-dimensional scanners (3D scanners) including time-of-flight scanners, triangulation laser scanners, structured-light scanners, and modulated light scanners (see, e.g., Kolbe et al., *Computer Graphics Forum* (2010) 29:141-159, which is incorporated herein by reference). In some embodiments, the one or more active scanners can include one or more triangulation scanners in which a laser emitter, a laser dot on the surface being scanned, and a detection camera are used to triangulate the distance between the laser and the laser dot. For example, the body region of the individual can be scanned at a set distance (e.g., 1-10 mm) as controlled by a tape measure fixed to the camera. The topography of the body region, e.g., the face, differentially reflects the distorted light of the laser, which is then captured by a charge-coupled device (CCD) associated with the camera and converted into distance information using triangulation. In some embodiments, the one or more active scanners can include one or more time-of-flight laser scanners in which a laser rangefinder is used to determine the distance between a surface, e.g., the body region of an individual, and the laser emitter by timing the round-trip time of a pulse of light. The time-of-flight laser scanner scans the entire field of view one point at a time by changing the rangefinders view. In some embodiments, the one or more active scanners can include one or more structured-light 3D scanners in which a pattern of light is projected onto the body region of an individual and the deformation of the projected pattern. Scanners for scanning head, face and/or whole body are commercially available (from, e.g., Cyberware, Monterery Calif.; Accurex Measurement Inc., Swathmore, Pa.; 3dMD Atlanta, Ga.; Konica/Minolta, Ramsey, N.J.)

In some embodiments, the one or more digital images are acquired with at least one passive scanner. A passive scanner relies on detecting reflected ambient radiation, e.g., visible light. Other types of ambient radiation can also be contemplated, including, e.g., infrared light. Non-limiting examples of passive scanners include one or more digitals cameras. In some embodiments, the one or more passive scanners include stereoscopic systems using two video cameras, slightly apart, imaging the same portion of the body region of the individual in a process termed stereophotogrammetry. In some embodiments, the passive scanner can include a single camera taking multiple images under different lighting conditions or from different positions. As an example, the topography of the body region of an individual can be acquired in a point-cloud format using a three-dimensional sensing system consisting of two or more digital cameras and one or more projectors connected to a personal computer. The camera position and shutter can be adjusted to the body region, which is exposed to structured light, allowing for optical representation of the surface by a cloud of up to 300,000 points in three-dimensional coordinates (see, e.g., Feng et al., *Br. J. Oral Maxillofac. Surg.* (2010) 48:105-109, which is incorporated herein by reference).

In some embodiments, the combination of stereophotogrammetry and 3D laser scanner techniques can be combined to generate a three-dimensional model of the body region of an individual (see, e.g., Majid, et al. *International Archives of the Photogrammetry, Remote Sensing and Spatial Information Science.* Vol. XXXVII. Part B5. (2008) 805-811; Markiewicz & Bell, *Facial Plast. Surg. Clin. N. Am.* (2011) 19:655-682; van Heerbeek et al., *Rhinology* (2009) 47:121-125, which are incorporated herein by reference).

Returning to FIG. 29, block 2700 further optionally includes block 2920. Block 2920 depicts optionally acquiring one or more digital images with one or more of an ultrasound device, a photoacoustic device, a thermal imaging device, a contact scanning device, a magnetic resonance image device, a computed tomography device, a capacitance measuring device, electromyographic device, or other biomedical imaging device. For example, skin topographic structures, e.g., wrinkles, can be imaged using a capacitive device with sensor plates pressed lightly on the skin surface (see, e.g., Bevilacqua et al., (2006) *IEEE International Conference on Video and Signal Based Surveillance*, pp. 53, which is incorporated herein by reference). For example, electromyography can be used to determine muscle anatomical features and in particular facial muscle anatomical features (see, e.g., Lapatki et al., *J. Neurophysiol.* (2006) 95:342-354, which is incorporated herein by reference).

Figure 30:
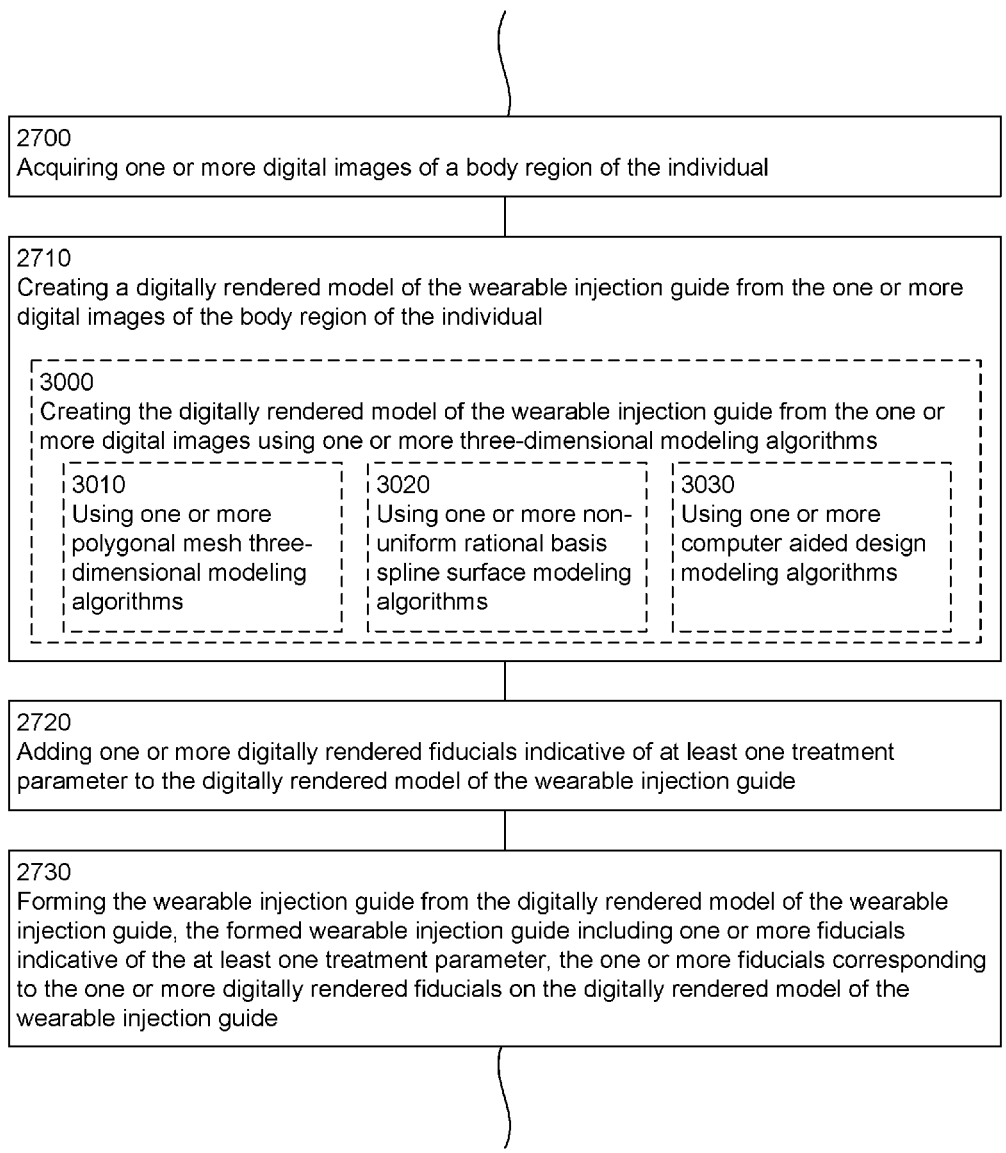
FIG. 30 is a flowchart depicting aspects of a method such as illustrated in FIG. 27.

FIG. 30 shows further aspects of the method of FIG. 27. Block 2710 optionally include block 3000. Block 3000 depicts optionally creating a digitally rendered model of the wearable injection guide from the one or more digital images using one or more three-dimensional modeling algorithms. Block 3000 can optionally include blocks 3010, 3020, and 3030. Block 3010 shows optionally using one or more polygonal mesh three-dimensional modeling algorithms to create the digitally rendered model of the wearable injection guide. Block 3020 shows optionally using one or more non-uniform rational basis spline surface modeling algorithms to create the digitally rendered model of the wearable injection guide. Block 3030 shows optionally using one or more computer aided design modeling algorithms to create the digitally rendered model of the wearable injection guide.

Creating a digitally rendered three-dimensional model of the wearable injection guide from the acquired one or more digital images includes using a computing device and appropriate software or instructions to create the digitally rendered wearable injection guide. In some embodiments, the acquired one or more digital images are brought into a computing device that is capable of aligning or registering the images into a common coordinate system and then integrating the images into a single three-dimensional model.

Figure 31:
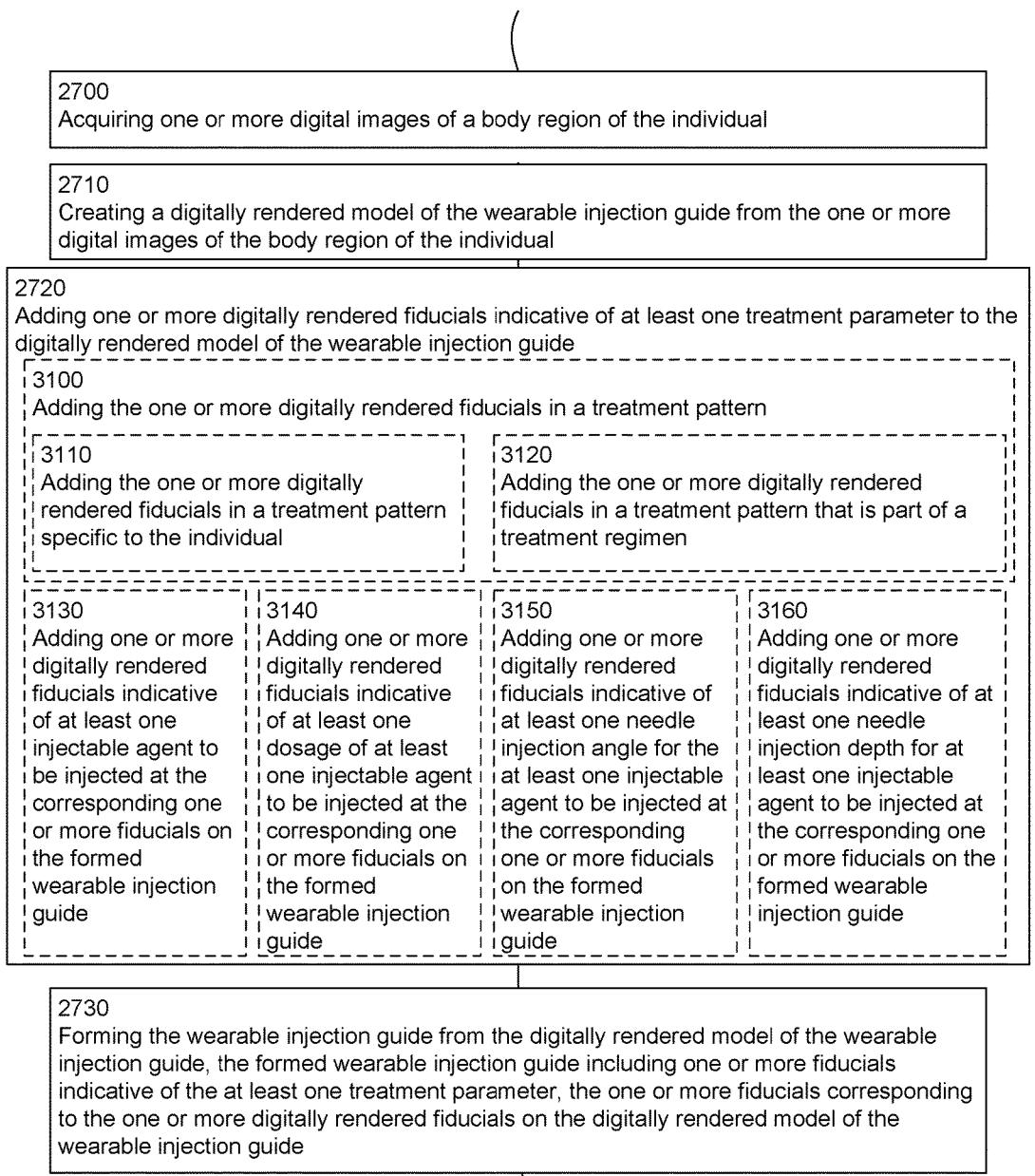
FIG. 31 is a flowchart illustrating aspects of a method such as shown in FIG. 27.

In some embodiments, the active or passive scanners may produce point clouds of data that are reconstructed using one or more three-dimensional modeling algorithms to form a digitally rendered model of the wearable injection guide. One or more modeling programs can be used for this purpose. Non-limiting examples of types of modeling programs include polygonal mesh three-dimensional modeling programs, non-uniform rational basis spline (NURBS) surface modeling programs, or editable feature-based computer aided design (CAD) modeling programs. In some embodiments, the data may be modeled using a first modeling approach, for example, a NURBS based modeling program and further refined using a second modeling approach, for example, a CAD-based modeling program. Numerous software programs are available for generating three-dimensional models from scanned images. For example, non-limiting examples of CAD/CAM software programs applicable to medical imaging include Amira (Visage Imaging GmbH, Berlin Germany); Analyze (AnalyzeDirect, Inc, Overland Park, Kans.); iNtellect Cranial Navigation System (Stryker, Freiburg, Germany); iPlan (BrainLab, Westchester, Ill.); Maxilim (Medicim, Bruges Belgium), Mimics, SurgiCase CMF, and SimPlant OMS (Materialise, Leuven, Belgium); Voxim (IVS Solutions, Chemnitz, Germany), 3dMD (Atlanta, Ga.); Alma3D (Alma IT Systems, Barcelona, Spain); and ImageJ (National Institutes of Health, Boston, Mass.) (see, e.g., Markiewicz & Bell, *Facial Plast. Surg. Clin. N. Am.* (2011) 19:655-682, which is incorporated herein by reference). Facial feature extraction can be acquired using one or more of an active shape model algorithm (see, e.g., Sun & Xie, 11$^{th}$ *IEEE International Conference on Communication Technology Proceedings*, (2008) pp. 661-664; Zheng & Yang *IEEE Proceedings of the Seventh International conference on Machine Learning and Cybernetics*, (2008) pp. 2841-2845, which are incorporated herein by reference). Other software packages capable of generating a digitally rendered model of the wearable injection guide from one or more digital images of a body region of an individual can be used for this purpose. Additional approaches for generating three-dimensional models are described in Bernardini & Rushmeier *Computer Graphics Forum* (2002) 21:149-172;

FIG. 31 depicts further aspects of the method of FIG. 27. FIG. 31 illustrates that in some embodiments, block 2720 can optionally include block 3100. Block 3100 depicts optionally adding the one or more digitally rendered fiducials in a treatment pattern. In some embodiments, the one or more digitally rendered fiducials are added to the digitally rendered model of the wearable injection guide at one or more locations independent of the location of an injection site. For example, one or more digitally rendered fiducials can be added anywhere on the model to provide general treatment parameters for use with the wearable injection guide. In some embodiments, the one or more digitally rendered fiducials are added to the digitally rendered model of the wearable injection guide in a treatment pattern such that the one or more fiducials are indicative of an injection site (e.g., crosshairs) and/or at least one treatment parameter indicated at that injection site (e.g., dosage of an injectable agent). Block 3100 optionally includes blocks 3110 and 3120. Block 3110 depicts optionally adding the one or more digitally rendered fiducials in a treatment pattern specific to the individual. Block 3120 depicts adding the one or more digitally rendered fiducials in a treatment pattern that is part of a treatment regimen.

Block 2720 of FIG. 31 can optionally include blocks 3130, 3140, 3150, and 3160. Block 3130 depicts optionally adding one or more digitally rendered fiducials indicative of at least one injectable agent to be injected at the corresponding one or more fiducials on the wearable injection guide. For example, one or more digitally rendered fiducials indicative of at least one of an injectable agent, e.g., neurotoxin, subcutaneous volume enhancer, dermal filler, insulin, hormone, chemotherapeutic, antimicrobial, or other biological agent, can be added to the digitally rendered model of the wearable injection guide. Adding one or more digitally rendered fiducials indicative of other injectable agents not explicitly described herein is also contemplated. Block 3140 depicts optionally adding one or more digitally rendered fiducials indicative of at least one dosage of at least one injectable agent to be injected at the corresponding one or more fiducials on the wearable injection guide. For example, one or more digitally rendered fiducials can be added to the digitally rendered model of the wearable injection guide indicating the units of botulinum toxin or milliliters of collagen filler, for example, to be injected at any given injection site. Block 3150 shows optionally adding one or more digitally rendered fiducials indicative of at least one needle injection angle for the at least one injectable agent to be injected at the corresponding one or more fiducials on the wearable injection guide. For example, one or more digitally rendered fiducials can be added to the digitally rendered model of the wearable injection guide indicating that the injection needle should be injected at 90 degrees or less relative to the skin surface of the body region. Block 3160 shows optionally adding one or more digitally rendered fiducials indicative of at least one needle injection depth for at least one injectable agent to be injected at the corresponding one or more fiducials on the wearable injection guide. For example, one or more digitally rendered fiducials can be added to the digitally rendered model of the wearable injection guide indicating whether the injection needle should be injected into the epidermal, dermal, subcutaneous, or intramuscular portions of the skin. In another example, one or more digitally rendered fiducials can be added to the digitally rendered model of the wearable injection guide indicating that the injection needle should be injected 2-3 mm or 4-10 mm or deeper into the underlying tissue of the body region. Needle injection depth is dependent upon the type of injectable agent being injected and the skin thickness at any given part of the body, as described previously herein. In some embodiments, the one or more digitally rendered fiducials can be added to at least a portion of the digitally rendered model of the wearable injection guide that is near or coincident with a treatment area on the corresponding body region of the individual.

Figure 32:
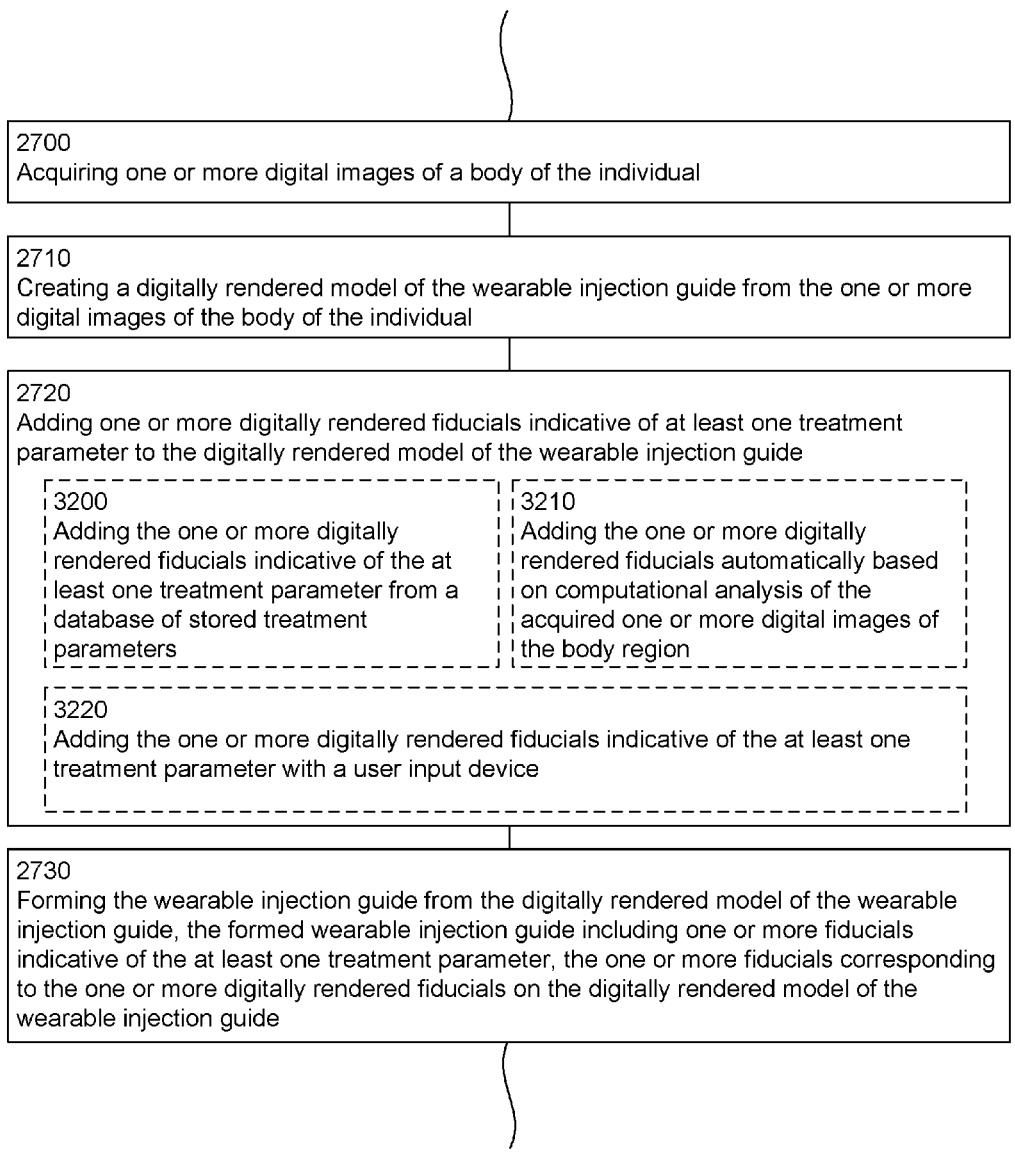
FIG. 32 is a flowchart showing aspects of a method such as depicted in FIG. 27.

FIG. 32 illustrates further aspects of the method of FIG. 27. FIG. 32 illustrates that in some embodiments, block 2720 can optionally include blocks 3200, 3210, and 3220. Block 3200 shows optionally adding the one or more digitally rendered fiducials indicative of the at least one treatment parameter to the digitally rendered model of the wearable injection guide from a database of stored treatment parameters. The database of stored treatment parameters can include treatment options, e.g., injectable agents, for a given condition as well as dosing information and information regarding needle penetration and needle size specific for any given injectable agent. In some embodiments, the database of stored treatment parameters can include treatment options specific to the individual, e.g., previously used injectable agents, dosages, and injection depth. In some embodiments, the database of stored treatment parameter can include a medical history of an individual, e.g., allergies, age, skin properties, medical condition, and other medical history relevant to the injection treatment regimen. The medical history can be used by the physician or other practitioner to plan an individual's treatment regimen such that the appropriate digitally rendered fiducials outlining that plan are added to the digitally rendered model of the wearable injection guide.

Block 3210 depicts adding the one or more digitally rendered fiducials automatically based on computational analysis of the acquired one or more digital images of the body region. The computational analysis can include a comparison of the one or more digital images of the body region with stored data that includes images of standard, normal or ideal body regions or previously captured images of the body region of the individual. In some embodiments, the stored data includes idealized aesthetics of a female or male face (see, e.g., Carruthers et al., *Plast. Reconstr. Surg.* (2008) 121 (Suppl):5S-30S, which is incorporated herein by reference). In some embodiments, the stored data include normalized skin characteristics based on age or other demographics (see, e.g., Wolff et al., *Fertil. Steril.* (2011) 95:658-662, which is incorporated herein by reference). In some embodiments, the one or more digitally rendered fiducials can be added automatically to the digitally rendered model of the wearable injection guide by a computing device based on data from the database of stored treatment parameters. In some embodiments, the computational analysis can include algorithms for predicting the outcome of a particular treatment regimen. For example, the computational analysis may be used to show an individual via a display, e.g., a computer monitor, how a given facial feature, e.g., nasolabial folds, will change in response to injection of an injectable agent, e.g., a dermal filler.

Returning to FIG. 32, Block 3220 shows optionally adding the one or more digitally rendered fiducials indicative of the at least one treatment parameter to digitally rendered model of the wearable injection guide with a user input device. The user input device can include a keyboard or interactive display panel. In some embodiments, the user input device is a keyboard in communication with the computing device running the one or more three-dimensional modeling algorithms to create the digitally rendered model of the wearable injection guide. In some embodiments, the user input device is a wireless device, e.g., a cell phone or other handheld device, capable of wirelessly adding one or more digitally rendered fiducials to the digitally rendered model of the wearable injection guide. In some embodiments, the one or more digitally rendered fiducials indicative of at least one treatment parameter can be added by a physician or other practitioner using an input device based on consulting data from a database of stored treatment parameters. In some embodiments, the one or more digitally rendered fiducials can be added based on preferences of the individual.

Figure 33:
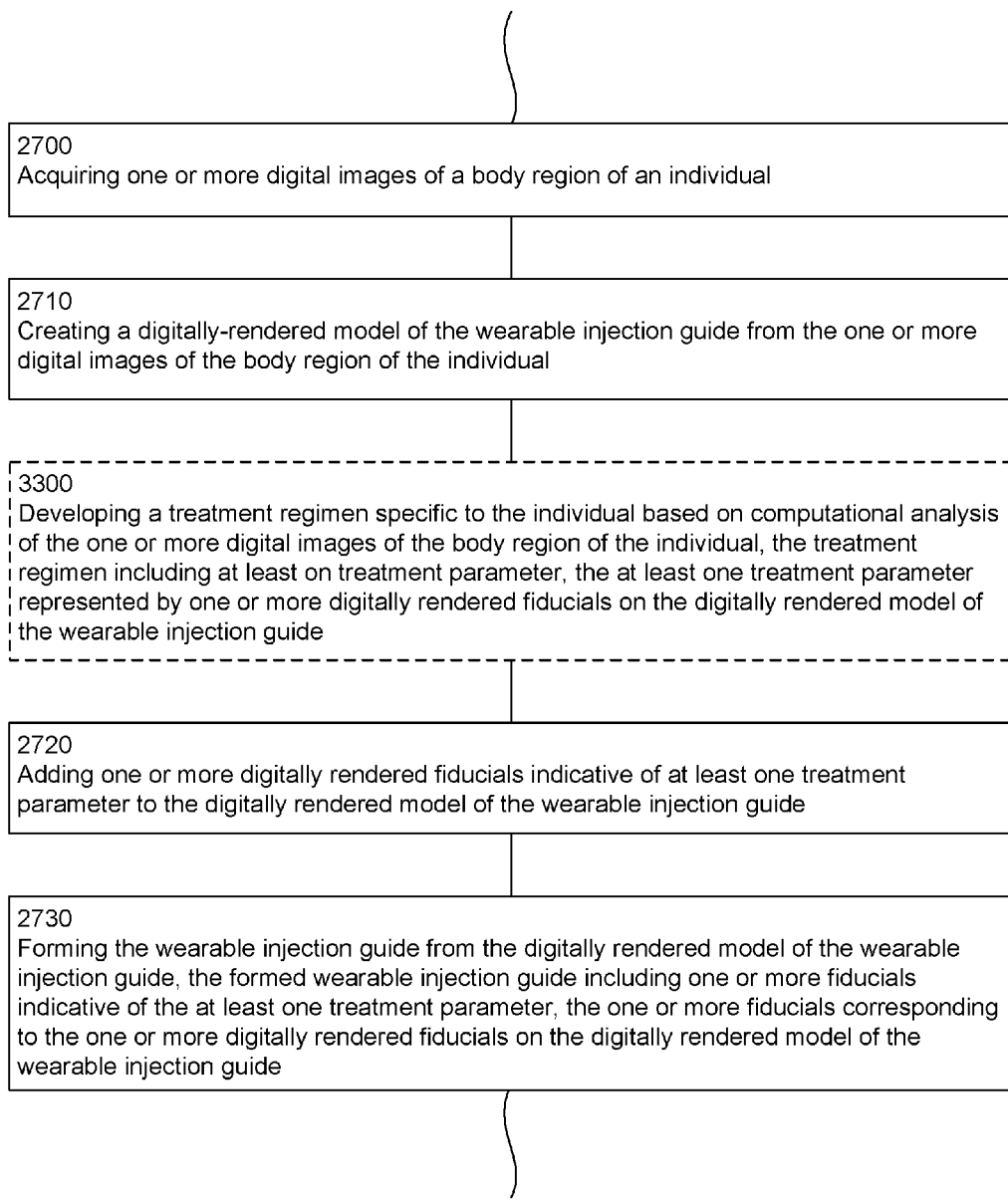
FIG. 33 is a flowchart depicting aspects of a method such as illustrated in FIG. 27.

FIG. 33 shows further aspects of the method of FIG. 27. FIG. 33 shows optionally including block 3300. Block 3300 depicts optionally developing a treatment regimen specific to the individual based on computational analysis of the one or more digital images of the body region of the individual, the treatment regimen including at least one treatment parameter, the at least one treatment parameter represented by one or more digitally rendered fiducials on the digitally rendered model of the wearable injection guide.

Figure 34:
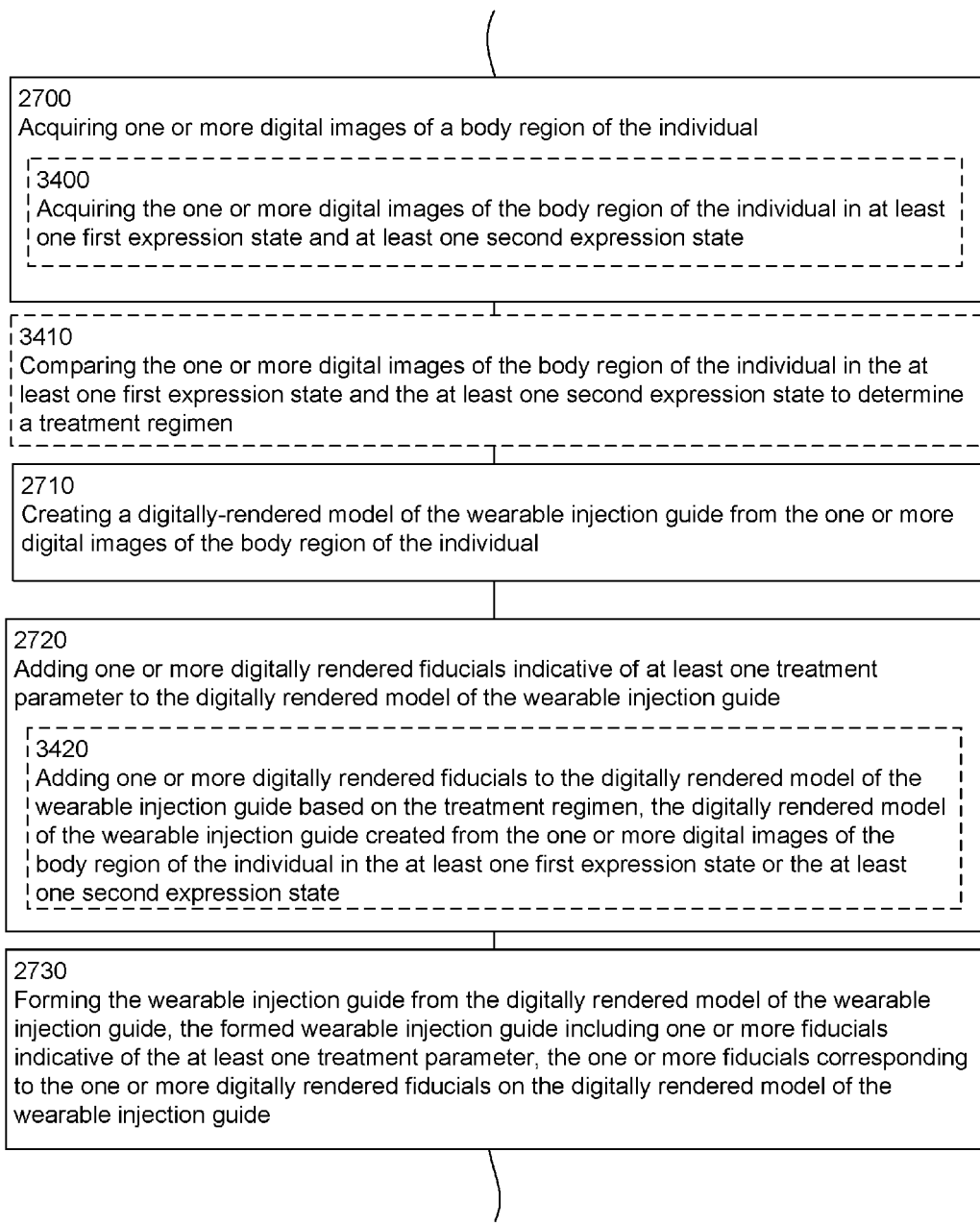
FIG. 34 is a flowchart illustrating aspects of a method such as shown in FIG. 27.

FIG. 34 shows further aspects of the method of FIG. 27. FIG. 34 shows optionally including blocks 3400, 3410, and 3420. Block 3400 depicts optionally acquiring the one or more digital images of the body region of the individual in at least one first expression state and at least one second expression state. Block 3410 depicts optionally comparing the one or more digital images of the body region of the individual in the at least one first expression state and the at least one second expression state to determine a treatment regimen. Block 3420 depicts optionally adding one or more digitally rendered fiducials to the digitally rendered model of the wearable injection guide based on the treatment regimen, the digitally rendered model of the wearable injection guide created from the one or more digital images of the body region of the individual in the at least one first expression state or the at least one second expression state.

Block 3400 of FIG. 34 depicts acquiring one or more digital images of the body region of an individual in at least one first expression state and at least one second expression state. For example, one or more images of the topography of a body region of an individual's face can be acquired while the individual is in a first expression state, e.g., in a relaxed state, and used to reveal lines or wrinkles present on the individual's face in the first expression state. One or more images of the topography of the individual's face are acquired in a second expression state, e.g., a tensed or animated state. Non-limiting examples of tensed or animated states include laughing, smiling, frowning, grimacing or other non-relaxed states of the individual's face. The one or more images of the topography of the individual's face in the second expression state, e.g., the animated state, can be used to reveal additional lines or wrinkles present on the individual's face in the second expression state relative to the first expression state, e.g., the relaxed state. For example, the one or more images of the individual's face can be acquired while the individual is frowning and generating associated frown-line/wrinkles (glabellar lines) between the eyebrows. As another example, the one or more images of the body region of the individual's face can be acquired while the individual is smiling and generating laugh lines (nasolabial folds) and/or crow's feet near the eyes.

Returning to block 3410 of FIG. 34, in some embodiments, comparing the one or more digital images of the body region of the individual in the at least one first expression state and the at least one second expression state to determine a treatment regimen includes overlaying the one or more digital images in the first expression state and the one or more digital images in the second expression state to identify one of more areas of the body region in need of treatment. For example, the one or more images of the topography of an individual's face in a first expression state, e.g., a relaxed state, are overlayed with the one or more images of the topology of an individual's face in a second expression state, e.g., an animated state. In this manner, areas in need of treatment, e.g., frown lines between the eye brows or smile lines around the mouth, can be identified and placed onto the digitally rendered model of the wearable injection guide and viewed by the physician or other practitioner. The treatment regimen with at least one treatment parameter can then be formulated based on the treatment need. Accordingly, one or more digitally rendered fiducials indicative of the treatment parameters can be added either automatically by the computing device or by a physician, other practitioner, or the individual to the digitally rendered model of a wearable injection guide. The digitally rendered model of the wearable injection guide can be created from the one or more digital images in the first expression state, the one or more digital images in the second expression state, or from some combination of digital images.

Figure 35:
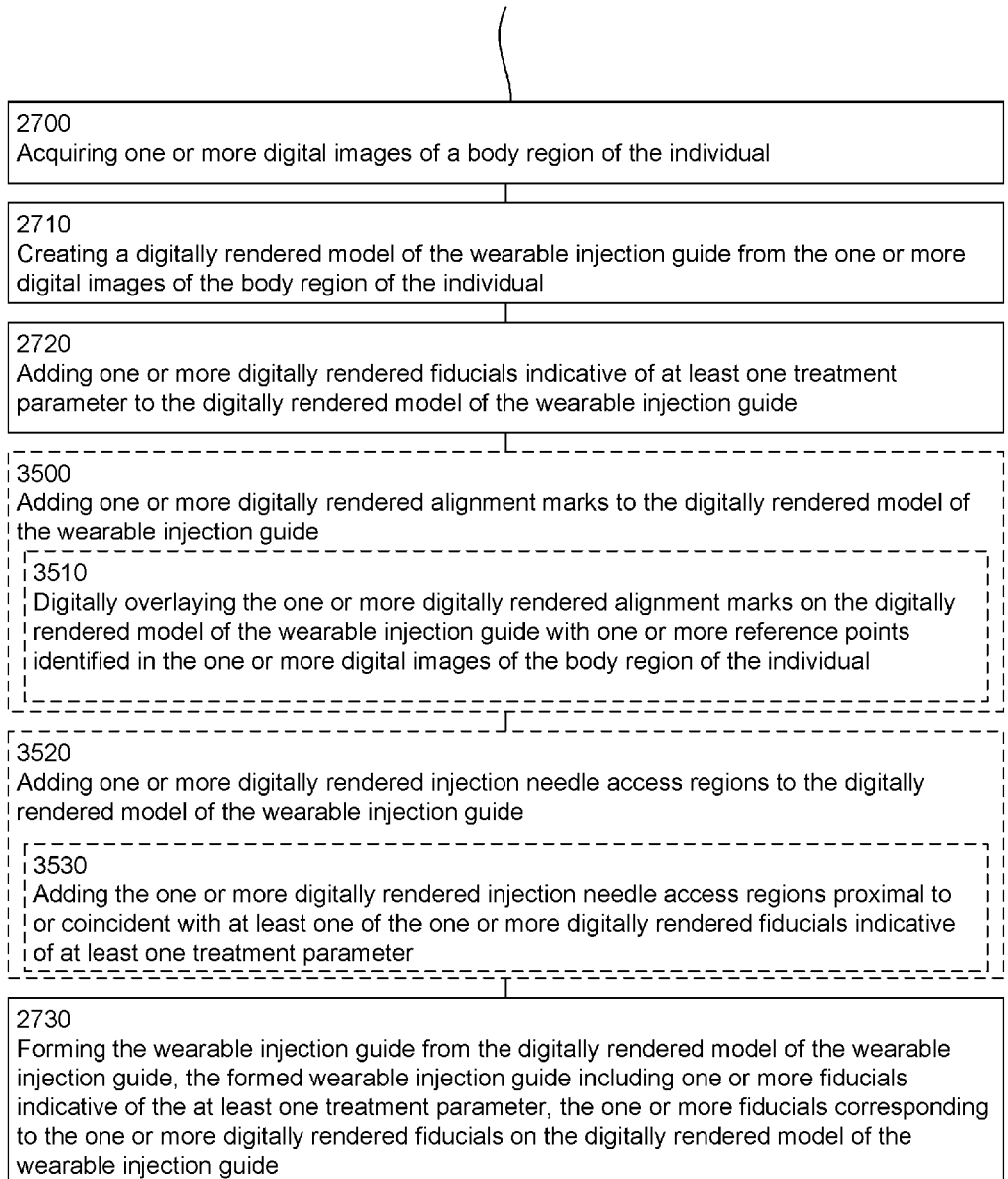
FIG. 35 is a flowchart showing aspects of a method such as depicted in FIG. 27.

FIG. 35 shows further aspects of the method of FIG. 27. Block 3500 depicts optionally adding one or more digitally rendered alignment marks to the digitally rendered model of the wearable injection guide corresponding to one or more reference points on the body region of the individual. Block 3500 optionally includes block 3510. Block 3510 depicts optionally digitally overlaying the one or more digitally rendered alignment marks on the digitally rendered model of the wearable injection guide with one or more reference points identified in the one or more digital images of the body region of the individual. For example, the one or more digital images of the body region may include one or more images of topographical landmarks, non-limiting examples of which include skin pigmentation, pigmented areas such as moles or freckles, scars, blemishes, tattoos, subsurface blood vessels, anatomical features or any other topographical landmarks associated with the body region of the individual that can be used as reference points for aligning the wearable injection guide onto the body region. One or more digitally rendered alignment marks are added to the digitally rendered model of the wearable injection at or near the images of the one or more reference points.

Block 3520 of FIG. 35 depicts optionally adding one or more digitally rendered injection needle access regions to the digitally rendered model of the wearable injection guide. In some embodiments, adding the one or more digitally rendered injection needle access regions to the digitally rendered model of the wearable injection guide can include adding a digitally rendered opening in the model which when manufactured will result in a hole in the wearable injection guide of appropriate diameter for insertion of an injection needle. In some embodiments, adding one or more digitally rendered injection needle access regions to the digitally rendered model of the wearable injection guide can include decreasing the thickness of specific portions of the model which when manufactured will result in specific portions of the wearable injection guide that are more easily penetrated by an injection needle. In some embodiments, adding the one or more digitally rendered injection needle access regions to the digitally rendered model of the wearable injection guide can include indicating use of a material with reduced hardness in specific portions of the model which when manufactured will result in specific portions of the wearable injection guide that are more easily penetrated by an injection needle. Block 3520 optionally includes block 3530. Block 3530 shows optionally adding the one or more digitally rendered injection needle access regions proximal to or coincident with at least one of the one or more digitally rendered fiducials indicative of the at least one treatment parameter.

Figure 36:
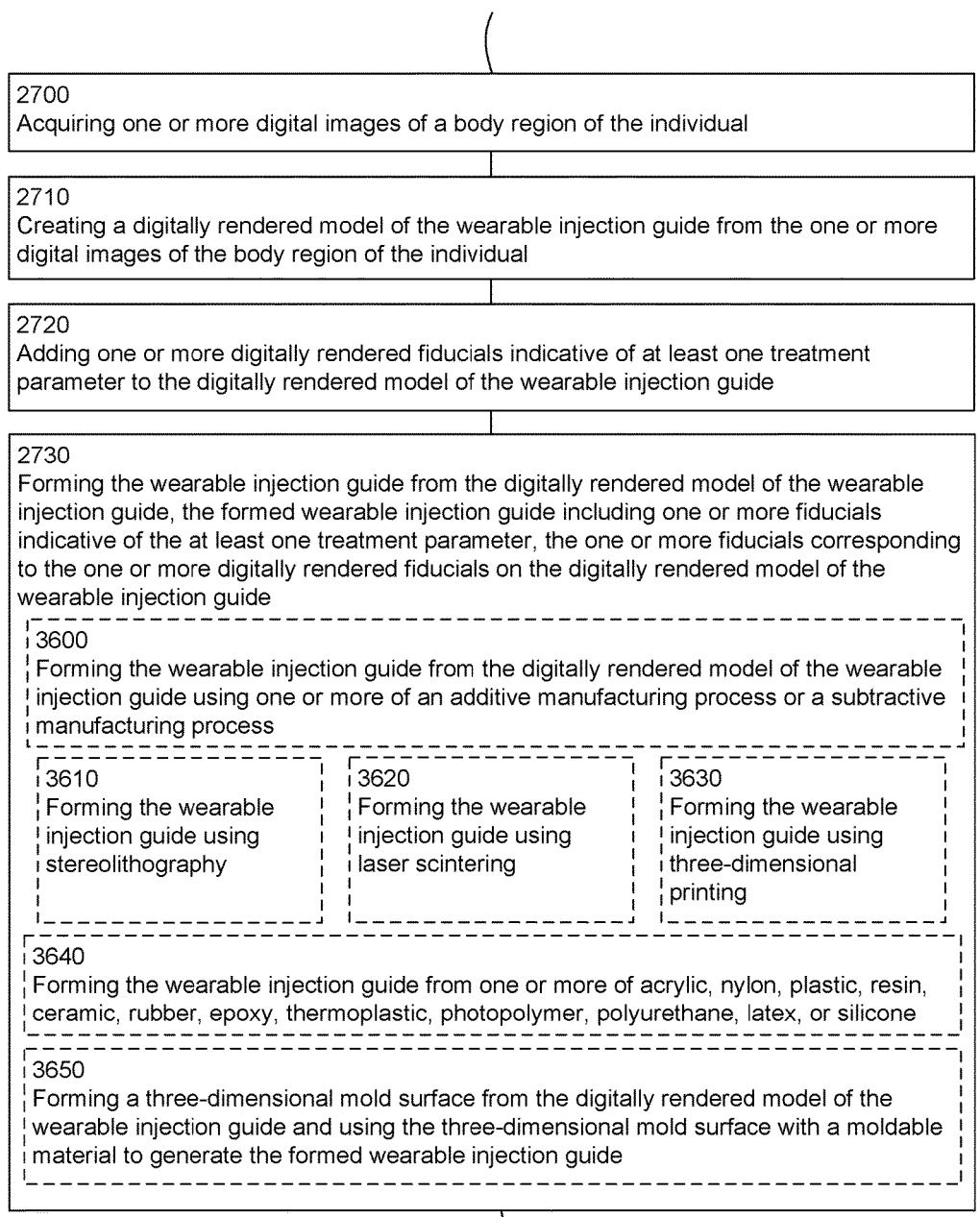
FIG. 36 is a flowchart depicting aspects of a method such as illustrated in FIG. 27.

FIG. 36 illustrates further aspects of the method of FIG. 27. FIG. 36 depicts block 2730 forming the wearable injection guide from the digitally rendered model of the wearable injection guide optionally including blocks 3600, 3610, 3620, 3630, and 3640. Block 3600 shows optionally forming the wearable injection guide from the digitally rendered model of the wearable injection guide using one or more of an additive manufacturing process or a subtractive manufacturing process. Block 3610 shows optionally forming the wearable injection guide using stereolithography. Block 3620 shows optionally forming the wearable injection guide using laser scintering. Block 3630 shows optionally forming the wearable injection guide using three-dimensional printing. Additional non-limiting examples of methods for generating a three-dimensional structure from digitized information include fused deposition modeling, polyjet, vacuum casting, reaction injection molding, or injection molding. Block 3640 shows optionally forming the wearable injection guide from one or more of acrylic, nylon, plastic, ceramic, resin, rubber, epoxy, thermoplastic, photopolymer, polyurethane, latex or silicone. The type of material used for forming the wearable injection guide is dependent upon the method used to form the wearable injection guide and the desired properties, e.g., rigidity, transparency, and/or porosity, of the final product. Exemplary materials and methods for forming a wearable injection guide using stereolithography, laser scintering or three-dimensional printing as well as other methods for forming a wearable injection guide from digitally rendered model of the wearable injection guide are described herein.

In some embodiments, the wearable injection guide is formed using an additive manufacturing process. Additive manufacturing refers to a class of manufacturing process in which a three-dimensional object is built by adding layers of material upon one another. Other terms include layered manufacturing, direct digital manufacturing, or solid freeform fabrication. Non-limiting examples of additive manufacturing processes include liquid-based processes, e.g., stereolithography, jetted photopolymer, and ink jet printing; powder-based processes, e.g., selective laser sintering, direct metal laser sintering, and three-dimensional printing; and solid-based processes, e.g., laminated object manufacturing, fused deposition modeling. In some embodiments, the wearable injection guide is formed using a subtractive manufacturing process. Subtractive manufacturing refers to a class of manufacturing process in which a three-dimensional object is built by cutting away material. Non-limiting examples of subtractive manufacturing processes include machining, milling, turning, and drilling. Other non-limiting examples of manufacturing processes include molding, e.g., blow molding, injection molding, or thermoforming; and casting, e.g., centrifugal casting, die casting, sand casting, shell mold casting.

In some embodiments, the wearable injection guide is generated using stereolithography using one or more optically-curable photopolymers. Non-limiting examples of materials useful for stereolithography include poly(ethylene glycol)1500, Accura 60, Accura 25, Accura Xtreme, Somos 9420, Somos 11122, Somos 18420, Somos DMX, Rigi2200, TuskXC2700T/Tusk2700 W, Nano5000, Flex45, Flex65, Flex70B, Flex 80, Protogen White. Other non-limiting examples of stereolithography include three-dimensional printing (3D printing), optical fabrication, photo-solidification, solid free-form fabrication, and solid imaging.

In some embodiments, the wearable injection guide can be generated by 3D printing using an inkjet technology, e.g., PolyJet™ (from Objet Ltd) in which photopolymer materials are jetted in ultra-thin layers onto a build tray and cured layer by layer with UV light. Non-limiting examples of materials for use in generating a wearable injection guide using inkjet technology include Fullcure 720, VeroWhite, VeroBlack, VeroBlue, and VeroGray for rigid structures; Durus for semi-flexible structures; and Tango Elastomers for rubber-like structures. Other examples of 3D printers include ProJet and ZPrinters available from 3D Systems Corporation, Rock Hill S.C. and Freeform Pico, Asiga, Anaheim Hills, Calif.

In some embodiments, the wearable injection guide is generated using selective laser sintering in which a high power laser, e.g., a carbon dioxide laser, is used to fuse small particles of plastic, metal, ceramic, glass powders, or combinations thereof into a mass that has a desired three-dimensional shape. Non-limiting examples of material for use in generating a wearable injection guide using laser sintering include polyamide, nylon, carbon, hydroxyapatite, glass filled polyamide, and alumide.

In some embodiments, the wearable injection guide is generated using fused deposition modeling. Fused deposition modeling is an extrusion based three-dimensional modeling process using thermoplastic materials. Non-limiting examples of materials for use in fused deposition modeling include the thermoplastics ABS, ABS/F1, polycarbonate, and Ultem 9085. The uPrint SE from Stratasys (Eden Prairie, Minn.) or the Dimension Elite 3D printer from Dimension, Inc. (Eden Prairie, Minn.) are non-limiting examples of systems for fused deposition modeling with thermoplastics that might be appropriate for use in a medical clinic.

Returning to FIG. 36, the method of FIG. 27 can optionally include block 3650. Block 3650 depicts optionally forming the wearable injection guide by forming a three-dimensional mold surface from the digitally rendered model of the wearable injection guide and using the three-dimensional mold surface with a moldable material to generate the formed wearable injection guide. For example, a three-dimensional mold surface of the individual's face can be fabricated from a thermoplastic material based on the digitally rendered model of the wearable injection guide. A moldable material, e.g., latex, can then be poured into or over the three-dimensional mold surface to generate the formed wearable injection guide. The three-dimensional mold surface can be used repeatedly to generate one or more wearable injection guides.

Figure 37:
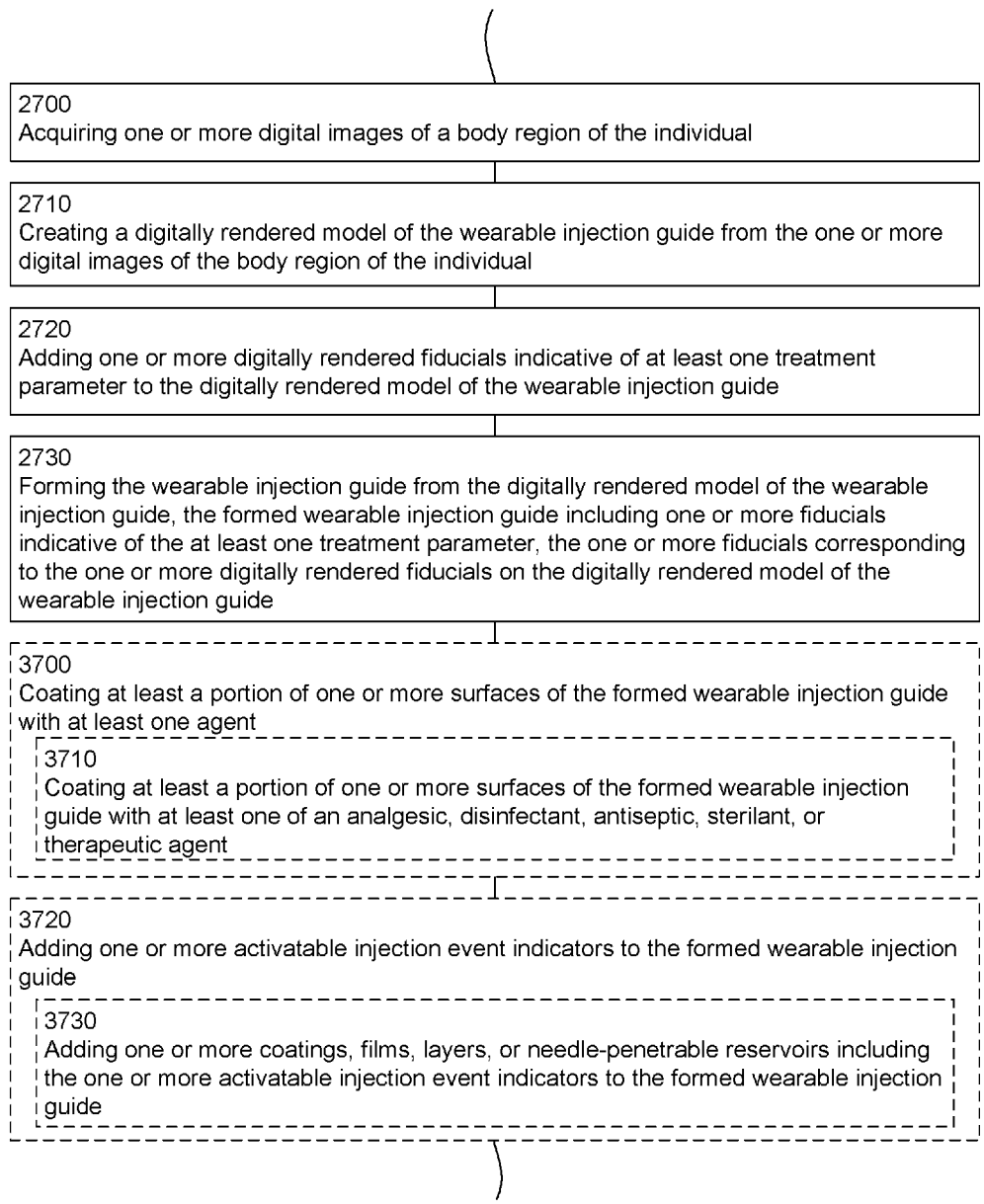
FIG. 37 is a flowchart illustrating aspects of a method such as shown in FIG. 27.

FIG. 37 depicts further aspects of the method of FIG. 27. FIG. 37 shows optionally including blocks 3700 and 3710 to the method of generating a wearable injection guide. Block 3700 illustrates optionally coating at least a portion of one or more surfaces of the formed wearable injection guide with at least one agent. For example, the inner surface of a wearable injection guide formed from a porous material, e.g., a ceramic or hydroxyapatite, can be coated with one or more agents following manufacture and prior to deployment onto the body region of an individual. Block 3700 optionally includes block 3710. Block 3710 shows coating at least a portion of one or more surfaces of the formed wearable injection guide with at least one of an analgesic, disinfectant, antiseptic, sterilant, or therapeutic agent, examples of which have been described elsewhere herein. For example, a surface of one or more of the injection needle access regions of the formed wearable injection guide can be coated with lidocaine for use in easing the pain associated with needle injection.

Block 3720 of FIG. 37 illustrates optionally adding one or more activatable injection event indicators to the formed wearable injection guide. The one or more activatable injection event indicators can include one or more of a pressure sensitive material, flowable dye, and/or needle penetrable membrane. Block 3720 optionally includes block 3730. Block 3730 shows optionally adding one or more coatings, films, layers, or needle-penetrable reservoirs including the one or more activatable injection event indicators. For example, a pressure sensitive film can be added to the outer surface of the wearable injection guide following manufacture, the pressure sensitive film configured to change color in response to applied pressure accompanying insertion of an injection needle through the wearable injection guide. In another example, needle penetrable reservoirs, e.g., bubbles of needle penetrable plastic encapsulating a flowable dye, can be fixed into injection needle access regions, e.g., openings in the rigid material of formed wearable injection guide and release dye in response to insertion of an injection needle through the injection needle access regions. In some embodiments, the one or more needle-penetrable reservoirs can further include one or more agents, e.g., one or more analgesic, one or more disinfectant, antiseptic or sterilant, and/or one or more therapeutic agent, non-limiting examples of which have been described elsewhere herein.

Figure 38:
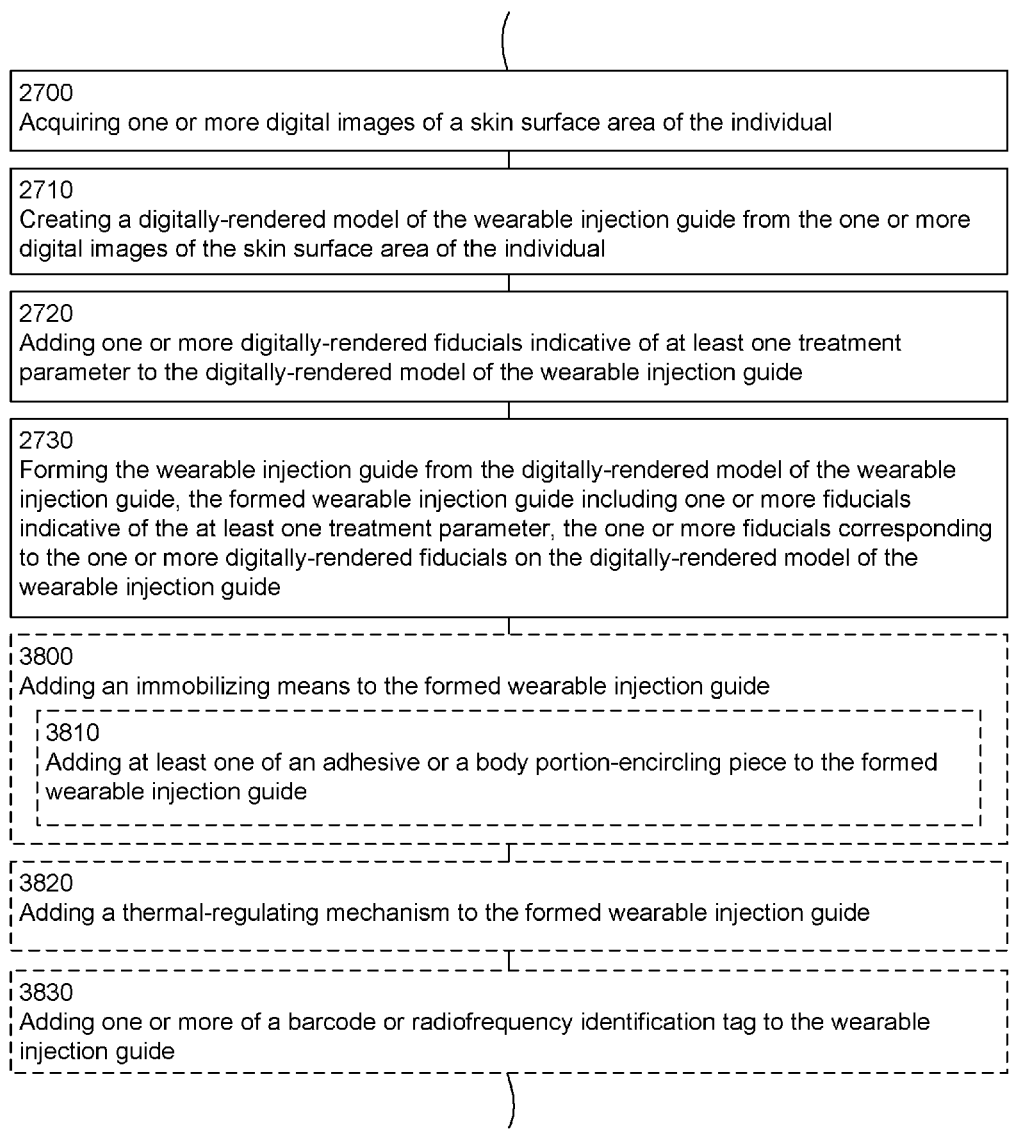
FIG. 38 is a flowchart illustrating aspects of a method such as shown in FIG. 27.

FIG. 38 illustrates further aspects of the method of FIG. 27. FIG. 38 shows optionally including blocks 3800 and 3820 to the method of generating a wearable injection guide. Block 3800 shows optionally adding an immobilizing means to the formed wearable injection guide. In some embodiments, the immobilizing means is used to keep the wearable injection guide covering a specified portion of the body region during the injection process. Block 3810 shows optionally adding one or more of an adhesive or a body portion-encircling piece to the formed wearable injection guide as a means of immobilizing the wearable injection guide. Other means of immobilizing the wearable injection guide are contemplated including but not limited to a sleeve or a clamp. Block 3820 shows optionally adding a thermal-regulating mechanism to the formed wearable injection guide. The thermal regulating mechanism can be used to either cool or heat the wearable injection guide. For example, cooling the wearable injection guide prior to, during, and/or after needle injection into the underlying tissue can be used to attenuate pain and bruising associated with needle injection. For example, heating the wearable injection guide prior to, during and/or after needle injection into the underlying tissue can be used to dilate blood vessels, causing the injectable agent to disperse more rapidly following injection. The thermal-regulating mechanism can include one or more of a Peltier device or thermochemical agent added to the formed wearable injection guide. For example, an inner surface of the wearable injection guide can be impregnated with components of a thermochemical cooling agent, e.g., ammonium nitrate, and activated just prior to deploying the wearable injection guide onto the body region of the individual.

In some embodiments, the method of generating a wearable injection guide further includes adding one or more patient identifiers. Block 3830 shows optionally adding one or more one or more of a barcode or radiofrequency identification tag to the wearable injection guide. In some embodiments, the barcode or radiofrequency identification tag can be added to the digitally rendered model of the wearable injection guide and incorporated into the formed wearable injection guide during manufacture. In some embodiments, the barcode or radiofrequency identification tag can be added to the formed wearable injection guide after manufacture.

In some embodiments, the method of FIG. 27 optionally includes sterilizing the formed wearable injection guide prior to use. The formed wearable injection guide can be sterilized using any of a number of methods including but not limited to heat sterilization, e.g., boiling water, autoclave; radiation sterilization, e.g., gamma rays, electron beam processing, x-ray, ultraviolet light; or chemical sterilization, e.g., ethylene oxide, ozone, bleach, glutaraldehyde, formaldehyde, hydrogen peroxide, and silver compounds.

Figure 39:
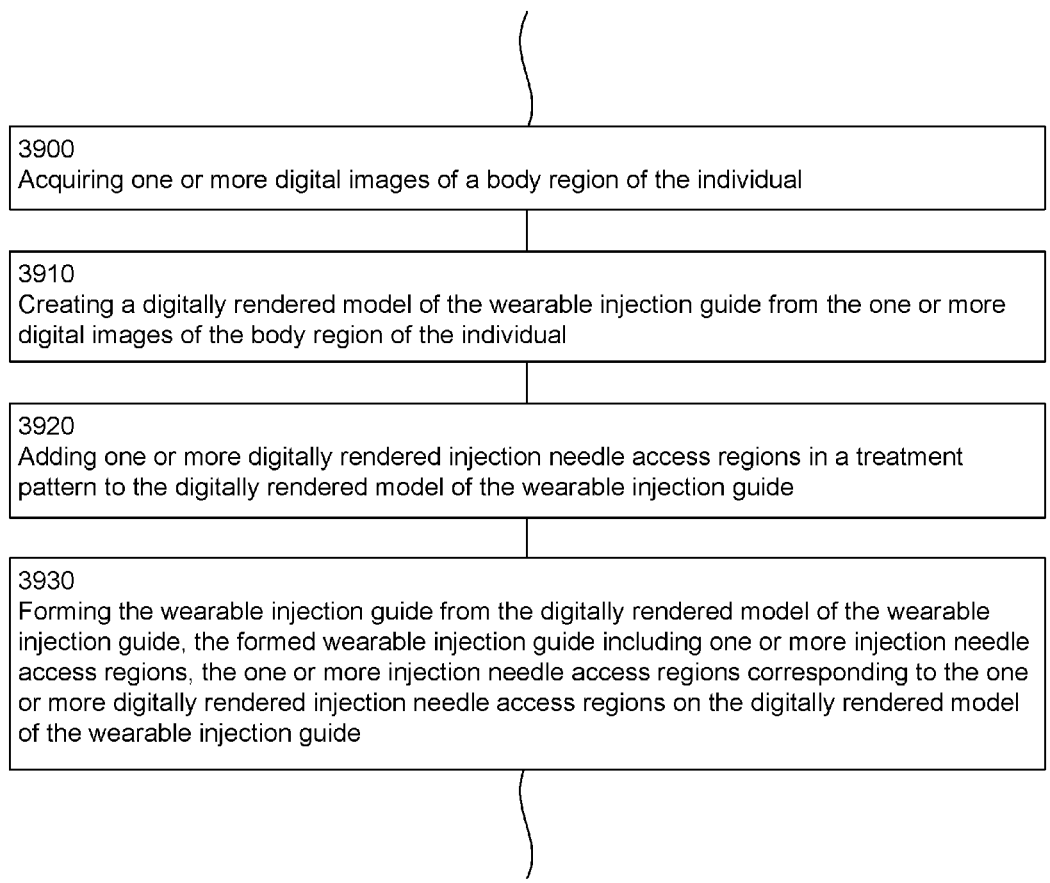
FIG. 39 is a flowchart of a method of generating a wearable injection guide.

FIG. 39 illustrates a method of generating a wearable injection guide for an individual. Block 3900 shows acquiring one or more digital images of a body region of the individual. In some embodiments, acquiring one or more digital images of the body region of an individual includes acquiring one or more digital images of a topography of the body region of the individual. In some embodiments, acquiring the one or more digital images of the body region of the individual includes acquiring the one or more digital images with one or more of a camera, active scanner, or passive scanner. In some embodiments, acquiring the one or more digital images of the body region includes acquiring the one or more digital images with one or more of an ultrasound device, a photoacoustic device, a thermal imaging device, a contact scanning device, a magnetic resonance imaging device, a computed tomography device, a capacitance measuring device, or other biomedical imaging device. Block 3910 depicts creating a digitally rendered model of the wearable injection guide from the one or more digital images of the body region of the individual. Any of a number of three-dimensional modeling algorithms can be used for this purpose, examples of which have been described above herein.

Block 3920 of FIG. 39 depicts adding one or more digitally rendered injection needle access regions in a treatment pattern to the digitally rendered model of the wearable injection guide. The one or more digitally rendered injection needle assess regions can include portions of the digitally rendered model of the wearable injection that represent an opening that transects the digitally rendered model, a reduced thickness in the digitally rendered model, or a reduced hardness in the digitally rendered model. In some embodiments, adding the one or more digitally rendered injection needle access regions includes adding one or more digitally rendered injection needle access regions that transect an inner surface and an outer surface of the digitally rendered model of the wearable injection guide at an angle of 90 degrees or at an angle less than 90 degrees. In some embodiments, adding one or more digitally rendered injection needle access regions includes adding a downward tapered access surface to at least one of the one or more digitally rendered injection needle access regions. The downward tapered access surface on the formed wearable injection guide can be used to direct an injection needle to a very specific portion of the injection needle access region. In some embodiments, adding the one or more digitally rendered injection needle access regions includes automatically adding one or more digitally rendered injection needle access regions in a treatment pattern based on computational analysis of the one or more digital images of the body region of the individual. The computation analysis includes determining where treatment is needed on the body region and the appropriate pattern of injection needle access regions needle to administer that treatment. The one or more digitally rendered injection needle access regions are added to the digitally rendered model of the wearable injection guide in a treatment pattern. In some embodiments, the treatment pattern is generic for a particular condition or treatment option. In some embodiments, the treatment pattern can be specific to an individual, patterned to accommodate specific needs and/or anatomical features of the individual. In some embodiments, the treatment pattern is part of a treatment regimen, the treatment regimen is either a generic treatment regimen or a treatment regimen specific for an individual.

In some embodiments, the method of FIG. 39 further includes adding one or more digitally rendered fiducials indicative of at least one treatment parameter to the digitally rendered model of the wearable injection guide. The one or more digitally rendered fiducials can be added proximal to or coincident with the one or more digitally rendered injection needle access regions.

Returning to FIG. 39, block 3930 illustrates forming the wearable injection guide from the digitally rendered model of the wearable injection guide, the formed wearable injection guide including one or more injection needle access regions in a treatment pattern, the one or more injection needle access regions corresponding to the one or more digitally rendered injection needle access regions on the digitally rendered model of the wearable injection guide. Any of a number of additive or subtractive manufacturing processes can be used to form the wearable injection guide, non-limiting examples of which have been decribed herein.

In some embodiments, the method of FIG. 39 further includes adding one or more fiducials indicative of at least one treatment parameter to the formed wearable injection guide. The one or more fiducials can be added proximal to or coincident with the one or more injection needle access regions on the formed wearable injection guide. In this way, one or more fiducials indicative of at least one treatment parameter can be added to the wearable injection guide after it has been manufactured, allowing for changes in the treatment parameters. In some embodiments, the wearable injection guide is reusable with either fixed permanent fiducials or replaceable fiducials, allowing for repeated use of the wearable injection guide and flexibility in the treatment parameters.

Figure 40:
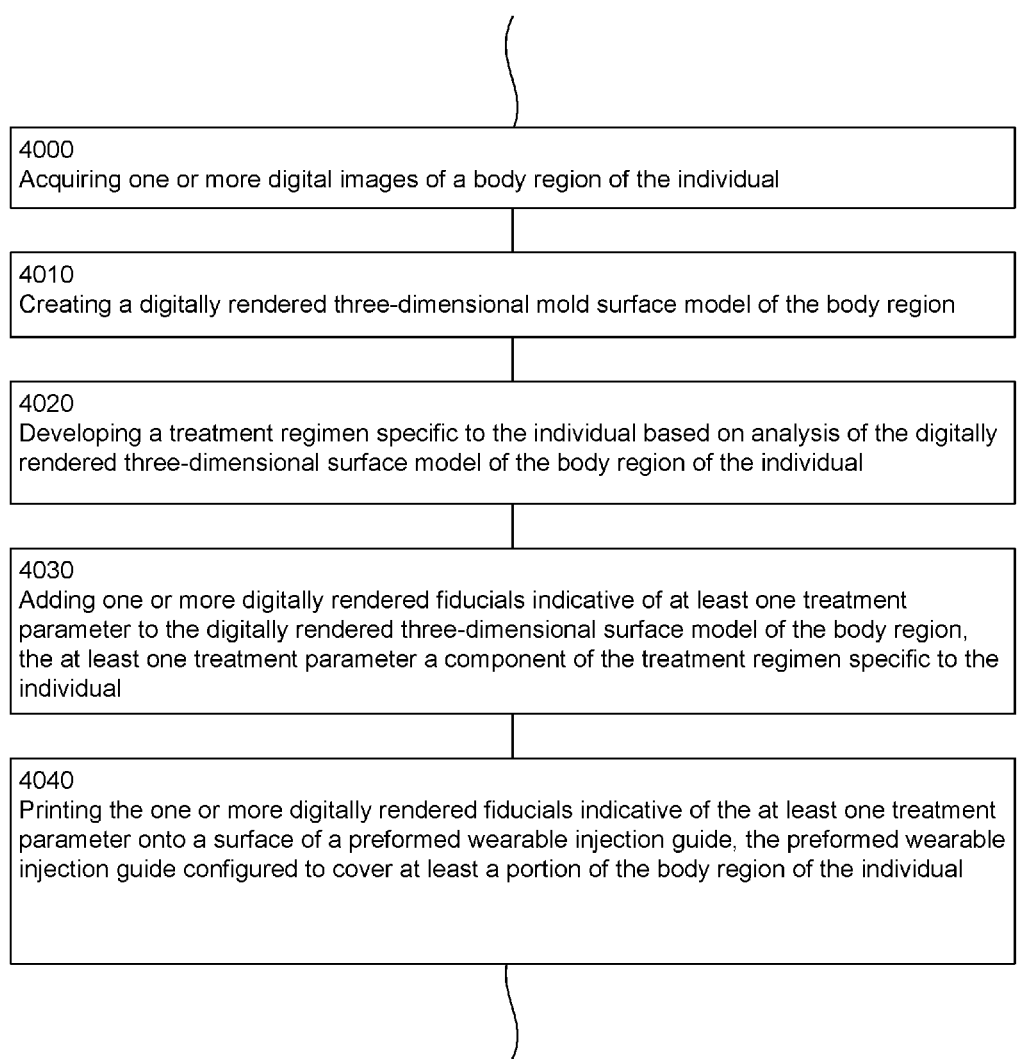
FIG. 40 is a flowchart of a method of generating a wearable injection guide.

FIG. 40 illustrates a method of generating a wearable injection guide for use on a body region of an individual. Block 4000 depicts acquiring one or more digital images of a body region of the individual. Block 4010 depicts creating a digitally rendered three-dimensional mold surface model of the body region. Block 4020 depicts developing a treatment regimen specific to the individual based on analysis of the digitally rendered three-dimensional surface model of the body region of the individual. Block 4030 depicts adding one or more digitally rendered fiducials indicative of at least one treatment parameter to the digitally rendered three-dimensional surface model of the body region, the at least one treatment parameter is a component of the treatment regimen specific to the individual. Block 4040 depicts printing the one or more digitally rendered fiducials indicative of the at least one treatment parameter onto a surface of a preformed wearable injection guide, the preformed wearable injection guide configured to cover at least a portion of the body region of the individual.

In some embodiments, developing a treatment regimen specific to the individual based on analysis of the digitally rendered three-dimensional surface model of the body region includes having a physician, other practitioner, and/or the individual analyze the digitally rendered three-dimensional surface model on a display, e.g., a computer monitor, decide which treatment regimen and associated treatment parameters are appropriate, and add one or more digitally rendered fiducials to the digitally rendered three-dimensional surface model representative of the treatment parameters. In some embodiments, a computing device, e.g., the computing device used to create the digitally rendered three-dimensional mold surface, analyzes the features of the three-dimensional surface and recommends or automatically adds one or more fiducials indicative of a treatment parameter to the model.

In some embodiments, the one or more digitally rendered fiducials are printed onto a surface of a preformed wearable injection guide using an inkjet printer configured to print onto three-dimensional objects (see, e.g., Xennia Xanadu, Xannia Technology Ltd., Hertfordshire, UK).

Figure 41:
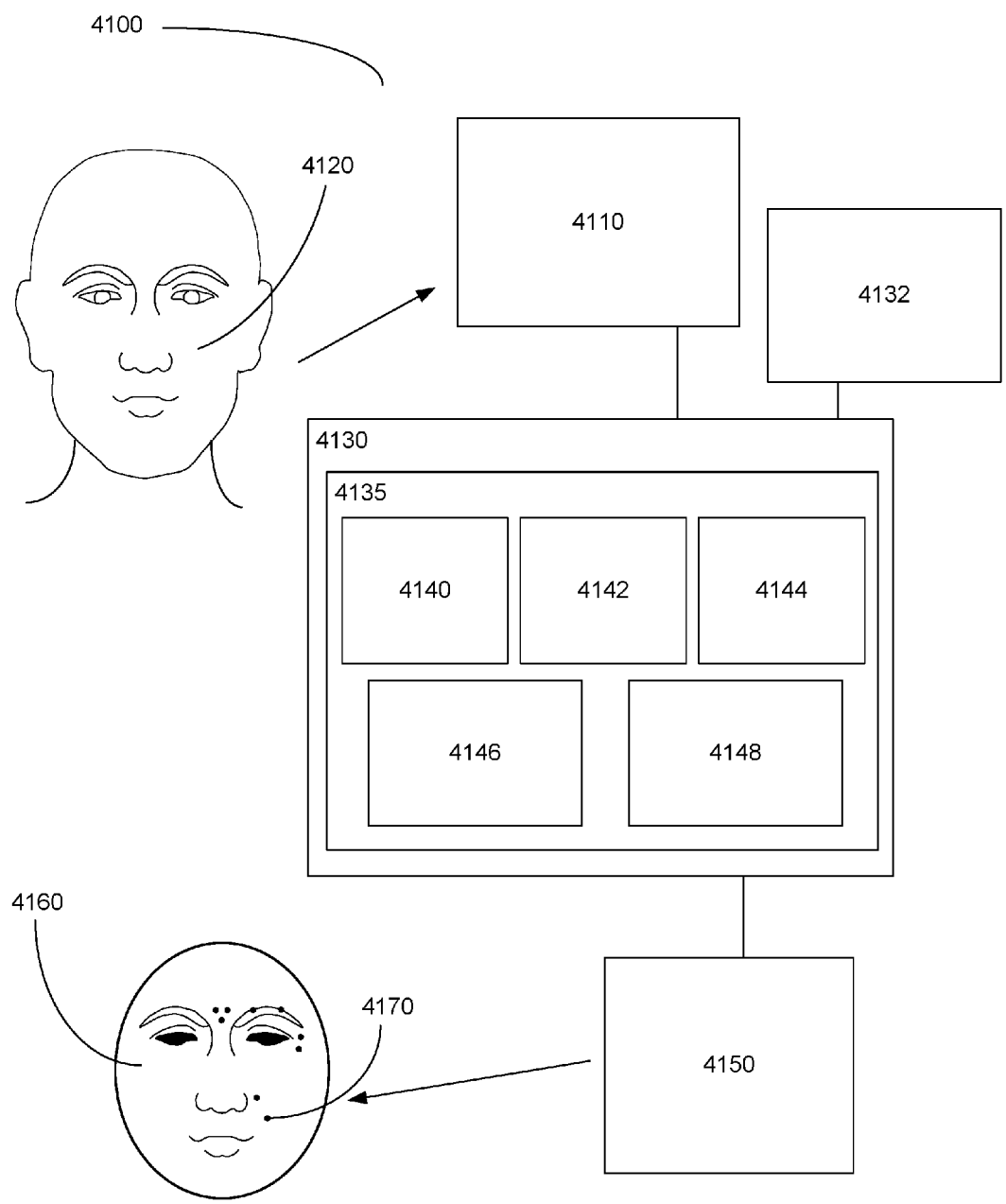
FIG. 41 is a schematic of a system for generating a wearable injection guide

FIG. 41 illustrates aspects of a system for generating a wearable injection guide for an individual. System 4100 comprises at least one image capture device 4110 configured to acquire one or more digital images of a body region 4120 of an individual. In the embodiment illustrated in FIG. 41, the body region 4120 is associated with an individual's face. However, it is contemplated that a body region from any portion of an individual's body, including the face, torso, abdomen, head, neck, upper extremities, lower extremities, buttocks, or any other body region accessible to injection can be imaged for use in generating a wearable injection guide. The image capture device can include one or more passive or active scanners, digital cameras, charge-coupled device (CCD), complementary metal oxide semiconductor (CMOS), infrared sensor, or any other device suited to capturing an image of a body region. Other non-limiting examples of an image capture device include an ultrasound device, a photoacoustic device, a thermal imaging device, a contact scanning device, a magnetic resonance imaging device, a computed tomography device, a capacitance measuring device, an electomyographic device, or other biomedical imaging devices. The at least one image capture device 4110 is further configured to transmit one or more output signals having information associated with the one or more digital images.

System 4100 of FIG. 41 further comprises a computing device 4130 operably linked to at least one image capture device 4110 and including display monitor 4132. Computing device 4130 includes non-transitory machine readable media 4135 bearing one or more instructions for generating a wearable injection guide from the one or more digital images of the body region 4120 of the individual. The non-transitory machine readable media 4135 bearing one or more instructions for generating a wearable injection guide includes one or more instructions 4140 for controlling one or more functions of the at least one image capture device 4110. In some embodiments, the one or more instructions 4140 include one or more instructions for controlling acquisition of the one or more digital images of the body region of the individual with the at least one image capture device. In some embodiments, the one or more instructions 4140 can include one or more instructions for turning the image capture device on/off, one or more instructions for modulating the quality and/or quantity of radiation, e.g., light, projected on the individual, and one or more instructions for controlling scan speed. The one or more instructions 4140 can include one or more instructions for causing movement of the at least one capture image capture device to allow image capture from different positions or angles relative to the individual.

The non-transitory machine readable media 4135 bearing one or more instructions for generating a wearable injection guide includes one or more instructions 4142 for receiving the one or more output signals having information associated with the one or more digital images from the at least one image capture device 4110. In some embodiments, the one or more instructions 4142 for receiving the one or more output signals includes one or more instructions for receiving a wired transmission from the at least one image capture device. In some embodiments, the one or more instructions 4142 for receiving the one or more output signals includes one or more instructions for receiving a wireless transmission from the at least one image capture device.

The non-transitory machine readable media 4135 bearing one or more instructions for generating a wearable injection guide includes one or more instructions 4144 for creating a digitally rendered model of the wearable injection guide from the one or more digital images of the body region of the individual. In some embodiments, the one or more instructions 4144 for creating the digitally rendered model of the wearable injection guide include one or more instructions associated with an algorithm configured to generate a digitally rendered three-dimensional model based on one or more acquired digital images. Examples of algorithms and programs for three-dimensional modeling have been described above herein.

The non-transitory machine readable media 4135 bearing one or more instructions for generating a wearable injection guide includes one or more instructions 4146 for adding one or more digitally rendered fiducials indicative of at least one treatment parameter to the digitally rendered model of the wearable injection guide. In some embodiments, the one or more instructions 4146 for adding the one or more digitally rendered fiducials includes one or more instructions for adding the one or more digitally rendered fiducials a user input device, e.g., a keyboard or touchpad associated with the computing device. In some embodiments, the one or more instructions 4146 for adding the digitally rendered fiducials includes one or more instructions for adding the one or more digitally rendered fiducials automatically to the digitally rendered model of the wearable injection guide based on formulating a treatment regimen from a comparison of the acquired one or more digital images and one or more stored digital images. The stored digital images can include previous digital images of the individual and/or normative or standard images. The comparison of the acquired one or more digital images and the one or more stored digital images by, for example an overlay and/or subtractive process is used to identify areas in need of treatment. Once an area has been identified as an area in need of treatment, the computing device may automatically add one or more digitally rendered fiducials to the digitally rendered model in the appropriate injection site locations. In some embodiments, the one or more instructions 4146 for adding the one or more digitally rendered fiducials are based on an outcome defined by the individual. For example, the individual may request enhanced lips or reduced frown lines based on analysis of the one or more digital images.

The non-transitory machine readable media 4135 bearing one or more instructions for generating a wearable injection guide includes one or more instructions 4148 for generating one or more model output signals having information for forming the wearable injection guide from the digitally rendered model of the wearable injection guide. The one or more instructions 4148 for generating one or more model output signal can include instructions for sending the model output signal wirelessly or by wire. The one or more instructions 4148 may further include one or more instructions for converting the data file containing the information regarding the digitally rendered model of the wearable injection guide into a format acceptable for transmission to a manufacturing device, e.g., additive manufacturing file (AMF) format or STL (STereoLithography) format.

System 4100 of FIG. 41 further includes manufacturing device 4150 configured to receive the one or more model output signals from the computing device 4130 and to form the wearable injection guide 4160 from the digitally rendered model of the wearable injection guide, the formed wearable injection guide 4160 including one or more fiducials 4170 indicative of the at least one treatment parameter, the one or more fiducials 4170 corresponding to the one or more digitally rendered fiducials on the digitally rendered model of the wearable injection guide. The manufacturing device 4150 can include one or more of a rapid prototyping device. The manufacturing device 4150 can include a stereolithography device, a laser scintering device, and/or a 3D printing device. Other non-limiting examples of manufacturing devices for use in forming the wearable injection guide include devices capable of fused deposition modeling, polyj etting, vacuum casting, reaction injection molding, or injection molding.

Figure 42:
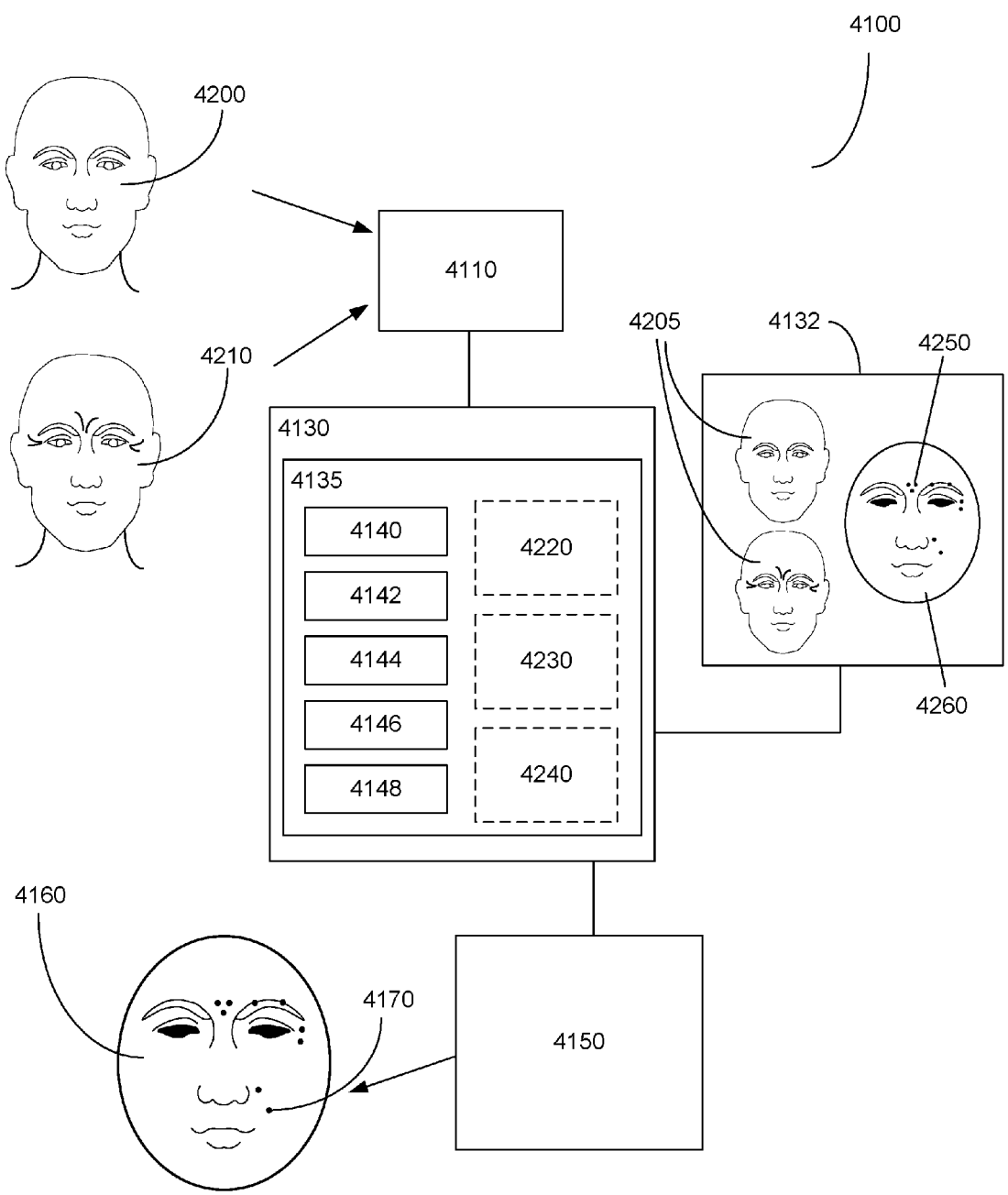
FIG. 42 is a schematic showing aspects of a system such as that depicted in FIG. 41.

FIG. 42 illustrates further aspects of a system of FIG. 41. The non-transitory machine readable media 4135 bearing one or more instructions for generating a wearable injection guide can further include one or more instructions 4220 for acquiring the one or more digital images of the body region of the individual with the at least one image capture device 4110 in at least one first expression state 4200 and at least one second expression state 4210; one or more instructions 4230 for comparing the one or more digital images 4205 of the body region of the individual in the at least one first expression state 4200 and the at least one second expression state 4210 to determine a treatment regimen; and one or more instructions 4240 for adding the one or more digitally rendered fiducials 4250 to the digitally rendered model of the wearable injection guide 4260 based on the treatment regimen.

FIG. 43 illustrates aspects of an article of manufacture for use in generating a wearable injection guide. Article of manufacture 4300 includes non-transitory machine readable media 4310 bearing one or more instructions for generating a wearable injection guide for administering an injectable agent to an individual. The non-transitory machine readable media stores instructions and/or data for use in generating a wearable injection guide. In an embodiment, non-transitory machine readable media 4310 can be computer readable media. In an embodiment, non-transitory machine readable media 4310 can be recordable-type media. Computer readable media may also be recordable-type media, and the qualities of being "computer readable" and "recordable-type" should not be construed as being mutually exclusive, though in some cases a computer readable media may not be a recordable-type media, and vice versa. Machine readable media include volatile and nonvolatile, removable and non-removable media implemented in any method or technology for storage of information such as machine readable instructions, data structures, program modules, or other data. Non-transitory machine readable media include, but are not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other media which can be used to store the desired information. In a further embodiment, computer storage media may include a group of computer storage media devices. In an embodiment, machine readable media may include an information store. In an embodiment, an information store may include a quantum memory, a photonic quantum memory, or atomic quantum memory. Combinations of any of the above may also be included within the scope of non-transitory machine readable media.

The one or more instructions of the non-transitory machine readable media include one or more instructions 4320 for controlling acquisition of the one or more digital images of a body region of the individual with at least one image capture device; one or more instructions 4330 for receiving one or more output signals having information associated with the one or more digital images of the body region from the at least on image capture device; one or more instructions 4340 for creating a digitally rendered model of the wearable injection guide from the one or more digital images of the body region of the individual; one or more instructions 4350 for generating a treatment regimen for the individual based on the one or more digital images of the body region; one or more instructions 4360 for adding one or more digitally rendered fiducials indicative of at least one treatment parameter of the treatment regimen to the digitally rendered model of the wearable injection guide; and one or more instructions 4370 for generating one or more model output signals having information for manufacturing the wearable injection guide from the digitally rendered model of the wearable injection guide.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations can include executing a special-purpose instruction sequence or invoking circuitry for enabling, triggering, coordinating, requesting, or otherwise causing one or more occurrences of virtually any functional operations described herein. In some variants, operational or other logical descriptions herein can be expressed as source code and compiled or otherwise invoked as an executable instruction sequence. In some contexts, for example, implementations can be provided, in whole or in part, by source code, such as C++, or other code sequences. In other implementations, source or other code implementation, using commercially available and/or techniques in the art, can be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) can be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

At least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, changes and modifications can be made without departing from the subject matter described herein and its broader aspects and, therefore, the appended claims are to encompass within their scope all such changes and modifications as are within the true spirit and scope of the subject matter described herein. Terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

PROPHETIC EXAMPLES

Example 1: A Wearable Injection Guide for Treating a Facial Region of an Individual with Botulinum Toxin Construction and use of a rigid wearable injection guide are described. The wearable injection guide is constructed of a rigid material substantially impenetrable to an injection needle and including one or more injection needle access regions. The wearable injection guide is formed based on a digitally rendered model of the wearable injection guide and is used for guiding injection of botulinum toxin into wrinkles associated with a forehead region of an individual.

A digitally rendered model of a wearable injection guide is generated from one or more digital images of the body region of the individual's face, including at least a portion of the individual's forehead. Briefly, two charge-coupled device cameras and a projector connected to a computer are used to scan the body region of the individual's face as described in Feng et al. *Brit. J. Oral Maxillofacial Surg.* (2010) 48:105-109, which is incorporated herein by reference. The individual's face is exposed to structured light to collect an optical representation of the body region by a point cloud of up to 300,000 points in three-dimensional coordinates. The three-dimensional coordinates are acquired by the computer and used to construct a digitally rendered model of the wearable injection guide using a CAD/CAM software package, e.g., Geomagic Studio (Morrisville, N.C.).

A triangular pattern of 9 to 13 digitally rendered injection needle-access regions are added to the forehead region of the digitally rendered model of the wearable injection guide. The 9 to 13 digitally rendered injection needle-access regions correspond to openings in the rigid material of the formed wearable injection guide through which injection needles can be inserted for injection of botulinum toxin into the underlying tissue of the body region once the formed wearable injection guide is deployed on the surface of the individual's face. The digitally rendered injection needle-access regions are placed on the digitally rendered model of the wearable injection guide in portions of the guide corresponding to the following portions of the individual's face: 0.5 centimeters below the lateral brow; in the midpupillary line, halfway between the eyebrow and the frontal scalp on each side of the model; at the vertex of the forehead; at the midline just below the meeting of the eyebrows; at the midline of the forehead, halfway between the nasal radix and the vertex of the scalp; and over the corrugators, approximately 1 centimeter above the medial portion of the each eyebrow (see, e.g., Bain et al., *Aesthetic Surg. J.* (2006) 26:617-619, which is incorporated herein by reference).

One or more digitally rendered fiducials indicating the prescribed dose of botulinum toxin for injection at each of the injection needle access regions is added to the digitally rendered model of the wearable injection guide by a physician or other practitioner using a user input device, e.g., a keyboard or touchpad associated with the computer. Typical dosages per injection site range from 1 to 6 units of botulinum toxin. One unit is defined as the median lethal dose in mice. The median lethal dose in humans is estimated at 3500 U. The physician or other practitioner decides how many units should be injected per injection site based on the depth and/or intensity of the wrinkles on the individual's forehead.

The wearable injection guide including one or more injection needle access regions and one or more fiducials indicative of at least one treatment parameter is formed from the digitally rendered model of the wearable injection guide using a commercially available 3D printer. An example of a 3D printer appropriate for a physician's office, for example, includes the uPrint SE system (from Stratasys, Eden Prairie, Minn.). In this example, software associated with the 3D printer system converts an STL format file containing data regarding the digitally rendered model of the wearable injection guide into deposition paths that guide the extrusion head of the printer, printing the wearable injection guide layer by layer. The wearable injection guide, with an overall thickness of 3 mm, is produced from a thermoplastic material, e.g., acrylonitrile butadiene styrene (ABS). Several wearable injection guides specifically designed for the individual can be printed and used at subsequent treatment appointments. Similarly, the information used to form the wearable injection guide can be saved for printing additional guides in the future.

The physician or other practitioner prepares the botulinum toxin, e.g., botulinum toxin A (BOTOX®), for injection. A 100 Unit vial of BOTOX®, which has been stored frozen, is thawed and mixed with 2.5-4.0 milliliters (ml) of 0.9% non-preserved sterile saline solution to create a final concentration of 40-25 Units/ml. Saline including a preservative or water for injection (WFI) can also be used for this purpose.

The inner surface of the wearable injection guide is coated with a thin layer of petroleum jelly (e.g., Vaseline®) and the wearable injection guide is placed on the face of the individual. In some instances, depending on the sensitivity/pain threshold of the individual, the inner surface of the wearable injection guide can also be coated with a layer of anesthetic cream, e.g., eutectic mix of local anesthetics lidocaine (2.5%) and prilocaine (2.5%). Alternatively, the wearable injection guide can be cooled in a refrigerator to 5-10 degrees centigrade prior to placement on the individual's face as a means of reducing the pain of injection and/or post-injection swelling. A 1 or 3 ml syringe with a 30-gauge needle is used for injection, although needles ranging in gauge from 27 to 32 can be used for this purpose. Appropriate length needles for this purpose include ½ (12.7 mm) inch, ⁵⁄₁₆ inch (8 mm) and ³⁄₁₆ inch (5 mm) lengths. The needles are inserted through injection needle access regions and botulinum toxin is injected through the injection needles and into the underlying muscle of the forehead.

The individual may return from 30 to 120 days for a repeat course of injections, depending upon the sustainability of the treatment. In repeat visits, the same wearable injection guide may be used with the same injection needle access regions and fiducials, if appropriate. Alternatively, the physician or other practitioner may alter the fiducials indicating new treatment parameters. Alternatively, the physician or other practitioner may choose to print a new wearable injection guide with or without modifications to the pattern of injection needle access regions and/or the one or more fiducials indicative of a treatment parameter.

Alternative patterns of injection needle access regions can be considered depending upon the region of the face in need of treatment. For example, the treatment pattern can include one or more injection needle access regions arranged for treatment of the glabella. In this instance, the glabella region can be divided into the superior-lateral region and the central and inferomedial regions. The one or more injection needle access regions are arranged in the superior-lateral region over the medial portion of the corrugators muscle near its origin. One or more additional injection needle access regions are arranged over the mid portion of the muscle belly. Each of these sites includes one or more fiducials indicating 5 units of botulinum toxin. In addition, one or more injection needle access regions are arranged over the middle of the procerus muscle belly which is slightly off midline at the levels of the superior orbital rims. This pattern is repeated on other side. Each of these sites is includes one or more fiducials indicating 6 units of botulinum toxin. One or more injection needle access region is added over the depressor supercilli muscle, which is approximately 1 centimeter above the medial canthal tendon on both sides. Each of these sites includes one or more fiducials indicating 3 units of botulinum toxin.

In another example, the treatment pattern can include one or more injection needle access regions arranged for treatment of periorbital wrinkles, i.e., "crow's feet," with the one or more injection needle access regions placed approximately 1 centimeter lateral to the lateral canthus at the outermost portion of the bony orbital rim, correlating approximately with the 10 o'clock position of the orbicularis oculi muscle. Additional injection needle access regions are incorporated into the wearable injection guide at the half-past-nine position, the half-past-8 position and the half-past-7 positions. Each site is further includes one or more fiducials indicating 3 units of botulinum toxin.

Example 2: A Wearable Injection Guide for Treating a Facial Region of an Individual with Hyaluronic Filler Construction and use of a rigid, agent coated wearable injection guide are described. The wearable injection guide is constructed of a rigid material based on the topography of the body region of an individual, the rigid material being a porous material substantially impenetrable to an injection needle and including one or more injection needle access regions, coated with one or more agents and used for treating skin folds associated with the nasolabial folds, i.e., "laugh lines," of an individual's face with injected hyaluronic acid filler.

A digitally rendered model of a wearable injection guide is generated from one or more digital images of at least a portion an individual's face with particular emphasis on the nasolabial folds. In an embodiment, the digitally rendered model of the wearable injection guide is generated using the image capture methods described in Example 1. Alternatively, the digitally rendered model of the wearable injection guide is generated using a PRIMOS optical three-dimensional in vivo skin measurement device (GFMesstechnik, Teltow, Germany). This system projects structured light, e.g., a parallel stripe pattern, onto the body region of the individual which is depicted on a charge-coupled device chip of a shooting camera through a shooting optic. The measurement system consists of a freely movable optical measurement head (with an integrated micro-mirror projector, a projection optic, a shooting optic, and a charge-coupled device recording camera) together with a computer system. The three-dimensional effect is achieved by deflection of the parallel projection stripes by the topography of the body region of the individual. The deflections are digitalized and quantitatively evaluated using software. Mathematical algorithms are used to generate a three-dimensional image of the body region of the individual which becomes the basis for the digitally rendered model of the wearable injection guide (see, e.g., Friedman et al., *Dermatol. Surg.* (2002) 28:3; Jacobi et al., *Skin Res. Technol.* (2004) 10:207-214; Levenberg *Eur. J. Dermatol.* (2010) 20:615-619, which are incorporated herein by reference).

A pattern of one to ten digitally rendered injection needle access regions are added to the digitally rendered model of the wearable injection guide. Injection of hyaluronic acid into the nasolabial folds can be done at a single injection site by the process of threading or at multiple injection sites along the fold. Threading involves injecting the needle under the skin all the way to a distant point and then slowly removing the needle while releasing the injectable agent. To accommodate threading, in which the injection needle is injected at an angle of about 10 to 30 degrees relative to the body region, the digitally rendered injection needle access regions are modeled into the digitally rendered model of the wearable injection guide at an angle of less than 90 degrees relative to the surface of the wearable injection guide. If multiple injection sites are used, multiple digitally rendered injection needle access regions are modeled into the digitally rendered model of the wearable injection guide along the linear path of the nasolabial fold.

One or more digitally rendered fiducials are also added to the digitally rendered model of the wearable injection guide indicating the dosage of hyaluronic acid filler to be used at each injection site. For injection into the nasolabial folds, the injection volume can be as high as 6 ml per fold, although preferably 1-3 ml per fold, and depends upon the depth of the folds and how much "correction" is desired by the individual. The physician or other practitioner can determine the appropriate dosage of the hyaluronic filler by assessing the depth of the nasolabial fold from viewing either the individual's face directly or the captured and processed three-dimensional image of the individual's face on a computer monitor (see, e.g., Prager & Steinkraus *Eur. J. Dermatol.* (2010) 20:748-752, which is incorporated herein by reference). Alternatively, the computing device used to generate the digitally rendered model of the wearable injection guide can include one or more algorithms to determine the appropriate dosage based on the captured image information.

The wearable injection guide is produced by 3D printing from the digitally rendered model of the wearable injection guide as described in Example 1. Alternatively, the wearable injection guide is produced by 3D printing from the digitally rendered model of the wearable injection guide using a laser sintering process with a powder starting material. For example, hydroxyapatite powder in combination with a polymer-based binder solution can be used to generate a porous ceramic-like structure (see, e.g., Seitz et al., *J. Biomed. Mater. Res. Part B: Appl. Biomater* (2005) 74B: 782-788, which is incorporated herein by reference). The porous inner surface of the resulting wearable injection guide is coated with a disinfectant, e.g., a 7% povidine-iodine solution and with a eutectic mix of local anesthetic lidocaine (2.5%) and prilocaine (2.5%). The inner surface of the wearable injection guide is covered with a protective sheet to prevent the disinfectant and anesthetic from prematurely flowing away.

The surface of the individual's face is wiped with a disinfectant, e.g., rubbing alcohol, and the wearable injection guide is immobilized on the individual's face using Velcro® straps. The hyaluronic acid filler for injection is preferably one of the agents approved by the United States Food & Drug Administration (FDA), e.g., Restylane® (from Medicis Aesthetics Inc., Scottsdale, Ariz.). Restylane is provided by the manufacturer in a disposable glass syringe. Needles ½ inch in length and either 29 or 30 gauge are recommended for use with this product. Injection of the hyaluronic acid filler through the wearable injection guide is carried out based on the placement of the injection needle access regions and the one or more fiducials indicating the treatment parameters.

Example 3: A Wearable Injection Guide for Treating Blepharospasm (Eye-Lid Spasm) with Botulinum Toxin Construction and use of a wearable injection guide are described. The wearable injection guide is constructed of a rubber-like needle penetrable material based on a digitally rendered model of the wearable injection guide that includes topography of a body region of an individual and used for treating blepharospasm (eye-lid spasm) with botulinum toxin.

A digitally rendered model of the wearable injection guide is generated from one or more digital images of the body region of an individual's face, with particular emphasis on the eye-lids. In an embodiment, the digitally rendered model of the wearable injection guide can be generated using the image capture and modeling methods described in Example 1 or Example 2. Alternatively, three-dimensional images are captured with the DSP400 and MU2 photogrammetric face scanners, non-contact scanners for capturing photographic images from multiple, e.g., four, viewpoints using separate charge-coupled device cameras (from, 3dMD, Atlanta, Ga.). Various landmarks on the face are used to align the images and can include the inner and outer canthi of both eyes, the center of the upper lip, the outer corners of the mouth, the intersection of the frontal bone and two nasal bones of the skull (nasion), the tip of the nose (pronasale), a subnasal point, and a chin point. The images are used to form a three-dimensional image that is incorporated into the digitally rendered model of the wearable injection guide using one or more of a three-dimensional modeling software program (see, e.g., Gwilliam et al., *Eur. J. Orthodontics* (2006) 28:408-415, which is incorporated herein by reference).

One or more digitally rendered fiducials indicative of at least one treatment parameter pertaining to injection of botulinum toxin are added to the digitally rendered model of the wearable injection guide for use over the eye-lid area of the individual. For the treatment of blepharospasm with a botulinum toxin, e.g., BOTOX® (from, Allergan, Inc., Irvine, Calif.), the one or more digitally rendered fiducials are placed on the digitally rendered model on portions of the guide corresponding to regions either proximal to or over the medial and lateral pre-tarsal orbicularis oculi of the upper lid and into the lateral pre-tarsal orbicularis oculi of the lower lid. Care is taken not to place injection sites near the levator palpebrae superioris and the medial lower lid to avoid complications of ptosis and diplopia, respectively. A series of 5 to 10 digitally rendered fiducials corresponding with 5 to 10 individual injection sites per eye are added to the digitally rendered model of the wearable injection guide as well as an indication of how many units of botulinum toxin should be injected, e.g., 1.25 to 3.0 units per injection, for a total of 30 units per eye. The one or more digitally rendered fiducials are also placed to avoid injection into an underlying blood vessel. The location of underlying blood vessels can be imaged using a light emitting diode illumination system such as that described in U.S. Patent Application 2008/0306392, which is incorporated herein by reference. The resulting images are incorporated into the digitally rendered model of the wearable injection guide to guide placement of the one or more digitally rendered fiducials to avoid having the final fiducials on the formed wearable injection guide overlapping with an underlying blood vessel.

The digitally rendered model of the wearable injection guide is constructed such that the inner surface is separated from the outer surface by a distance that allows injection needles of a certain length to only reach a certain depth into the underlying tissue of the body region. For example, the inner surface can be uniformly separated from the outer surface by a fixed thickness, e.g., 2 mm.

The digitally rendered model of the wearable injection guide with a 2 mm thickness is printed using a rubber-like elastomer, e.g., TangoPlus™ (from Objet Inc., Billeric, Mass.) to generate a wearable injection guide that allows for penetration of an injection needle, but only to the hub of the needle. As such, a needle 4 mm in length only reaches a depth of 2 mm into the underlying tissue of the body region when inserted through a wearable injection guide with a thickness of 2 mm.

The wearable injection guide is affixed to the individual's face with either an adhesive or straps. For example, one or more pieces of double stick tape are stuck to the inner surface of the wearable injection guide and subsequently used to adhere the wearable injection guide to the individual's face. BOTOX® is prepared for injection per the manufacturer's instructions. A 30 gauge needle with a length of 4 mm is used for injecting 1-3 units of BOTOX® per injection site depending upon the content of the one or more fiducials. The injection needles are inserted through the needle-penetrable material of the wearable injection guide per the one or more fiducials to a stop point defined by the hub of the injection needle and the BOTOX is injected into the underlying eyelid area to a depth of 2 mm. Each treatment lasts approximately three months, following which the procedure may be repeated. At that time, the one or more fiducials related to dosing and position of injection may be modified and a new wearable injection guide printed.

Example 4: A Wearable Injection Guide for Self-Injection of Ovulation Stimulation Hormones A wearable injection guide for self-injecting one or more hormones into the upper thigh to induce ovulation as part of in-vitro fertilization therapy is constructed from a digitally rendered model of the wearable injection guide based on one or more digital images of the body region of the individual.

One or more digital images of the body region of the upper thigh of the individual are acquired using one of the methods previously described herein. Alternatively, one or more digital images of the body region of the upper thigh of the individual is acquired with a standard digital camera and combined with one or more images of blood vessels at or near the surface of the skin. An example of an apparatus for imaging blood vessels is described in U.S. Pat. No. 6,522,911, which is incorporated herein by reference. When intended for use on the upper thigh of an individual, the topography of the body region may or may not be incorporated into the digitally rendered model of the wearable injection guide. However, topographical landmarks, e.g., freckles, moles, tattoos, etc., associated with the body region of the upper thigh can be used as reference points for adding one or more digitally rendered alignment marks to the digitally rendered model of the wearable injection guide.

A series of digitally rendered injection needle-access regions are added to the digitally rendered model of the wearable injection guide. The number of access regions is dependent upon the number of planned injections during the ovulation cycle, which is further dependent upon the types of injectable hormones used. Eggs are matured in vivo prior to harvesting for in vitro fertilization using some combination of gonadotropin-releasing hormone (GnRH) antagonists, follicle-stimulating hormone (FSH), and human chorionic gonadotropin (hCG). In this example, the wearable injection guide is designed for use with multiple injections of the GnRH antagonist leuprolide acetate, e.g., Lupron, and FSH over the course of 14 to 21 days and a final injection with hCG two days prior to harvesting eggs and is individualized to the individual's menstrual cycle. One or more digitally rendered fiducials indicative of at least one treatment parameter are added to the digitally rendered model of the wearable injection prior to manufacture. The one or more digitally rendered fiducials indicate the type of drug to be injected, the dose of drug to be injected, and/or the day in the treatment cycle. The one or more digitally rendered fiducials are added proximal to the digitally rendered injection needle-access regions on the digitally rendered model of the wearable injection guide. The wearable injection guide is produced from the completed digitally rendered model of the wearable injection guide using one of the manufacturing methods described herein.

Figure 44:
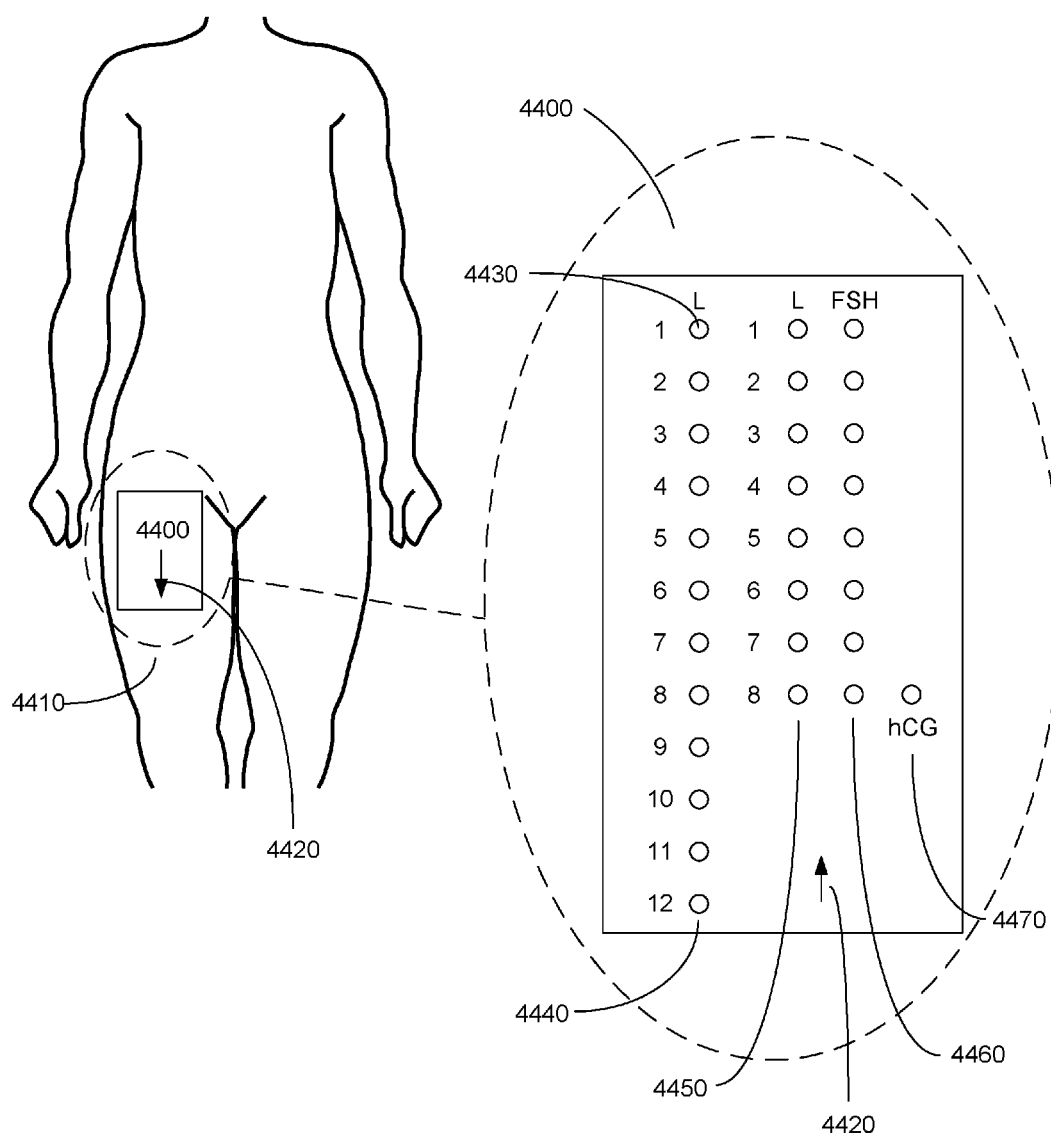
FIG. 44 is a schematic of a wearable injection guide.

An illustrative example of a wearable injection guide for self-injection of Lupron and FSH over the course of 14 to 21 days is provided in FIG. 44. Wearable injection guide 4400 configured for placement on the body region of the upper thigh 4410 of an individual includes a series of injection needle access regions 4430. The wearable injection guide 4400 has an orientation 4420 that allows the user to decipher the one or more fiducials, e.g., letters and/or numbers, on the wearable injection guide 4400 when it is deployed on the user's upper thigh 4410 but would otherwise appear upside-down to another person viewing the wearable injection guide 4400 on said user's upper thigh 4410.

In this example, the wearable injection guide is adhered to the upper thigh using a reversible adhesive. The wearable injection guide can be left in place for the full treatment period or removed after each daily injection. One or more alignment marks on the wearable injection guide are used to align the wearable injection guide to references points on the skin of the upper thigh, e.g., two or more freckles. In general, the injection cycle is as follows: On day 1 (which corresponds to day 21 of the menstrual cycle) the injection cycle is initiated by injecting the first Lupron injection. On day 9-12 (which corresponds to the day after the beginning of menstruation and is variable depending upon number of days in cycle) initiate 7 days of FSH injection. On day 16, finish injection cycle with last injections of Lupron and FSH and a single injection of HCG. Egg retrieval is done 2 days after HCG injection. One or more fiducials are included on the wearable injection guide to guide the individual on appropriate daily injections. In the non-limiting example depicted in FIG. 44, a first column 4440 of injection needle access regions 4430 are marked with an "L" for Lupron and numbered in a descending manner to indicate the first day of Lupron injection, the second day of Lupron injection, etc., out to the twelfth day of Lupron injection. A second column 4450 and a third column 4460 of injection needle access regions 4430 are marked with an "L" and "FSH" respectively and are similarly numbered to indicate the injection day. The fourth column 4470 contains a single injection needle access region 4430 reserved for the final injection with hCG two days prior to harvesting of eggs. In some instances, oral birth control pills may be combined with the injections to control the menstrual cycle. In this instance, 12-21 days of oral birth control pills may be given prior to initiation of Lupron injections.

The wearable injection guide for use in fertility treatment can include an alternative treatment regimen. For example, a second treatment option includes oral birth control pills, followed by injection of FSH and the GnRN antagonist Ganirelix. In this regimen, the wearable injection guide includes one or more fiducials indicating 6 separate injections of FSH, followed by combined injection of FSH and Ganirelix for 4 days, followed by a final injection of HCG. Prior to initiating injection treatment, oral birth control pills are given for 17 days at which point pills are stopped. This is day 1. At day 6, daily FSH injection is started. At day 11, daily Ganirelix injection is added and on day 14, the injection treatment regimen ends with HCG injection. Eggs are retrieved 2 days later.

Example 5: A Wearable Injection Guide with One or More Activatable Injection Event Indicators A wearable injection guide for guiding injection of an injectable agent including one or more activatable injection event indicators is described for use in self-injection of an injectable agent, e.g., an antibiotic, into the upper thigh. In this example, the antibiotic is Rocephin® (from Genentech USA Inc., South San Francisco, Calif.), a broad-spectrum cephalosporin antibiotic.

One or more digital images of the body region of the individual's upper thigh are acquired by a digital camera and transferred to a computing device. The one or more digital images include one or more reference points, e.g., freckles, associated with the body region of the individual's thigh. If no reference points are available on the body region, the physician or other practitioner may place one or more marks, e.g., semi-permanent ink spots, on the body region for use as one or more reference points. The digital images including the one or more reference points are used to generate a digitally rendered model of the wearable injection guide. One or more digitally rendered alignment marks coinciding with the one or more reference points on the body region are added to the digitally rendered model of the wearable injection guide.

One or more digitally rendered fiducials indicative of at least one treatment parameter are added to the digitally rendered model of the wearable injection guide. The one or more digitally rendered fiducials indicate the treatment parameters for Rocephin®, the latter of which depend upon the severity of the infection. The recommended dose for Rocephin is 1 to 2 grams given once a day (or in equally divided doses twice a day) for 4 to 14 days, and possibly longer for complicated infections. For infections caused by *Staphylococcus aureus* (MSSA), for example, the recommended daily dose is 2 to 4 grams, not to exceed 4 grams. One or more fiducials are digitally added to digitally rendered model of the wearable injection guide reflecting the dosing recommended by the physician or other practitioner. For 2 grams daily over 14 days, each of 28 injection sites on the wearable injection guide are marked with one or more fiducials indicating the dose (1 gram), the time of day (day or night) and the day (1-14). The specific treatment parameters are specified by the patient's caregiver.

The wearable injection guide is formed from the digitally rendered model of the wearable injection guide using a 3D printing method. Preferably at least a portion of the wearable injection guide is transparent such that alignment marks on the wearable injection guide can be aligned with one or more underlying reference points, e.g., freckles, on the body region. A transparent wearable injection guide is formed from the digitally rendered model of the wearable injection guide using 3D printing with Objet FullCure720™ using an Objet Connex 3D printer (from, Objet Inc., Billeric, Mass.). To form a more rubber-like semi-translucent wearable injection guide, the digitally rendered model of the wearable injection guide can be printed using Objet TangoPlus FullCure930 and an Eden 3-Dimensional Printing System (both from Objet Inc., Billeric, Mass.).

Once the wearable injection guide is printed, a layer of pressure sensitive film, e.g., FujiFilm Prescale extreme low pressure film (distributed by Tekscan, Inc., Boston, Mass.) is adhered to the outer surface of the wearable injection guide. The pressure sensitive film is used as an activatable injection event indicator to indicate whether or not a given area of the wearable injection guide has been previously accessed. In some embodiments, at least a portion of the pressure sensitive film is transparent, enabling the intended user to be able to read the one or more fiducials that have been otherwise printed on the wearable injection guide. Alternatively, the pressure sensitive film is situated such that the one or more fiducials are readable relative to placement of the pressure sensitive film. One or more biocompatible adhesive strips are affixed to the inner surface of the wearable injection guide and used to adhere the wearable injection guide to the body region of the individual.

Prior to deploying the wearable injection guide, the body region of the individual's thigh is thoroughly swabbed with alcohol to disinfect the area. The wearable injection guide is deployed onto the body region of the individual by aligning the one or more alignment marks on the wearable injection guide with one or more reference points on the body region. A 500 milligram (mg) vial of Rocephin powder is reconstituted with 1 ml of an appropriate diluent, e.g., sterile water, to a final concentration of 350 mg/ml. Alternatively, the Rocephin powder can be reconstituted in 1% lidocaine hydrochloride to ease the pain of injection. A 3 ml syringe with a 1½ inch 22 gauge needle is used to inject the appropriate dose of Rocephin through the wearable injection guide at the appropriate site and into the underlying intramuscular region of the thigh. The appropriate site is based on the one or more fiducials and whether or not the activatable injection event indicator has been previously activated.

All of the above U.S. patents, U.S. patent application publications, U.S. patent applications, foreign patents, foreign patent applications and non-patent publications referred to in this specification and/or listed in any Information Disclosure Statement, are incorporated herein by reference, to the extent not inconsistent herewith.

With respect to the appended claims, the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A system for guided injection comprising:
a wearable injection guide including
a rigid material fabricated to substantially conform in shape to a surface topography of a body region of an individual, the rigid material substantially impenetrable to an injection needle, and
one or more injection needle access regions, each of the one or more injection needle access regions including a portion of the rigid material defining an opening, the one or more injection needle access regions arranged in a treatment pattern; and
at least one removable depth-limiting adapter having a tubular structure with an inner diameter sufficient to accommodate passage of an injection needle, an outer diameter sized for placement into at least a portion of at least one of the one or more injection needle access regions of the wearable injection guide, and a length sufficient to limit a depth to which the injection needle can be injected into the body region of the individual underlying the wearable injection guide, the at least one depth-limiting adapter having at least one first portion and at least one second portion configured for telescoping to adjust a length of the at least one depth-limiting adapter.

2. The system of claim 1, wherein the at least one removable depth-limiting adapter is permeable to an injection needle.

3. The system of claim 1, wherein the inner diameter of the at least one removable depth-limiting adapter is about 0.2 millimeters to about 5.0 millimeters in diameter.

4. The system of claim 1, wherein the inner diameter of the at least one removable depth-limiting adapter is about 0.3 millimeters to about 0.8 millimeters in diameter.

5. The system of claim 1, wherein the at least one removable depth-limiting adapter includes a length of about 1 millimeter to about 25 millimeters.

6. The system of claim 1, wherein the at least one removable depth-limiting adapter is configured to allow insertion of an injection needle into the at least one removable depth-limiting adapter up to a stop point defined by a hub of the injection needle.

7. The system of claim 1, wherein the at least one first portion of the at least one removable depth-limiting adapter slides past the at least one second portion of the at least one removable depth-limiting adaptor to adjust the length of the at least one removable depth-limiting adapter.

8. The system of claim 1, wherein the rigid material of the wearable injection guide is fabricated based on a specific topography of the individual's face to substantially conform in shape to contours of the individual's face.

9. The system of claim 1, wherein the one or more injection needle access regions of the wearable injection guide are arranged in a treatment pattern specific to the individual.

10. The system of claim 1, wherein the one or more injection needle access regions of the wearable injection guide are arranged in a specific treatment pattern determined by the individual's distribution of facial lines or wrinkles.

11. The system of claim 1, wherein at least one of the one or more injection needle access regions of the wearable injection guide transects the rigid material at an angle less than 90 degrees relative to an adjacent surface of the rigid material.

12. The system of claim 1, further comprising:
an activatable injection event indicator.

13. The system of claim 12, wherein the activatable injection event indicator comprises:
a pressure sensitive dye.

14. The system of claim 12, wherein the activatable injection event indicator comprises:
a flowable dye.

15. The system of claim 12, wherein the activatable injection event indicator comprises:
an oxygen sensitive dye or a moisture sensitive dye.

16. The system of claim 12, wherein the activatable injection event indicator comprises:
a needle-penetrable membrane.

17. The system of claim 12, wherein the activatable injection event indicator is associated with at least one of the one or more injection needle access regions.

18. The system of claim 12, wherein the activatable injection event indicator is associated with the at least one removable depth-limiting adapter.

19. The system of claim 1, further comprising:
one or more fiducials indicative of at least one treatment parameter.

20. The system of claim 19, wherein the one or more fiducials are indicative of at least one needle injection depth of at least one type of injectable agent to be injected at at least one of the one or more injection needle access regions.

21. The system of claim 19, wherein the one or more fiducials are indicative of at least one of a type and dose of an injectable agent to be injected at the one or more injection needle access regions.

22. The system of claim 19, wherein the one or more fiducials are indicative of at least one of a type and dose of an injectable neurotoxin to be injected at the one or more injection needle access regions.

23. The system of claim 19, wherein the one or more fiducials are indicative of at least one of a type and dose of an injectable subcutaneous volume enhancer or an injectable dermal filler to be injected at the one or more injection needle access regions.

24. The system of claim 1, further comprising:
at least one of an analgesic, disinfectant, antiseptic, sterilant, or therapeutic agent.

25. The system of claim 24, wherein the least one of an analgesic, disinfectant, antiseptic, sterilant, or therapeutic agent is stored in an agent-containing reservoir associated with the wearable injection guide.

26. The system of claim 24, wherein the least one of an analgesic, disinfectant, antiseptic, sterilant, or therapeutic agent is part of a coating on at least one surface of the wearable injection guide.

27. The system of claim 1, wherein the wearable injection guide includes a thermal-regulating mechanism to at least one of heat or cool the wearable injection guide.

28. A method of administering an injection treatment to an individual comprising:
inserting an injection needle through a depth-limiting adapter associated with at least one of one or more injection needle access regions of a personalized wearable injection guide,
the depth-limiting adapter having a structure sized for placement into at least a portion of the at least one of the one or more injection needle access regions of the personalized wearable injection guide;
the personalized wearable injection guide including
a rigid material impermeable to an injection needle and fabricated based on a specific topography of an individual's face to substantially conform in shape to contours of the individual's face, and
the one or more injection needle access regions arranged in a treatment pattern, each of the one or more injection needle access regions including a portion of the rigid material defining an opening, and
injecting at least one injectable agent through the injection needle into an underlying tissue of the individual's face.

29. The method of claim 28, further comprising:
activating at least one of one or more activatable injection event indicators associated with at least one of the personalized wearable injection guide or the depth-limiting adapter during insertion of the injection needle through the depth-limiting adapter associated with the at least one of the one or more injection needle access regions of the personalized wearable injection guide.

30. The method of claim 28, further comprising:
inserting the injection needle through the depth-limiting adapter associated with the at least one of the one or more injection needle access regions of the personalized wearable injection guide at a 90 degree angle relative to the underlying tissue of the individual's face.

31. The method of claim 28, further comprising:
inserting the injection needle through the depth-limiting adapter associated with the at least one of the one or more injection needle access regions of the personalized wearable injection guide at less than a 90 degree angle relative to the underlying tissue of the individual's face.

32. The method of claim 28, further comprising:
aligning one or more alignment marks on the personalized wearable injection guide with one or more reference points on the individual's face.

33. The method of claim 28, wherein injecting the at least one injectable agent through the injection needle into the underlying tissue of the individual's face comprises:
injecting at least one neurotoxin into the individual's face.

34. The method of claim 28, wherein injecting the at least one injectable agent through the injection needle into the underlying tissue of the individual's face comprises:
injecting at least one of a subcutaneous volume enhancer or a dermal filler into the individual's face.

35. The method of claim 28, further comprising:
altering a temperature of the personalized wearable injection guide to a temperature above or below about 98.6 degrees Fahrenheit.

36. A system for guided injection comprising:
a personalized wearable injection guide including
a rigid material fabricated based on a specific topography of an individual's face to substantially conform in shape to contours of the individual's face, the rigid material substantially impenetrable to an injection needle, and
one or more injection needle access regions, each of the one or more injection needle access regions including a portion of the rigid material defining an opening, the one or more injection needle access regions arranged in a treatment pattern; and at least one removable depth-limiting adapter having a tubular structure with an inner diameter sufficient to accommodate passage of an injection needle, an outer diameter sized for placement into at least a portion of at least one of the one or more injection needle access regions of the personalized wearable injection guide, and a length sufficient to limit a depth to which the injection needle can be injected into tissue of the individual's face underlying the personalized wearable injection guide.

37. The system of claim 36, wherein the one or more injection needle access regions of the personalized wearable injection guide are arranged in a specific treatment pattern determined by the individual's distribution of facial lines or wrinkles.

38. The system of claim 36, wherein the at least one removable depth-limiting adapter includes at least one first portion and at least one second portion, the at least one first portion configured to slide past the at least one second portion in a telescoping manner to adjust a length of the at least one removable depth-limiting adapter.

39. The system of claim 36, further comprising:
an activatable injection event indicator associated with at least one of the personalized wearable injection guide or the at least one removable depth-limiting adapter.

40. The system of claim 36, further comprising:
one or more fiducials indicative of at least one treatment parameter, wherein the one or more fiducials are on at least one surface of the personalized wearable injection guide.

41. The system of claim 36, further comprising:
at least one of an analgesic, disinfectant, antiseptic, sterilant, or therapeutic agent associated with the personalized wearable injection guide.

* * * * *